US011365415B2

(12) United States Patent
Hromas et al.

(10) Patent No.: US 11,365,415 B2
(45) Date of Patent: Jun. 21, 2022

(54) USE OF MIR-223-3P AS A CANCER THERAPEUTIC AND METHOD FOR TREATING CANCER USING THE SAME

(71) Applicant: University of Florida Research Foundation, Inc., Gainesville, FL (US)

(72) Inventors: Robert A. Hromas, Gainesville, FL (US); Elizabeth Williamson, Gainesville, FL (US); Gayathri Srinivasan, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 920 days.

(21) Appl. No.: 16/093,465

(22) PCT Filed: Apr. 14, 2017

(86) PCT No.: PCT/US2017/027735
§ 371 (c)(1),
(2) Date: Oct. 12, 2018

(87) PCT Pub. No.: WO2017/181088
PCT Pub. Date: Oct. 19, 2017

(65) Prior Publication Data
US 2021/0189399 A1    Jun. 24, 2021

Related U.S. Application Data

(60) Provisional application No. 62/322,295, filed on Apr. 14, 2016.

(51) Int. Cl.
*C12N 15/113*    (2010.01)
*A61K 9/127*    (2006.01)
(Continued)

(52) U.S. Cl.
CPC .......... *C12N 15/1137* (2013.01); *A61K 9/127* (2013.01); *A61K 31/7068* (2013.01);
(Continued)

(58) Field of Classification Search
CPC .. A61K 31/7068; A61K 47/646; A61K 48/00; A61P 35/00; C12N 15/1137; C12N 2310/14; C12N 2310/531
See application file for complete search history.

(56) References Cited

U.S. PATENT DOCUMENTS

2014/0363469 A1    12/2014 Meyers et al.
2015/0216892 A1    8/2015 Thibonnier

FOREIGN PATENT DOCUMENTS

WO    2009021325 A1    2/2009
WO    WO-2012027206 A1 *    3/2012    .............. A61P 35/00

OTHER PUBLICATIONS

Cancer Research Wales, https://www.cancerresearchwales.co.uk/blog/no-two-cancers-are-the-same, downloaded on Dec. 14, 2021.*
(Continued)

*Primary Examiner* — Terra C Gibbs
(74) *Attorney, Agent, or Firm* — Thomas | Horstemeyer, LLP

(57) ABSTRACT

The subject invention provides a pharmaceutical composition comprising an inhibitory RNA (iRNA) that mediates sequence-specific degradation of the mRNA encoding Poly (ADP-ribose) polymerase 1 (PARP1) and methods of treating cancers by administering the pharmaceutical composition to a subject in need thereof. In one embodiment, the iRNA is miR-223, particularly, miR-223-3p or a modified miR-223-3p having substitutions and/or deletions in the sequence of miR-223-3p. In another embodiment, the cancer cells comprise one or more mutations in the genes that mediate homologous recombination DNA repair, for
(Continued)

example, BRCA1 and/or BRCA2 genes. The cancer can be breast cancer, ovarian cancer, prostate cancer, pancreatic cancer or meso thelioma. Methods of treating cancer, for example, a cancer comprising BRCA1 and/or 2 mutations, using a combination of iRNA and a second cancer therapeutic are also provided.

11 Claims, 40 Drawing Sheets

Specification includes a Sequence Listing.

(51) Int. Cl.
    *A61K 31/7068* (2006.01)
    *A61K 47/64* (2017.01)
    *A61P 35/00* (2006.01)
    *A61K 48/00* (2006.01)

(52) U.S. Cl.
    CPC ............ *A61K 47/646* (2017.08); *A61K 48/00* (2013.01); *A61P 35/00* (2018.01); *C12N 2310/141* (2013.01); *C12N 2310/3513* (2013.01); *C12N 2320/31* (2013.01)

(56) References Cited

OTHER PUBLICATIONS

Search Report and Opinion issued for application 17783297.9, dated Nov. 11, 2019.
Sugawara et al., Dual strands of the miR-223 duplex 9miR-223-5p and miR-223-3p) inhibit cancer cell aggressiveness: targeted genes are involved in bladder cancer pathogenesis, Journal of Human Genetics, 63:657-668, 2018.
Jufeng et al., MicroRNA-223 functions as an oncogene in human colorectal cancer cells, Oncology Reports 32:115-120, 2014.
Taïbi et al., miR-223: An inflammatory oncomiR enters the cardiovascular field, Biochimica et Biophysica Acta 1842 1001-1009, 2014.
Wei et al., MiR-223-3p targeting SEPT6 promotes the biological behavior of prostate cancer, Scientific Reports 4:7546, 1-8, 2014.
Dong et al., MicroRNA-223-3p suppresses leukemia inhibitory factor expression and pinopodes formation during embryo implantation in mice, Am J Transl Res, 8(2):1155-1163, 2016.
Smith et al., MicroRNAs and PARP: co-conspirators with ROS in pulmonary hypertension. Focus on "miR-223 reverses experimental pulmonary arterial hypertension", Am J Physiol Cell Physiol 309: C361-C362, 2015.
Meloche et al., miR-223 reverses experimental pulmonary arterial hypertension, Am J Physiol Cell Physiol 309: C363-C372, 2015.
Li et al., Heat Shock Protein 90B1 Plays an Oncogenic Role and is a Target of microRNA-223 in Human Osteosarcoma, Cell Physiol Biochem, 30:1481-1490, 2012.
Liang et al., MicroRNA-223 Enhances Radiation Sensitivity of U87MG Cells In Vitro and In Vivo by Targeting Ataxia Telangiectasia Mutated, International Journal of Radiation Oncology, p. 955-960, 2014.
Masciarelli et al., Gain-of-function mutant p53 downregulates miR-223 contributing to chemoresistance of cultured tumor cells, Oncogene, 33, 1601-1608, 2014.
Srinivasan et al., MiR223-3p promotes synthetic lethality in BRCA1-deficient cancers, PNAS vol. 116, No. 35, p. 17438-17443, 2019.
Wang et al., MiR-223-3p targeting epithelial cell transforming sequence 2 oncogene inhibits the activity, apoptosis, invasion and migration of MDA-MB-468 breast cancer cells, OncoTargets and Therapy, 12 7675-7684, 2019.
International Search Report for Application PCT/US2017/027735, dated Sep. 8, 2017.

\* cited by examiner

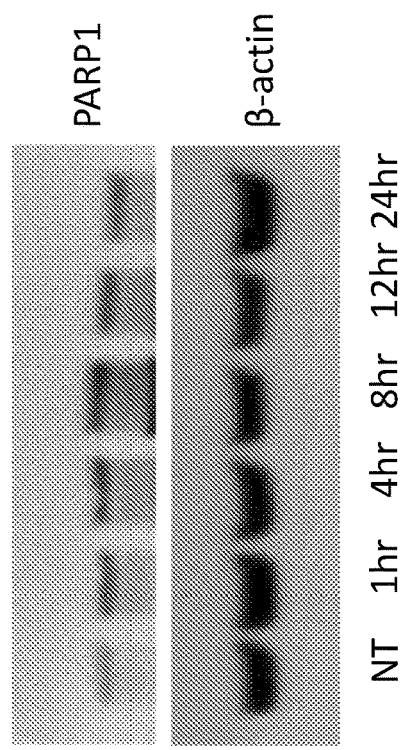
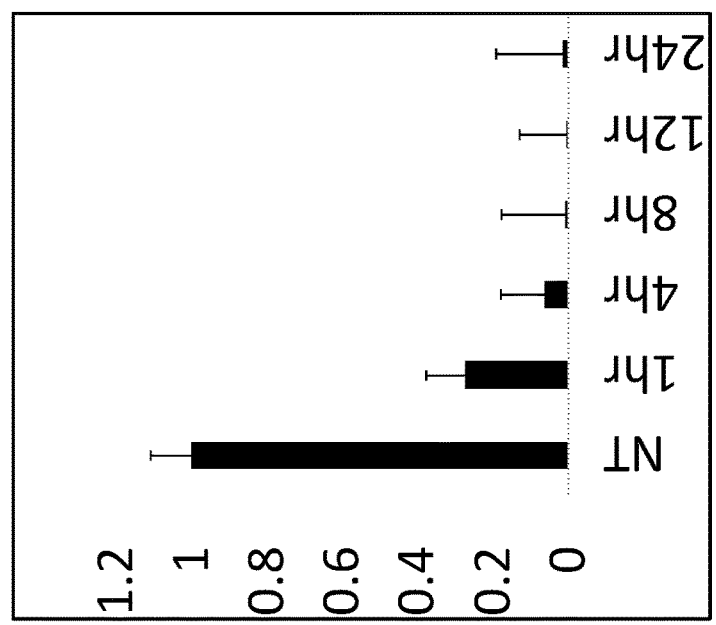
Figure 3 mirSVR score: -1.0131　　　PhastCons score: 0.4129

```
3'  accCCAUAAACUGUUUGACUGU  5'  hsa-miR-223-3p
       ||||  | |  ||||||||
232:5' ccaGGUAGAU-A-AAACUGACA  3'  PARP1 3' mRNA UTR
```

PARP1 3' UTR　　ENST00000036　　769 nt

Figure 6

3'- accCCAUCAACUGUUUGACUGu
(SEQ ID NO: 76)

3'- accCCAUCU̲ACUGUUUGACUGu
(SEQ ID NO: 77)

3'- accCCAUCU̲A-U̲GUUUGACUGu
(SEQ ID NO: 78)

3'- accCCAUCAACU-U̲UUGACUGu
(SEQ ID NO: 79)

3'- accCCAUAU̲ACUGUUUGACUGu
(SEQ ID NO: 80)

3'- accCCAUAU̲A-U̲GUUUGACUGu
(SEQ ID NO: 81)

3'- accCCAUAU̲ACU-U̲UUGACUGu
(SEQ ID NO: 82)

3'- accCCAUCAA-U̲GUUUGACUGu
(SEQ ID NO: 83)

3'- accCCAUCAA-U̲-U̲UUGACUGu
(SEQ ID NO: 84)

3'- accCCAUCU̲A-U̲-U̲UUGACUGu
(SEQ ID NO: 85)

3'- accCCAUAAA-U̲GUUUGACUGu
(SEQ ID NO: 86)

3'- accCCAUAAA-U̲-U̲UUGACUGu
(SEQ ID NO: 87)

3'- accCCAUAAACU-U̲UUGACUGu
(SEQ ID NO: 88)

3'- accCCAUAU̲A-U̲-U̲UUGACUGu
(SEQ ID NO: 89)

Figure 8

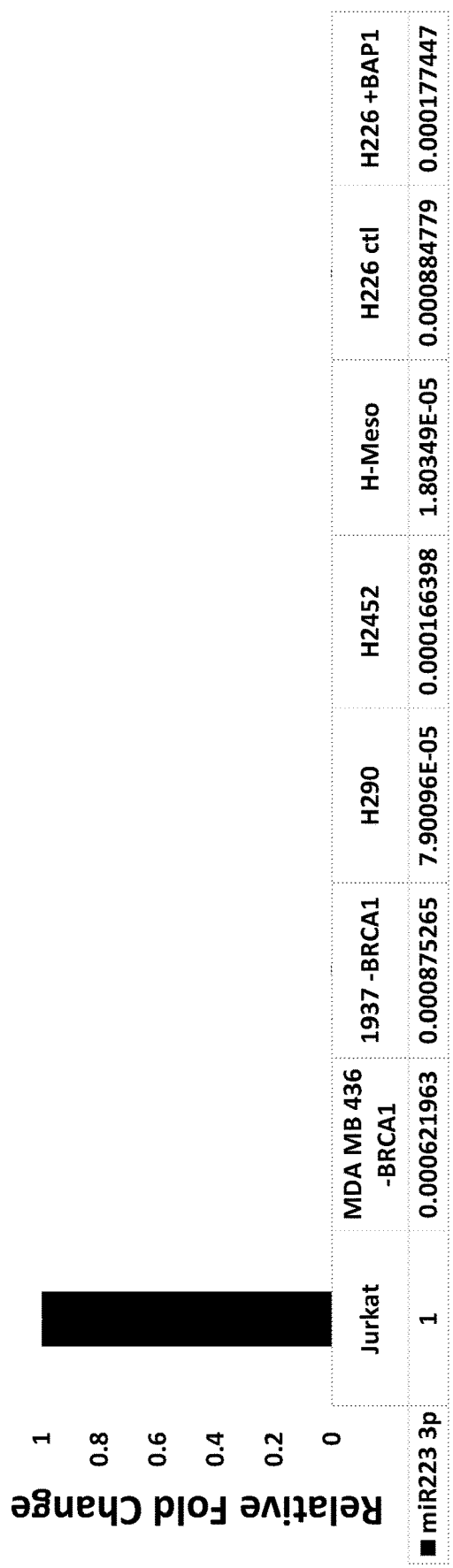
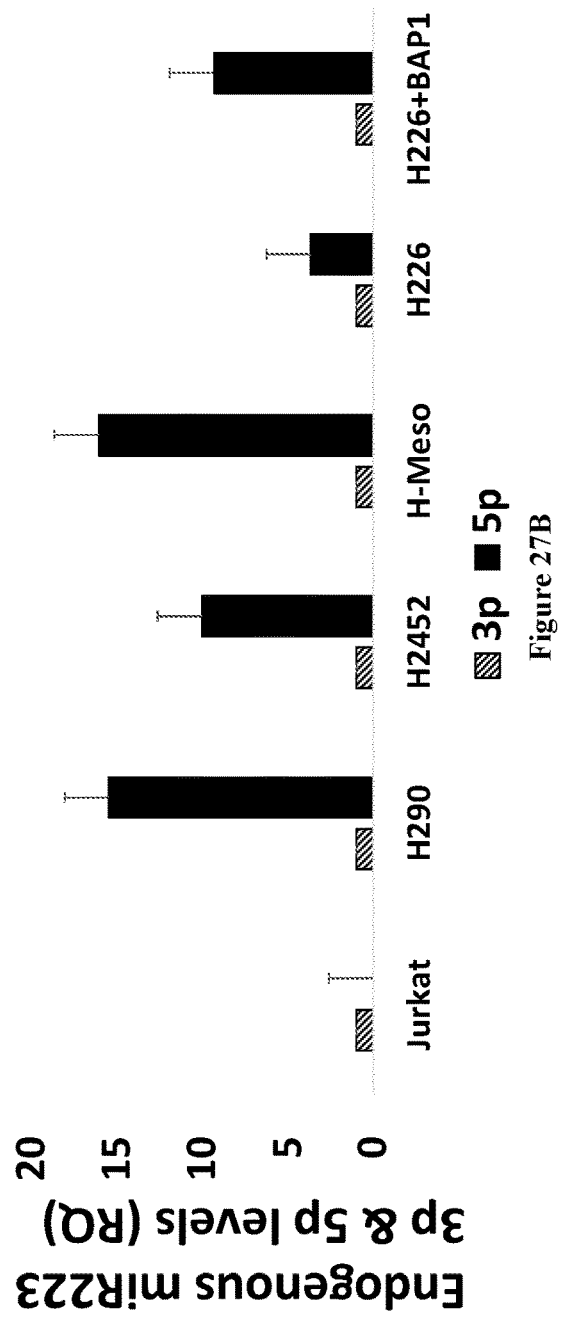
Figure 27A
Figure 27B

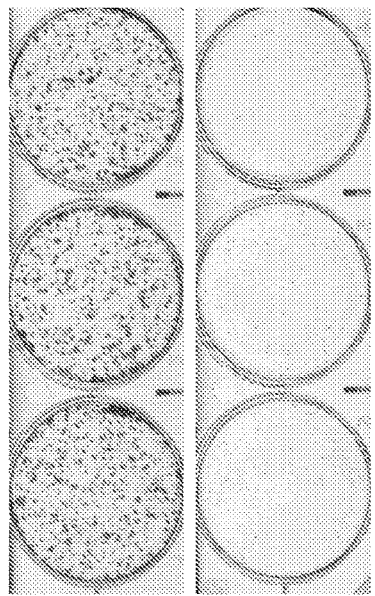
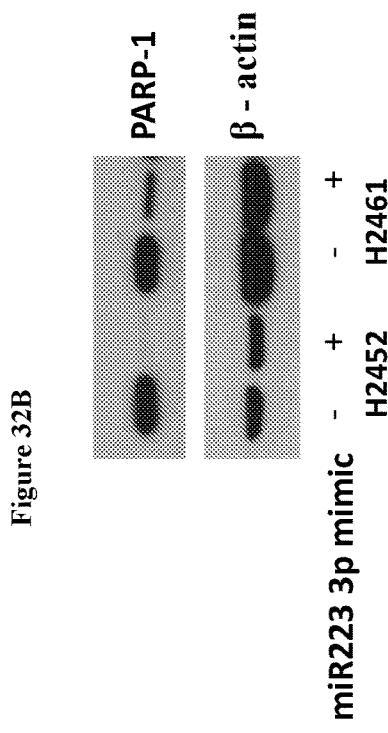
Figure 32B
Figure 32C
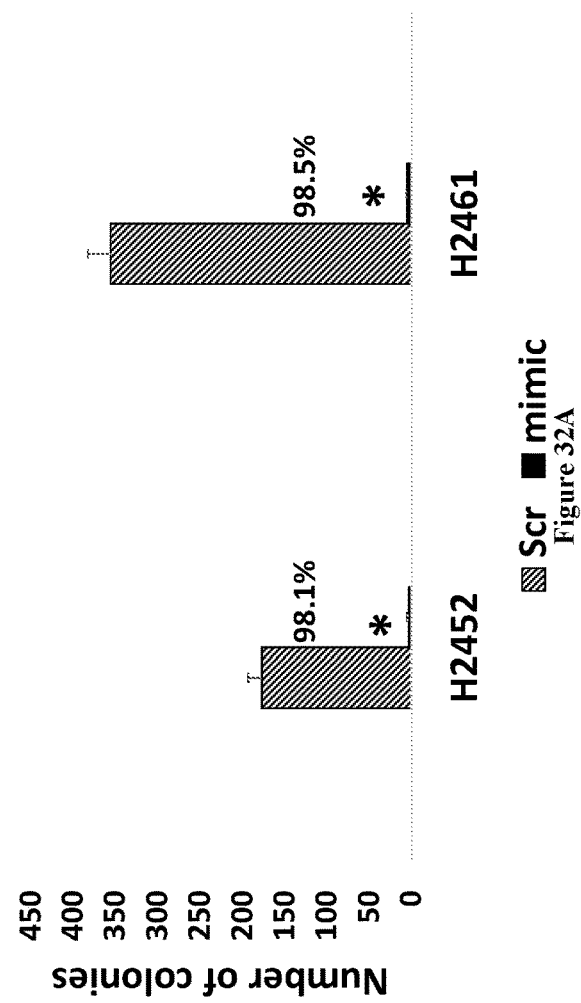
Figure 32A

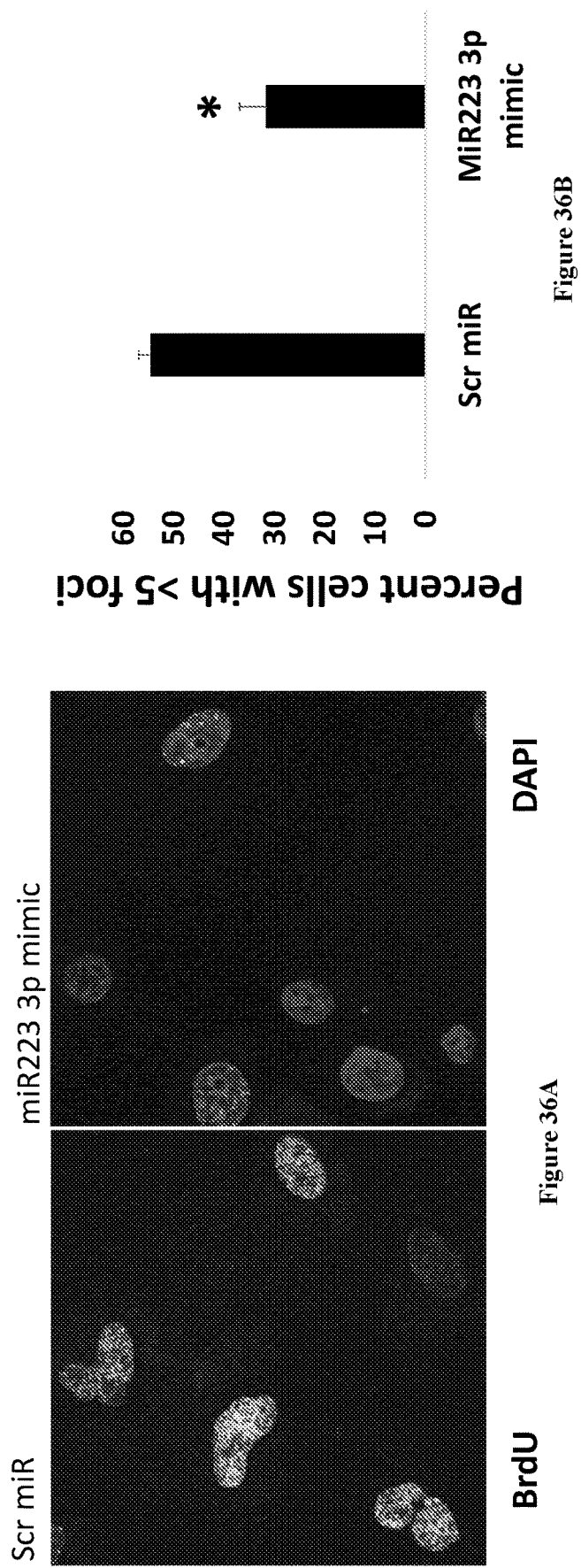
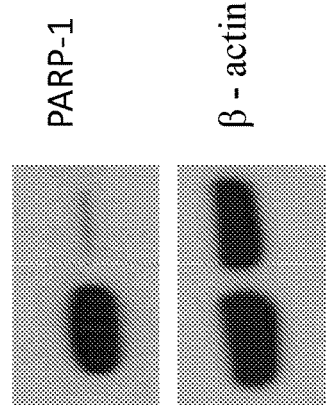
Figure 36A
Figure 36B
Figure 36C

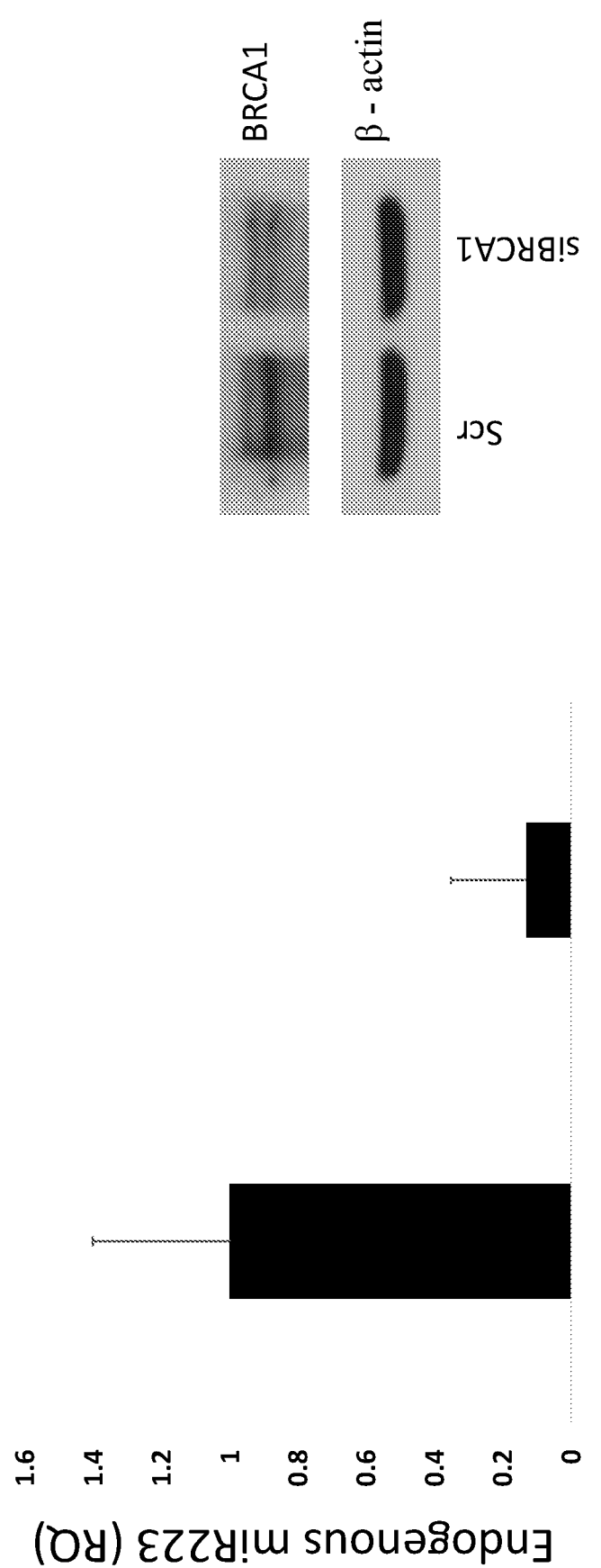
Figure 38A
Figure 38B

SEQUENCE LISTING

<160> NUMBER OF SEQ ID NOS: 111

<210> SEQ ID NO 1
<211> LENGTH: 3677
<212> TYPE: DNA
<213> ORGANISM: Homo sapiens

<400> SEQUENCE: 1

```
cggtggccgg tgcggcgtgt tcggtggcgg ctctggccgc tcaggcgcct gcggctgggt      60
gagcgcacgc gaggcggcga ggcggcagcg tgtttctagg tcgtggcgtc gggcttccgg     120
agctttgccg gcagctaggg gaggatggcg gagtcttcgg ataagctcta tcgagtcgag     180
tacgccaaga gcgggcgcgc ctcttgcaag aaatgcagcg agagcatccc caaggactcg     240
ctccggatgg ccatcatggt gcagtcgccc atgtttgatg gaaaagtccc acactggtac     300
cacttctcct gcttctggaa ggtgggccac tccatccggc accctgacgt tgaggtggat     360
gggttctctg agcttcggtg ggatgatcag cagaaagtca gaagacagc ggaagctgga     420 ggagtgacag gcaaaggcca ggatggaatt ggtagcaagg cagagaagac tctgggtgac     480
tttgcagcag agtatgccaa gtccaacaga agtacgtgca aggggtgtat ggagaagata     540
gaaaagggcc aggtgcgcct gtccaagaag atggtggacc cggagaagcc acagctaggc     600
atgattgacc gctggtacca tccaggctgc tttgtcaaga cagggagga gctgggtttc     660 cggcccgagt acagtgcgag tcagctcaag ggcttcagcc tccttgctac agaggataaa     720
gaagccctga gaagcagct cccaggagtc aagagtgaag gaaagagaaa aggcgatgag     780
gtggatggag tggatgaagt ggcgaagaag aaatctaaaa aagaaaaaga caaggatagt     840
aagcttgaaa aagccctaaa ggctcagaac gacctgatct ggaacatcaa ggacgagcta     900
aagaaagtgt gttcaactaa tgacctgaag gagctactca tcttcaacaa gcagcaagtg     960
ccttctgggg agtcggcgat cttggaccga gtagccgatg gcatggtgtt cggtgccctc    1020 cttcctgcg aggaatgctc gggtcagctg gtcttcaaga gcgatgccta ttactgcact    1080
ggggacgtca ctgcctggac caagtgtatg gtcaagacac agacacccaa ccggaaggag    1140
tgggtaaccc caaaggaatt ccgagaaatc tcttacctca agaaattgaa ggttaaaaaa    1200
caggaccgta tattccccc agaaaccagc gcctccgtgg cggccacgcc tccgccctcc    1260
acagcctcgg ctcctgctgc tgtgaactcc tctgcttcag cagataagcc attatccaac    1320
atgaagatcc tgactctcgg gaagctgtcc cggaacaagg atgaagtgaa ggccatgatt    1380
gagaaactcg gggggaagtt gacggggacg gccaacaagg cttccctgtg catcagcacc    1440
aaaaaggagg tggaaaagat gaataagaag atggaggaag taaggaagc caacatccga    1500 gttgtgtctg aggacttcct ccaggacgtc tccgcctcca ccaagagcct tcaggagttg    1560
ttcttagcgc acatcttgtc cccttggggg gcagaggtga aggcagagcc tgttgaagtt    1620
gtggccccaa gagggaagtc aggggctgcg ctctccaaaa aaagcaaggg ccaggtcaag    1680
```

-continued

```
gaggaaggta tcaacaaatc tgaaaagaga atgaaattaa ctcttaaagg aggagcagct   1740
gtggatcctg attctggact ggaacactct gcgcatgtcc tggagaaagg tgggaaggtc   1800
ttcagtgcca cccttggcct ggtggacatc gttaaaggaa ccaactccta ctacaagctg   1860
cagcttctgg aggacgacaa ggaaaacagg tattggatat tcaggtcctg gggccgtgtg   1920
ggtacggtga tcggtagcaa caaactggaa cagatgccgt ccaaggagga tgccattgag   1980
cacttcatga aattatatga agaaaaaacc gggaacgctt ggcactccaa aaatttcacg   2040
aagtatccca aaagttcta ccccctggag attgactatg ccaggatga agaggcagtg     2100 aagaagctga cagtaaatcc tggcaccaag tccaagctcc ccaagccagt tcaggacctc   2160
atcaagatga tctttgatgt ggaaagtatg aagaaagcca tggtggagta tgagatcgac   2220
cttcagaaga tgcccttggg gaagctgagc aaaaggcaga tccaggccgc atactccatc   2280
ctcagtgagg tccagcaggc ggtgtctcag gcagcagcg actctcagat cctggatctc    2340
tcaaatcgct tttacaccct gatcccccac gactttggga tgaagaagcc tccgctcctg   2400
aacaatgcag acagtgtgca ggccaaggcg aaatgcttg acaacctgct ggacatcgag    2460
gtggcctaca gtctgctcag gggagggtct gatgatagca gcaaggatcc catcgatgtc   2520
aactatgaga agctcaaaac tgacattaag gtggttgaca gagattctga agaagccgag   2580
atcatcagga gtatgttaa gaacactcat gcaaccacac acaatgcgta tgacttggaa    2640
gtcatcgata tctttaagat agagcgtgaa ggcgaatgcc agcgttacaa gccctttaag   2700
cagcttcata accgaagatt gctgtggcac gggtccagga ccaccaactt tgctgggatc   2760
ctgtcccagg gtcttcggat agccccgcct gaagcgcccg tgacaggcta catgtttggt   2820
aaagggatct atttcgctga catggtctcc aagagtgcca actactgcca tacgtctcag   2880
ggagacccaa taggcttaat cctgttggga gaagttgccc ttggaaacat gtatgaactg   2940
aagcacgctt cacatatcag caagttaccc aagggcaagc acagtgtcaa aggtttgggc   3000
aaaactaccc ctgatccttc agctaacatt agtctggatg gtgtagacgt tcctcttggg   3060
accgggattt catctggtgt gaatgacacc tctctactat ataacgagta cattgtctat   3120
gatattgctc aggtaaatct gaagtatctg ctgaaactga aattcaattt taagacctcc   3180
ctgtggtaat tgggagaggt agccgagtca cacccggtgg ctctggtatg aattcacccg   3240
aagcgcttct gcaccaactc acctggccgc taagttgctg atgggtagta cctgtactaa   3300
accacctcag aaaggatttt acagaaacgt gttaaaggtt ttctctaact tctcaagtcc   3360
cttgttttgt gttgtgtctg tggggagggg ttgtttggg gttgttttg ttttttcttg     3420 ccaggtagat aaaactgaca tagagaaaag gctggagaga gattctgttg catagactag   3480
tcctatggaa aaaccaagc ttcgttagaa tgtctgcctt actggtttcc ccagggaagg    3540
aaaaatacac ttccaccctt ttttctaagt gttcgtcttt agttttgatt ttggaaagat   3600
gttaagcatt tatttttagt taaaaataaa aactaatttc atactattta aaaaaaaaa    3660 aaaaaaaaaa aaaaaaa                                                  3677
```

<210> SEQ ID NO 2
<211> LENGTH: 1014
<212> TYPE: PRT
<213> ORGANISM: Homo sapiens

<400> SEQUENCE: 2

Met Ala Glu Ser Ser Asp Lys Leu Tyr Arg Val Glu Tyr Ala Lys Ser
1               5                   10                  15

```
Gly Arg Ala Ser Cys Lys Lys Cys Ser Glu Ser Ile Pro Lys Asp Ser
             20                  25                  30

Leu Arg Met Ala Ile Met Val Gln Ser Pro Met Phe Asp Gly Lys Val
             35                  40                  45

Pro His Trp Tyr His Phe Ser Cys Phe Trp Lys Val Gly His Ser Ile
 50                  55                  60

Arg His Pro Asp Val Glu Val Asp Gly Phe Ser Glu Leu Arg Trp Asp
 65                  70                  75                  80

Asp Gln Gln Lys Val Lys Lys Thr Ala Glu Ala Gly Val Thr Gly
                 85                  90                  95

Lys Gly Gln Asp Gly Ile Gly Ser Lys Ala Glu Lys Thr Leu Gly Asp
                100                 105                 110

Phe Ala Ala Glu Tyr Ala Lys Ser Asn Arg Ser Thr Cys Lys Gly Cys
                115                 120                 125

Met Glu Lys Ile Glu Lys Gly Gln Val Arg Leu Ser Lys Lys Met Val
        130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
                180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
        210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
                260                 265                 270

Pro Ser Gly Glu Ser Ala Ile Leu Asp Arg Val Ala Asp Gly Met Val
                275                 280                 285

Phe Gly Ala Leu Leu Pro Cys Glu Glu Cys Ser Gly Gln Leu Val Phe
        290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Val Lys Lys
                340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
        370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
        420                 425                 430
```

```
Lys Lys Glu Val Glu Lys Met Asn Lys Lys Met Glu Val Lys Glu
            435                 440                 445

Ala Asn Ile Arg Val Val Ser Glu Asp Phe Leu Gln Asp Val Ser Ala
450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Ala Pro Arg
                485                 490                 495

Gly Lys Ser Gly Ala Ala Leu Ser Lys Ser Lys Gly Gln Val Lys
            500                 505                 510

Glu Glu Gly Ile Asn Lys Ser Glu Lys Arg Met Lys Leu Thr Leu Lys
            515                 520                 525

Gly Gly Ala Ala Val Asp Pro Asp Ser Gly Leu Glu His Ser Ala His
530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
            565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
            595                 600                 605

Asp Ala Ile Glu His Phe Met Lys Leu Tyr Glu Glu Lys Thr Gly Asn
            610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
            675                 680                 685

Tyr Glu Ile Asp Leu Gln Lys Met Pro Leu Gly Lys Leu Ser Lys Arg
            690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
            755                 760                 765

Leu Asp Ile Glu Val Ala Tyr Ser Leu Leu Arg Gly Gly Ser Asp Asp
            770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Asn Ala Tyr Asp Leu Glu
            820                 825                 830

Val Ile Asp Ile Phe Lys Ile Glu Arg Glu Gly Glu Cys Gln Arg Tyr
            835                 840                 845

Lys Pro Phe Lys Gln Leu His Asn Arg Arg Leu Leu Trp His Gly Ser
```

```
                    850                 855                 860
Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Cys His Thr Ser Gln
                900                 905                 910

Gly Asp Pro Ile Gly Leu Ile Leu Leu Gly Glu Val Ala Leu Gly Asn
                915                 920                 925

Met Tyr Glu Leu Lys His Ala Ser His Ile Ser Lys Leu Pro Lys Gly
                930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Asn Asp Thr Ser Leu Leu Tyr Asn Glu Tyr Ile Val Tyr
                980                 985                 990

Asp Ile Ala Gln Val Asn Leu Lys  Tyr Leu Leu Lys Leu  Lys Phe Asn
                995                 1000                1005

Phe Lys  Thr Ser Leu Trp
    1010

<210> SEQ ID NO 3
<211> LENGTH: 19
<212> TYPE: RNA
<213> ORGANISM: Artificial Sequence
<220> FEATURE:
<223> OTHER INFORMATION: Sense strand sequence siRNA-1

<400> SEQUENCE: 3
ccucaucaag augaucuuu                                                    19

<210> SEQ ID NO 4
<211> LENGTH: 19
<212> TYPE: RNA
<213> ORGANISM: Artificial Sequence
<220> FEATURE:
<223> OTHER INFORMATION: Antisense strand sequence siRNA-1

<400> SEQUENCE: 4
aaagaucauc uugaugagg                                                    19

<210> SEQ ID NO 5
<211> LENGTH: 19
<212> TYPE: RNA
<213> ORGANISM: Artificial Sequence
<220> FEATURE:
<223> OTHER INFORMATION: Sense strand sequence siRNA-2

<400> SEQUENCE: 5
gaugaucuuu gauguggaa                                                    19

<210> SEQ ID NO 6
<211> LENGTH: 19
<212> TYPE: RNA
<213> ORGANISM: Artificial Sequence
<220> FEATURE:
<223> OTHER INFORMATION: Antisense strand sequence siRNA-2

<400> SEQUENCE: 6
uuccacauca aagaucauc                                                    19
```

```
<210> SEQ ID NO 7
<211> LENGTH: 19
<212> TYPE: RNA
<213> ORGANISM: Artificial Sequence
<220> FEATURE:
<223> OTHER INFORMATION: Sense strand sequence siRNA-3

<400> SEQUENCE: 7
gauccuggau cucucaaau                                                     19

<210> SEQ ID NO 8
<211> LENGTH: 19
<212> TYPE: RNA
<213> ORGANISM: Artificial Sequence
<220> FEATURE:
<223> OTHER INFORMATION: Antisense strand sequence siRNA-3

<400> SEQUENCE: 8
auuugagaga uccaggauc                                                     19

<210> SEQ ID NO 9
<211> LENGTH: 19
<212> TYPE: RNA
<213> ORGANISM: Artificial Sequence
<220> FEATURE:
<223> OTHER INFORMATION: Sense strand sequence siRNA-4

<400> SEQUENCE: 9
gcaaggaucc caucgaugu                                                     19

<210> SEQ ID NO 10
<211> LENGTH: 19
<212> TYPE: RNA
<213> ORGANISM: Artificial Sequence
<220> FEATURE:
<223> OTHER INFORMATION: Antisense strand sequence siRNA-4

<400> SEQUENCE: 10
acaucgaugg gauccuugc                                                     19

<210> SEQ ID NO 11
<211> LENGTH: 19
<212> TYPE: RNA
<213> ORGANISM: Artificial Sequence
<220> FEATURE:
<223> OTHER INFORMATION: Sense strand sequence siRNA-5

<400> SEQUENCE: 11
ucccaucgau gucaacuau                                                     19

<210> SEQ ID NO 12
<211> LENGTH: 19
<212> TYPE: RNA
<213> ORGANISM: Artificial Sequence
<220> FEATURE:
<223> OTHER INFORMATION: Antisense strand sequence siRNA-5

<400> SEQUENCE: 12
auaguugaca ucgauggga                                                     19

<210> SEQ ID NO 13
<211> LENGTH: 19
<212> TYPE: RNA
<213> ORGANISM: Artificial Sequence
<220> FEATURE:
```

<223> OTHER INFORMATION: Sense strand sequence siRNA-6

<400> SEQUENCE: 13
ggugguugac agagauucu                                                    19

<210> SEQ ID NO 14
<211> LENGTH: 19
<212> TYPE: RNA
<213> ORGANISM: Artificial Sequence
<220> FEATURE:
<223> OTHER INFORMATION: Antisense strand sequence siRNA-6

<400> SEQUENCE: 14
agaaucucug ucaaccacc                                                    19

<210> SEQ ID NO 15
<211> LENGTH: 19
<212> TYPE: RNA
<213> ORGANISM: Artificial Sequence
<220> FEATURE:
<223> OTHER INFORMATION: Sense strand sequence siRNA-7

<400> SEQUENCE: 15
gccgagauca ucaggaagu                                                    19

<210> SEQ ID NO 16
<211> LENGTH: 19
<212> TYPE: RNA
<213> ORGANISM: Artificial Sequence
<220> FEATURE:
<223> OTHER INFORMATION: Antisense strand sequence siRNA-7

<400> SEQUENCE: 16
acuuccugau gaucucggc                                                    19

<210> SEQ ID NO 17
<211> LENGTH: 19
<212> TYPE: RNA
<213> ORGANISM: Artificial Sequence
<220> FEATURE:
<223> OTHER INFORMATION: Sense strand sequence siRNA-8

<400> SEQUENCE: 17
gcccuuuaag cagcuucau                                                    19

<210> SEQ ID NO 18
<211> LENGTH: 19
<212> TYPE: RNA
<213> ORGANISM: Artificial Sequence
<220> FEATURE:
<223> OTHER INFORMATION: Antisense strand sequence siRNA-8

<400> SEQUENCE: 18
augaagcugc uuaaagggc                                                    19

<210> SEQ ID NO 19
<211> LENGTH: 19
<212> TYPE: RNA
<213> ORGANISM: Artificial Sequence
<220> FEATURE:
<223> OTHER INFORMATION: Sense strand sequence siRNA-9

<400> SEQUENCE: 19
ccaccaacuu ugcugggau                                                    19

```
<210> SEQ ID NO 20
<211> LENGTH: 19
<212> TYPE: RNA
<213> ORGANISM: Artificial Sequence
<220> FEATURE:
<223> OTHER INFORMATION: Antisense strand sequence siRNA-9

<400> SEQUENCE: 20
aucccagcaa aguuggugg                                                      19

<210> SEQ ID NO 21
<211> LENGTH: 19
<212> TYPE: RNA
<213> ORGANISM: Artificial Sequence
<220> FEATURE:
<223> OTHER INFORMATION: Sense strand sequence siRNA-10

<400> SEQUENCE: 21
ccaacuuugc ugggauccu                                                      19

<210> SEQ ID NO 22
<211> LENGTH: 19
<212> TYPE: RNA
<213> ORGANISM: Artificial Sequence
<220> FEATURE:
<223> OTHER INFORMATION: Antisense strand sequence siRNA-10

<400> SEQUENCE: 22
aggaucccag caaaguugg                                                      19

<210> SEQ ID NO 23
<211> LENGTH: 19
<212> TYPE: RNA
<213> ORGANISM: Artificial Sequence
<220> FEATURE:
<223> OTHER INFORMATION: Sense strand sequence siRNA-11

<400> SEQUENCE: 23
ggaguaugag aucgaccuu                                                      19

<210> SEQ ID NO 24
<211> LENGTH: 19
<212> TYPE: RNA
<213> ORGANISM: Artificial Sequence
<220> FEATURE:
<223> OTHER INFORMATION: Antisense strand sequence siRNA-11

<400> SEQUENCE: 24
aaggucgauc ucauacucc                                                      19

<210> SEQ ID NO 25
<211> LENGTH: 19
<212> TYPE: RNA
<213> ORGANISM: Artificial Sequence
<220> FEATURE:
<223> OTHER INFORMATION: Sense strand sequence siRNA-12

<400> SEQUENCE: 25
ggucugauga uagcagcaa                                                      19

<210> SEQ ID NO 26
<211> LENGTH: 19
<212> TYPE: RNA
<213> ORGANISM: Artificial Sequence
<220> FEATURE:
<223> OTHER INFORMATION: Antisense strand sequence siRNA-12
```

```
<400> SEQUENCE: 26
uugcugcuau caucagacc                                              19

<210> SEQ ID NO 27
<211> LENGTH: 19
<212> TYPE: RNA
<213> ORGANISM: Artificial Sequence
<220> FEATURE:
<223> OTHER INFORMATION: Sense strand sequence siRNA-13

<400> SEQUENCE: 27
gcguaugacu uggaaguca                                              19

<210> SEQ ID NO 28
<211> LENGTH: 19
<212> TYPE: RNA
<213> ORGANISM: Artificial Sequence
<220> FEATURE:
<223> OTHER INFORMATION: Antisense strand sequence siRNA-13

<400> SEQUENCE: 28
ugacuuccaa gucauacgc                                              19

<210> SEQ ID NO 29
<211> LENGTH: 19
<212> TYPE: RNA
<213> ORGANISM: Artificial Sequence
<220> FEATURE:
<223> OTHER INFORMATION: Sense strand sequence siRNA-14

<400> SEQUENCE: 29
ggaagucauc gauaucuuu                                              19

<210> SEQ ID NO 30
<211> LENGTH: 19
<212> TYPE: RNA
<213> ORGANISM: Artificial Sequence
<220> FEATURE:
<223> OTHER INFORMATION: Antisense strand sequence siRNA-14

<400> SEQUENCE: 30
aaagauaucg augacuucc                                              19

<210> SEQ ID NO 31
<211> LENGTH: 19
<212> TYPE: RNA
<213> ORGANISM: Artificial Sequence
<220> FEATURE:
<223> OTHER INFORMATION: Sense strand sequence siRNA-15

<400> SEQUENCE: 31
gcgaaugcca gcguuacaa                                              19

<210> SEQ ID NO 32
<211> LENGTH: 19
<212> TYPE: RNA
<213> ORGANISM: Artificial Sequence
<220> FEATURE:
<223> OTHER INFORMATION: Antisense strand sequence siRNA-15

<400> SEQUENCE: 32
uuguaacgcu ggcauucgc                                              19

<210> SEQ ID NO 33
<211> LENGTH: 19
```

```
<212> TYPE: RNA
<213> ORGANISM: Artificial Sequence
<220> FEATURE:
<223> OTHER INFORMATION: Sense strand sequence siRNA-16

<400> SEQUENCE: 33
ccagcguuac aagcccuuu                                               19

<210> SEQ ID NO 34
<211> LENGTH: 19
<212> TYPE: RNA
<213> ORGANISM: Artificial Sequence
<220> FEATURE:
<223> OTHER INFORMATION: Antisense strand sequence siRNA-16

<400> SEQUENCE: 34
aaagggcuug uaacgcugg                                               19

<210> SEQ ID NO 35
<211> LENGTH: 19
<212> TYPE: RNA
<213> ORGANISM: Artificial Sequence
<220> FEATURE:
<223> OTHER INFORMATION: Sense strand sequence siRNA-17

<400> SEQUENCE: 35
ccuuuaagca gcuucauaa                                               19

<210> SEQ ID NO 36
<211> LENGTH: 19
<212> TYPE: RNA
<213> ORGANISM: Artificial Sequence
<220> FEATURE:
<223> OTHER INFORMATION: Antisense strand sequence siRNA-17

<400> SEQUENCE: 36
uuaugaagcu gcuuaaagg                                               19

<210> SEQ ID NO 37
<211> LENGTH: 19
<212> TYPE: RNA
<213> ORGANISM: Artificial Sequence
<220> FEATURE:
<223> OTHER INFORMATION: Sense strand sequence siRNA-18

<400> SEQUENCE: 37
ggaucuauuu cgcugacau                                               19

<210> SEQ ID NO 38
<211> LENGTH: 19
<212> TYPE: RNA
<213> ORGANISM: Artificial Sequence
<220> FEATURE:
<223> OTHER INFORMATION: Antisense strand sequence siRNA-18

<400> SEQUENCE: 38
augucagcga aauagaucc                                               19

<210> SEQ ID NO 39
<211> LENGTH: 21
<212> TYPE: RNA
<213> ORGANISM: Artificial Sequence
<220> FEATURE:
<223> OTHER INFORMATION: Sense strand sequence siRNA-19

<400> SEQUENCE: 39
```

```
ggagucuucg gauaagcucu a                                              21

<210> SEQ ID NO 40
<211> LENGTH: 21
<212> TYPE: RNA
<213> ORGANISM: Artificial Sequence
<220> FEATURE:
<223> OTHER INFORMATION: Antisense strand sequence siRNA-19

<400> SEQUENCE: 40
uagagcuuau ccgaagacuc c                                              21

<210> SEQ ID NO 41
<211> LENGTH: 21
<212> TYPE: RNA
<213> ORGANISM: Artificial Sequence
<220> FEATURE:
<223> OTHER INFORMATION: Sense strand sequence siRNA-20

<400> SEQUENCE: 41
gaacaucaag gacgagcuaa a                                              21

<210> SEQ ID NO 42
<211> LENGTH: 21
<212> TYPE: RNA
<213> ORGANISM: Artificial Sequence
<220> FEATURE:
<223> OTHER INFORMATION: Antisense strand sequence siRNA-20

<400> SEQUENCE: 42
uuuagcucgu ccuugauguu c                                              21

<210> SEQ ID NO 43
<211> LENGTH: 21
<212> TYPE: RNA
<213> ORGANISM: Artificial Sequence
<220> FEATURE:
<223> OTHER INFORMATION: Sense strand sequence siRNA-21

<400> SEQUENCE: 43
ggucaaggag gaagguauca a                                              21

<210> SEQ ID NO 44
<211> LENGTH: 21
<212> TYPE: RNA
<213> ORGANISM: Artificial Sequence
<220> FEATURE:
<223> OTHER INFORMATION: Antisense strand sequence siRNA-21

<400> SEQUENCE: 44
uugauaccuu ccuccuugac c                                              21

<210> SEQ ID NO 45
<211> LENGTH: 21
<212> TYPE: RNA
<213> ORGANISM: Artificial Sequence
<220> FEATURE:
<223> OTHER INFORMATION: Sense strand sequence siRNA-22

<400> SEQUENCE: 45
ggugaucggu agcaacaaac u                                              21

<210> SEQ ID NO 46
<211> LENGTH: 21
<212> TYPE: RNA
<213> ORGANISM: Artificial Sequence
```

```
<220> FEATURE:
<223> OTHER INFORMATION: Antisense strand sequence siRNA-22

<400> SEQUENCE: 46
aguuuguugc uaccgaucac c                                              21

<210> SEQ ID NO 47
<211> LENGTH: 21
<212> TYPE: RNA
<213> ORGANISM: Artificial Sequence
<220> FEATURE:
<223> OTHER INFORMATION: Sense strand sequence siRNA-23

<400> SEQUENCE: 47
gcagugaaga agcugacagu a                                              21

<210> SEQ ID NO 48
<211> LENGTH: 21
<212> TYPE: RNA
<213> ORGANISM: Artificial Sequence
<220> FEATURE:
<223> OTHER INFORMATION: Antisense strand sequence siRNA-23

<400> SEQUENCE: 48
uacugucagc uucuucacug c                                              21

<210> SEQ ID NO 49
<211> LENGTH: 21
<212> TYPE: RNA
<213> ORGANISM: Artificial Sequence
<220> FEATURE:
<223> OTHER INFORMATION: Sense strand sequence siRNA-24

<400> SEQUENCE: 49
ggaagucauc gauaucuuua a                                              21

<210> SEQ ID NO 50
<211> LENGTH: 21
<212> TYPE: RNA
<213> ORGANISM: Artificial Sequence
<220> FEATURE:
<223> OTHER INFORMATION: Antisense strand sequence siRNA-24

<400> SEQUENCE: 50
uuaaagauau cgaugacuuc c                                              21

<210> SEQ ID NO 51
<211> LENGTH: 21
<212> TYPE: RNA
<213> ORGANISM: Artificial Sequence
<220> FEATURE:
<223> OTHER INFORMATION: Sense strand sequence siRNA-25

<400> SEQUENCE: 51
gugccaacua cugccauacg u                                              21

<210> SEQ ID NO 52
<211> LENGTH: 21
<212> TYPE: RNA
<213> ORGANISM: Artificial Sequence
<220> FEATURE:
<223> OTHER INFORMATION: Antisense strand sequence siRNA-25

<400> SEQUENCE: 52
acguauggca guaguuggca c                                              21
```

```
<210> SEQ ID NO 53
<211> LENGTH: 21
<212> TYPE: RNA
<213> ORGANISM: Artificial Sequence
<220> FEATURE:
<223> OTHER INFORMATION: Sense strand sequence shRNA-1

<400> SEQUENCE: 53
ggaguaugag aucgaccuuc a                                              21

<210> SEQ ID NO 54
<211> LENGTH: 21
<212> TYPE: RNA
<213> ORGANISM: Artificial Sequence
<220> FEATURE:
<223> OTHER INFORMATION: Antisense strand sequence shRNA-1

<400> SEQUENCE: 54
ugaaggucga ucucauacuc c                                              21

<210> SEQ ID NO 55
<211> LENGTH: 21
<212> TYPE: RNA
<213> ORGANISM: Artificial Sequence
<220> FEATURE:
<223> OTHER INFORMATION: Sense strand sequence shRNA-2

<400> SEQUENCE: 55
gcuccugaac aaugcagaca g                                              21

<210> SEQ ID NO 56
<211> LENGTH: 21
<212> TYPE: RNA
<213> ORGANISM: Artificial Sequence
<220> FEATURE:
<223> OTHER INFORMATION: Antisense strand sequence shRNA-2

<400> SEQUENCE: 56
cugucugcau uguucaggag c                                              21

<210> SEQ ID NO 57
<211> LENGTH: 21
<212> TYPE: RNA
<213> ORGANISM: Artificial Sequence
<220> FEATURE:
<223> OTHER INFORMATION: Sense strand sequence shRNA-3

<400> SEQUENCE: 57
ggucugauga uagcagcaag g                                              21

<210> SEQ ID NO 58
<211> LENGTH: 21
<212> TYPE: RNA
<213> ORGANISM: Artificial Sequence
<220> FEATURE:
<223> OTHER INFORMATION: Antisense strand sequence shRNA-3

<400> SEQUENCE: 58
ccuugcugcu aucaucagac c                                              21

<210> SEQ ID NO 59
<211> LENGTH: 21
<212> TYPE: RNA
<213> ORGANISM: Artificial Sequence
<220> FEATURE:
<223> OTHER INFORMATION: Sense strand sequence shRNA-4
```

```
<400> SEQUENCE: 59
gcaaggaucc caucgauguc a                                              21

<210> SEQ ID NO 60
<211> LENGTH: 21
<212> TYPE: RNA
<213> ORGANISM: Artificial Sequence
<220> FEATURE:
<223> OTHER INFORMATION: Antisense strand sequence shRNA-4

<400> SEQUENCE: 60
ugacaucgau gggauccuug c                                              21

<210> SEQ ID NO 61
<211> LENGTH: 21
<212> TYPE: RNA
<213> ORGANISM: Artificial Sequence
<220> FEATURE:
<223> OTHER INFORMATION: Sense strand sequence shRNA-5

<400> SEQUENCE: 61
gcaaccacac acaaugcgua u                                              21

<210> SEQ ID NO 62
<211> LENGTH: 21
<212> TYPE: RNA
<213> ORGANISM: Artificial Sequence
<220> FEATURE:
<223> OTHER INFORMATION: Antisense strand sequence shRNA-5

<400> SEQUENCE: 62
auacgcauug uguugguug c                                               21

<210> SEQ ID NO 63
<211> LENGTH: 21
<212> TYPE: RNA
<213> ORGANISM: Artificial Sequence
<220> FEATURE:
<223> OTHER INFORMATION: Sense strand sequence shRNA-6

<400> SEQUENCE: 63
gcguaugacu uggaagucau c                                              21

<210> SEQ ID NO 64
<211> LENGTH: 21
<212> TYPE: RNA
<213> ORGANISM: Artificial Sequence
<220> FEATURE:
<223> OTHER INFORMATION: Antisense strand sequence shRNA-6

<400> SEQUENCE: 64
gaugacuucc aagucauacg c                                              21

<210> SEQ ID NO 65
<211> LENGTH: 21
<212> TYPE: RNA
<213> ORGANISM: Artificial Sequence
<220> FEATURE:
<223> OTHER INFORMATION: Sense strand sequence shRNA-7

<400> SEQUENCE: 65
gccagcguua caagcccuuu a                                              21

<210> SEQ ID NO 66
```

```
<211> LENGTH: 21
<212> TYPE: RNA
<213> ORGANISM: Artificial Sequence
<220> FEATURE:
<223> OTHER INFORMATION: Antisense strand sequence shRNA-7

<400> SEQUENCE: 66
uaaagggcuu guaacgcugg c                                              21

<210> SEQ ID NO 67
<211> LENGTH: 21
<212> TYPE: RNA
<213> ORGANISM: Artificial Sequence
<220> FEATURE:
<223> OTHER INFORMATION: Sense strand sequence shRNA-8

<400> SEQUENCE: 67
gcccuuuaag cagcuucaua a                                              21

<210> SEQ ID NO 68
<211> LENGTH: 21
<212> TYPE: RNA
<213> ORGANISM: Artificial Sequence
<220> FEATURE:
<223> OTHER INFORMATION: Antisense strand sequence shRNA-8

<400> SEQUENCE: 68
uuaugaagcu gcuuaaaggg c                                              21

<210> SEQ ID NO 69
<211> LENGTH: 21
<212> TYPE: RNA
<213> ORGANISM: Artificial Sequence
<220> FEATURE:
<223> OTHER INFORMATION: Sense strand sequence shRNA-9

<400> SEQUENCE: 69
ggaucuauuu cgcugacaug g                                              21

<210> SEQ ID NO 70
<211> LENGTH: 21
<212> TYPE: RNA
<213> ORGANISM: Artificial Sequence
<220> FEATURE:
<223> OTHER INFORMATION: Antisense strand sequence RNA-9

<400> SEQUENCE: 70
ccaugucagc gaaauagauc c                                              21

<210> SEQ ID NO 71
<211> LENGTH: 21
<212> TYPE: RNA
<213> ORGANISM: Artificial Sequence
<220> FEATURE:
<223> OTHER INFORMATION: Sense strand sequence shRNA-10

<400> SEQUENCE: 71
gccaacuacu gccauacguc u                                              21

<210> SEQ ID NO 72
<211> LENGTH: 21
<212> TYPE: RNA
<213> ORGANISM: Artificial Sequence
<220> FEATURE:
<223> OTHER INFORMATION: Antisense strand sequence shRNA-10

<400> SEQUENCE: 72
```

```
agacguaugg caguaguugg c                                              21

<210> SEQ ID NO 73
<211> LENGTH: 110
<212> TYPE: RNA
<213> ORGANISM: Artificial Sequence
<220> FEATURE:
<223> OTHER INFORMATION: pre-miR-223

<400> SEQUENCE: 73
ccuggccucc ugcagugcca cgcuccgugu auuugacaag cugaguugga cacuccaugu    60
gguagagugu caguuuguca aauacccaa gugcggcaca ugcuuaccag               110

<210> SEQ ID NO 74
<211> LENGTH: 22
<212> TYPE: RNA
<213> ORGANISM: Artificial Sequence
<220> FEATURE:
<223> OTHER INFORMATION: miR-223-5p

<400> SEQUENCE: 74
cguguauuug acaagcugag uu                                             22

<210> SEQ ID NO 75
<211> LENGTH: 22
<212> TYPE: RNA
<213> ORGANISM: Artificial Sequence
<220> FEATURE:
<223> OTHER INFORMATION: miR-223-3p

<400> SEQUENCE: 75
ugucaguuug ucaaauaccc ca                                             22

<210> SEQ ID NO 76
<211> LENGTH: 22
<212> TYPE: RNA
<213> ORGANISM: Artificial Sequence
<220> FEATURE:
<223> OTHER INFORMATION: Modified miR-223

<400> SEQUENCE: 76
ugucaguuug ucaacuaccc ca                                             22

<210> SEQ ID NO 77
<211> LENGTH: 22
<212> TYPE: RNA
<213> ORGANISM: Artificial Sequence
<220> FEATURE:
<223> OTHER INFORMATION: Modified miR-223

<400> SEQUENCE: 77
ugucaguuug ucaucuaccc ca                                             22

<210> SEQ ID NO 78
<211> LENGTH: 21
<212> TYPE: RNA
<213> ORGANISM: Artificial Sequence
<220> FEATURE:
<223> OTHER INFORMATION: Modified miR-223

<400> SEQUENCE: 78
ugucaguuug uaucuacccc a                                              21

<210> SEQ ID NO 79
```

```
<211> LENGTH: 21
<212> TYPE: RNA
<213> ORGANISM: Artificial Sequence
<220> FEATURE:
<223> OTHER INFORMATION: Modified miR-223

<400> SEQUENCE: 79
ugucaguuuu caacuacccc a                                              21

<210> SEQ ID NO 80
<211> LENGTH: 22
<212> TYPE: RNA
<213> ORGANISM: Artificial Sequence
<220> FEATURE:
<223> OTHER INFORMATION: Modified miR-223

<400> SEQUENCE: 80
ugucaguuug ucauauaccc ca                                             22

<210> SEQ ID NO 81
<211> LENGTH: 21
<212> TYPE: RNA
<213> ORGANISM: Artificial Sequence
<220> FEATURE:
<223> OTHER INFORMATION: Modified miR-223

<400> SEQUENCE: 81
ugucaguuug uauauacccc a                                              21

<210> SEQ ID NO 82
<211> LENGTH: 21
<212> TYPE: RNA
<213> ORGANISM: Artificial Sequence
<220> FEATURE:
<223> OTHER INFORMATION: Modified miR-223

<400> SEQUENCE: 82
ugucaguuuu cauauacccc a                                              21

<210> SEQ ID NO 83
<211> LENGTH: 21
<212> TYPE: RNA
<213> ORGANISM: Artificial Sequence
<220> FEATURE:
<223> OTHER INFORMATION: Modified miR-223

<400> SEQUENCE: 83
ugucaguuug uaacuacccc a                                              21

<210> SEQ ID NO 84
<211> LENGTH: 20
<212> TYPE: RNA
<213> ORGANISM: Artificial Sequence
<220> FEATURE:
<223> OTHER INFORMATION: Modified miR-223

<400> SEQUENCE: 84
ugucaguuuu aacuacccca                                                20

<210> SEQ ID NO 85
<211> LENGTH: 20
<212> TYPE: RNA
<213> ORGANISM: Artificial Sequence
<220> FEATURE:
<223> OTHER INFORMATION: Modified miR-223

<400> SEQUENCE: 85
```
ugucaguuuu aucuacccca                                                     20

<210> SEQ ID NO 86
<211> LENGTH: 21
<212> TYPE: RNA
<213> ORGANISM: Artificial Sequence
<220> FEATURE:
<223> OTHER INFORMATION: Modified miR-223

<400> SEQUENCE: 86
ugucaguuug uaaauaccccc a                                                  21

<210> SEQ ID NO 87
<211> LENGTH: 20
<212> TYPE: RNA
<213> ORGANISM: Artificial Sequence
<220> FEATURE:
<223> OTHER INFORMATION: Modified miR-223

<400> SEQUENCE: 87
ugucaguuuu aaauacccca                                                     20

<210> SEQ ID NO 88
<211> LENGTH: 21
<212> TYPE: RNA
<213> ORGANISM: Artificial Sequence
<220> FEATURE:
<223> OTHER INFORMATION: Modified miR-223

<400> SEQUENCE: 88
ugucaguuuu caaauaccccc a                                                  21

<210> SEQ ID NO 89
<211> LENGTH: 20
<212> TYPE: RNA
<213> ORGANISM: Artificial Sequence
<220> FEATURE:
<223> OTHER INFORMATION: Modified miR-223

<400> SEQUENCE: 89
ugucaguuuu auauacccca                                                     20

<210> SEQ ID NO 90
<211> LENGTH: 19
<212> TYPE: DNA
<213> ORGANISM: Artificial Sequence
<220> FEATURE:
<223> OTHER INFORMATION: Forward primer

<400> SEQUENCE: 90
tgtcagtttg tcaaatacc                                                      19

<210> SEQ ID NO 91
<211> LENGTH: 19
<212> TYPE: DNA
<213> ORGANISM: Artificial Sequence
<220> FEATURE:
<223> OTHER INFORMATION: Reverse primer

<400> SEQUENCE: 91
gaacatgtct gcgtatctc                                                      19

<210> SEQ ID NO 92
<211> LENGTH: 20
<212> TYPE: RNA

```
<213> ORGANISM: Artificial Sequence
<220> FEATURE:
<223> OTHER INFORMATION: PARP1 3' mRNA UTR

<400> SEQUENCE: 92
ccagguagau aaaacugaca                                                      20

<210> SEQ ID NO 93
<211> LENGTH: 22
<212> TYPE: RNA
<213> ORGANISM: Artificial Sequence
<220> FEATURE:
<223> OTHER INFORMATION: Modified miR-223-3p

<400> SEQUENCE: 93
uaugucaguu uuaaauaccu ca                                                   22

<210> SEQ ID NO 94
<211> LENGTH: 110
<212> TYPE: RNA
<213> ORGANISM: Artificial Sequence
<220> FEATURE:
<223> OTHER INFORMATION: Synthetic Construct

<400> SEQUENCE: 94
ccuggccucc ugcagugcca cgcuccgugu auuugacaag cugaguugga cacuccaugu          60
gguagagugu caguuuguca aauaccccaa gugcggcaca ugcuuaccag                    110

<210> SEQ ID NO 95
<211> LENGTH: 110
<212> TYPE: RNA
<213> ORGANISM: Artificial Sequence
<220> FEATURE:
<223> OTHER INFORMATION: Synthetic Construct

<400> SEQUENCE: 95
ccuggccucc ugcagugcca cgcuccgugu aguugacaag cugaguugga cacuccaugu          60
gguagagugu caguuuguca acuaccccaa gugcggcaca ugcuuaccag                    110

<210> SEQ ID NO 96
<211> LENGTH: 110
<212> TYPE: RNA
<213> ORGANISM: Artificial Sequence
<220> FEATURE:
<223> OTHER INFORMATION: Synthetic Construct

<400> SEQUENCE: 96
ccuggccucc ugcagugcca cgcuccgugu agaugacaag cugaguugga cacuccaugu          60
gguagagugu caguuuguca ucuaccccaa gugcggcaca ugcuuaccag                    110

<210> SEQ ID NO 97
<211> LENGTH: 110
<212> TYPE: RNA
<213> ORGANISM: Artificial Sequence
<220> FEATURE:
<223> OTHER INFORMATION: Synthetic Construct

<400> SEQUENCE: 97
ccuggccucc ugcagugcca cgcuccgugu auaugacaag cugaguugga cacuccaugu          60
gguagagugu caguuuguca uauaccccaa gugcggcaca ugcuuaccag                    110

<210> SEQ ID NO 98
<211> LENGTH: 108
```

```
<212> TYPE: RNA
<213> ORGANISM: Artificial Sequence
<220> FEATURE:
<223> OTHER INFORMATION: Synthetic Construct

<400> SEQUENCE: 98
ccuggccucc ugcagugcca cgcuccgugu agauacaagc ugaguuggac acuccaugug    60
guagaguguc aguuguauc uaccccaagu gcggcacaug cuuaccag                 108

<210> SEQ ID NO 99
<211> LENGTH: 106
<212> TYPE: RNA
<213> ORGANISM: Artificial Sequence
<220> FEATURE:
<223> OTHER INFORMATION: Synthetic Construct

<400> SEQUENCE: 99
ccuggccucc ugcagugcca cgcuccgugu agauaaagcu gaguuggaca cuccauguggg   60 uagaguguca guuuaucua ccccaagugc ggcacaugcu uaccag                   106

<210> SEQ ID NO 100
<211> LENGTH: 106
<212> TYPE: RNA
<213> ORGANISM: Artificial Sequence
<220> FEATURE:
<223> OTHER INFORMATION: Synthetic Construct

<400> SEQUENCE: 100
ccuggccucc ugcagugcca cgcuccgugu auauaaagcu gaguuggaca cuccauguggg   60 uagaguguca guuuauaua ccccaagugc ggcacaugcu uaccag                   106

<210> SEQ ID NO 101
<211> LENGTH: 108
<212> TYPE: RNA
<213> ORGANISM: Artificial Sequence
<220> FEATURE:
<223> OTHER INFORMATION: Synthetic Construct

<400> SEQUENCE: 101
ccuggccucc ugcagugcca cgcuccgugu auaugaaagc ugaguuggac acuccaugug    60
guagaguguc aguuucaua uaccccaagu gcggcacaug cuuaccag                 108

<210> SEQ ID NO 102
<211> LENGTH: 108
<212> TYPE: RNA
<213> ORGANISM: Artificial Sequence
<220> FEATURE:
<223> OTHER INFORMATION: Synthetic Construct

<400> SEQUENCE: 102
ccuggccucc ugcagugcca cgcuccgugu auauacaagc ugaguuggac acuccaugug    60
guagaguguc aguuguaua uaccccaagu gcggcacaug cuuaccag                 108

<210> SEQ ID NO 103
<211> LENGTH: 106
<212> TYPE: RNA
<213> ORGANISM: Artificial Sequence
<220> FEATURE:
<223> OTHER INFORMATION: Synthetic Construct

<400> SEQUENCE: 103
ccuggccucc ugcagugcca cgcuccgugu aguuaaagcu gaguuggaca cuccauguggg   60
```
uagaguguca guuuuaacua ccccaagugc ggcacaugcu uaccag             106

<210> SEQ ID NO 104
<211> LENGTH: 108
<212> TYPE: RNA
<213> ORGANISM: Artificial Sequence
<220> FEATURE:
<223> OTHER INFORMATION: Synthetic Construct

<400> SEQUENCE: 104
ccuggccucc ugcagugcca cgcuccgugu aguuacaagc ugaguuggac acuccaugug    60
guagaguguc aguuuguaac uaccccaagu gcggcacaug cuuaccag              108

<210> SEQ ID NO 105
<211> LENGTH: 108
<212> TYPE: RNA
<213> ORGANISM: Artificial Sequence
<220> FEATURE:
<223> OTHER INFORMATION: Synthetic Construct

<400> SEQUENCE: 105
ccuggccucc ugcagugcca cgcuccgugu aguugaaagc ugaguuggac acuccaugug    60
guagaguguc aguuucaac uaccccaagu gcggcacaug cuuaccag               108

<210> SEQ ID NO 106
<211> LENGTH: 108
<212> TYPE: RNA
<213> ORGANISM: Artificial Sequence
<220> FEATURE:
<223> OTHER INFORMATION: Synthetic Construct

<400> SEQUENCE: 106
ccuggccucc ugcagugcca cgcuccgugu auuuacaagc ugaguuggac acuccaugug    60
guagaguguc aguuuguaaa uaccccaagu gcggcacaug cuuaccag              108

<210> SEQ ID NO 107
<211> LENGTH: 108
<212> TYPE: RNA
<213> ORGANISM: Artificial Sequence
<220> FEATURE:
<223> OTHER INFORMATION: Synthetic Construct

<400> SEQUENCE: 107
ccuggccucc ugcagugcca cgcuccgugu auuugaaagc ugaguuggac acuccaugug    60
guagaguguc aguuucaaa uaccccaagu gcggcacaug cuuaccag               108

<210> SEQ ID NO 108
<211> LENGTH: 106
<212> TYPE: RNA
<213> ORGANISM: Artificial Sequence
<220> FEATURE:
<223> OTHER INFORMATION: Synthetic Construct

<400> SEQUENCE: 108
ccuggccucc ugcagugcca cgcuccgugu auuuaaagcu gaguuggaca cuccaugugg    60
uagaguguca guuuaaaua ccccaagugc ggcacaugcu uaccag                 106

<210> SEQ ID NO 109
<211> LENGTH: 22
<212> TYPE: RNA
<213> ORGANISM: Artificial Sequence
<220> FEATURE:
<223> OTHER INFORMATION: Synthetic Construct

```
<400> SEQUENCE: 109
ugucaguuug ucaaauaccc ca                                              22

<210> SEQ ID NO 110
<211> LENGTH: 22
<212> TYPE: RNA
<213> ORGANISM: Artificial Sequence
<220> FEATURE:
<223> OTHER INFORMATION: Synthetic Construct

<400> SEQUENCE: 110
ccagguagau aaaacugaca ua                                              22

<210> SEQ ID NO 111
<211> LENGTH: 22
<212> TYPE: RNA
<213> ORGANISM: Artificial Sequence
<220> FEATURE:
<223> OTHER INFORMATION: Synthetic Construct

<400> SEQUENCE: 111
uaugucaguu uuaaauaccu ca                                              22
```

USE OF MIR-223-3P AS A CANCER THERAPEUTIC AND METHOD FOR TREATING CANCER USING THE SAME

CROSS REFERENCE TO RELATED APPLICATION

This application claims the benefit of U.S. Provisional Application Ser. No. 62/322,295, filed Apr. 14, 2016, the disclosure of which is hereby incorporated by reference in its entirety, including all figures, tables and amino acid or nucleic acid sequences.

This invention was made with government support under GM109645 awarded by the National Institutes of Health. The government has certain rights in the invention.

The Sequence Listing for this application is labeled "222110-2300 Sequence Listing ST25" which was created on Jan. 11, 2019 and is 36,928 bytes. The entire content of the sequence listing is incorporated herein by reference in its entirety.

BACKGROUND OF THE INVENTION

Some cancers, most commonly breast, ovarian, prostate and pancreatic cancers, have mutations in genes that mediate homologous recombination DNA repair, such as BRCA1 or 2. These mutations are often inherited and therefore, such cancers occur in familially related patients. Due to the defect in homologous recombination DNA repair, the cancer cells in these cancers depend on other DNA repair pathways.

BRIEF SUMMARY OF THE INVENTION

The invention exploits the reliance of cancer cells having mutations in the genes that mediate homologous recombination DNA repair on other DNA repair pathways to treat these cancers (e.g., BRCA1 and/or BRCA2). The invention provides the use of an inhibitory RNA (iRNA) that mediates sequence-specific degradation of the mRNA encoding Poly (ADP-ribose) polymerase 1 (PARP1) as a novel therapeutic agent for treating cancer. Since normal cells can tolerate reductions in PARP1 activity, this approach does not have side effects. The iRNA can be a small inhibitory RNA (siRNA), microRNA (miRNA), short hairpin RNA (shRNA) or antisense-oligonucleotide. In one embodiment, the iRNA is an miRNA, preferably, miR-223, more preferably, miR-223-3p or a modified miR-223-3p having substitutions and/or deletions in miR-223-3p. Accordingly, the invention provides a pharmaceutical composition comprising the iRNA, preferably, an miRNA, more preferably, miR-223-3p or a modified miR-223-3p.

A method of treating cancers having mutations in the genes that mediate homologous recombination DNA repair are also provided. The method comprises administering the pharmaceutical composition of the invention to a subject in need thereof. The cancer can be breast cancer, ovarian cancer, prostate cancer, pancreatic cancer or mesothelioma. Methods of treating cancer using a combination of the iRNA of the invention and a second cancer therapeutic are also provided.

BRIEF DESCRIPTION OF THE DRAWINGS

FIG. 3. Endogenous levels of miR-223 in HL60 cells following 50 µM AraC. qRT-PCR of miR-223-3p: The levels of endogenous miR-223-3p decrease at different time points after treating the cells with 50 µM Ara-C. NT—non-treated (left). Western blot analysis showing inverse correlation of PARP1 protein with miR-223 at different time points after Ara-C treatment. Ara-C stalls replication forks, which collapses and generates one-sided DNA ends, requiring DNA repair. Thus, miR-223-3p levels decrease upon DNA damage, when PARP1 is required to promote DNA repair.

FIG. 6. Sequence alignment of Mir-223-3p (SEQ ID NO: 75) with 3' UTR of PARP1 mRNA (SEQ ID NO: 92).

FIG. 8. Novel gain of function mutations in mir-223-3p to improve its repression of PARP1. Each derivative will have the corresponding nucleotide alteration in 5p strand as well. Modifications are bolded and underlined. Deletions are indicated by "-".

FIG. 24A. Colony formation assay in Human Mesothelioma Cells-1 in the presence of different PARP1 inhibitors. FIG. 24B. Western blot analysis showing reduced expression of PARP1 in response to the inhibitors.

FIG. 25B).

FIGS. 27A-27B. HR defecient cells express repressed levels of miR223-3p. Endogenous levels of miR223 3p and 5p in HR deficient cells was compared to Jurkat cells. FIG. 27A depicts the relative fold change in expression and endogenous levels are shown in FIG. 27B.

FIG. 29D shows knockdown of PARP1 in a Western blot.

FIG. 31C illustrates the numbers of colonies formed when treated with olaparib.

FIGS. 32A-32C. Synthetic lethality in BAP1 mutant mesothelioma (colony formation assays (FIGS. 32A-32B) and knockdown of PARP1 by miR223-3p (FIG. 32C).

FIGS. 36A-36C. Decreased active replication forks in H2452 BAP1 mutant cells. FIGS. 36A-36B show representative images and percentage of active replication forks as measured by BrdU (assays as mentioned in FIG. 35). FIG. 36C shows PARP1 knockdown in the cells.

FIGS. 38A-38B. Measuring the levels of endogenous miR223-3p (qRT-PCR) in MCF7 cells after treating the cells with siRNA for BRCA1 (FIG. 38A). Western blots show BRCA1 knockdown (FIG. 38B).

FIG. 42A). Western blot showing inverse correlation of PARP1 protein with miR223-3p at different time points after Ara-C treatment (FIG. 42B).

DETAILED DISCLOSURE OF THE INVENTION

Figure 1:
FIG. 1. Colony Formation Survival Assay. BRCA1 mutant cancer cell lines MDA-MB-436 (breast cancer) and UWB1.289 (ovarian cancer), deficient in BRCA1 showed decreased number of colonies when cells were treated with 25 nm miR-223-3p mimic. * indicates p=0.009 and ** indicates p=0.000096.
Figure 2:
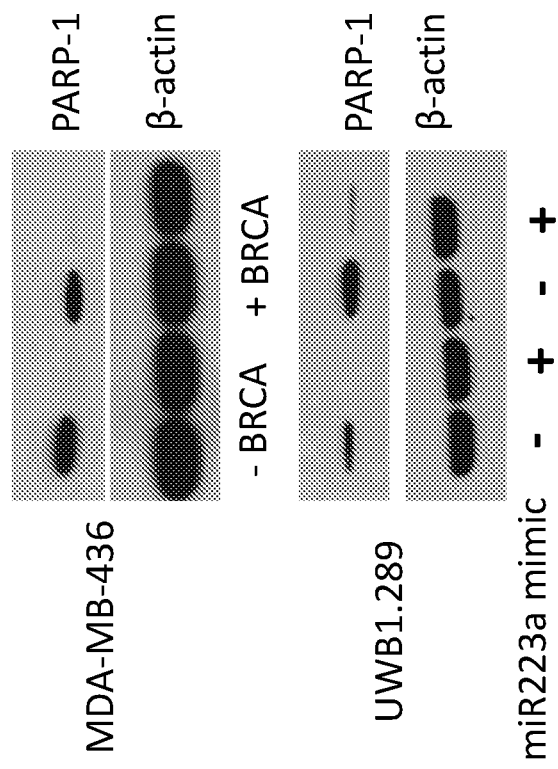
FIG. 2. Western analysis of PARP1 after exposure to miR-223-3p mimic. miR-223-3p represses PARP1 protein expression in the breast and ovarian cell lines harboring BRCA1 mutant.
Figure 4:
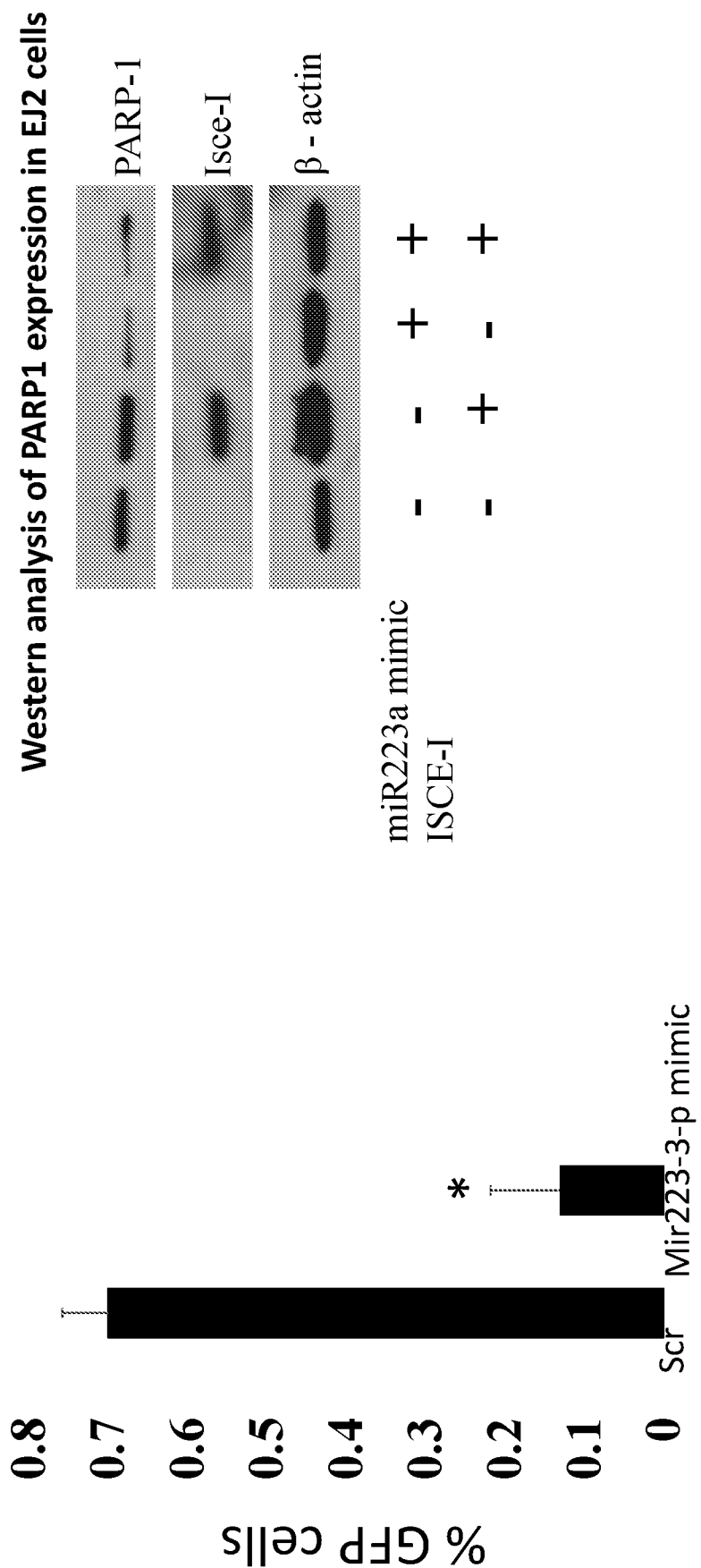
FIG. 4. Alternative Non-Homologous End Joining (aNHEJ) in EJ2-GFP cells. Mir223-3p blocks aNHEJ-aNHEJ is a salvage DNA repair pathway that requires PARP1. EJ2 cells express GFP upon productive aNHEJ repair (the assay is initiated with expression of transduced Isce-I). The fraction of EJ2 cells with productive aNHEJ is decreased with prior exposure to miR-223-3p (left). This pathway can lead to dangerous genomic rearrangements such as chromosomal translocations. Thus, many normal cells may express miR-223-3p to regulate this pathway.
Figure 5:
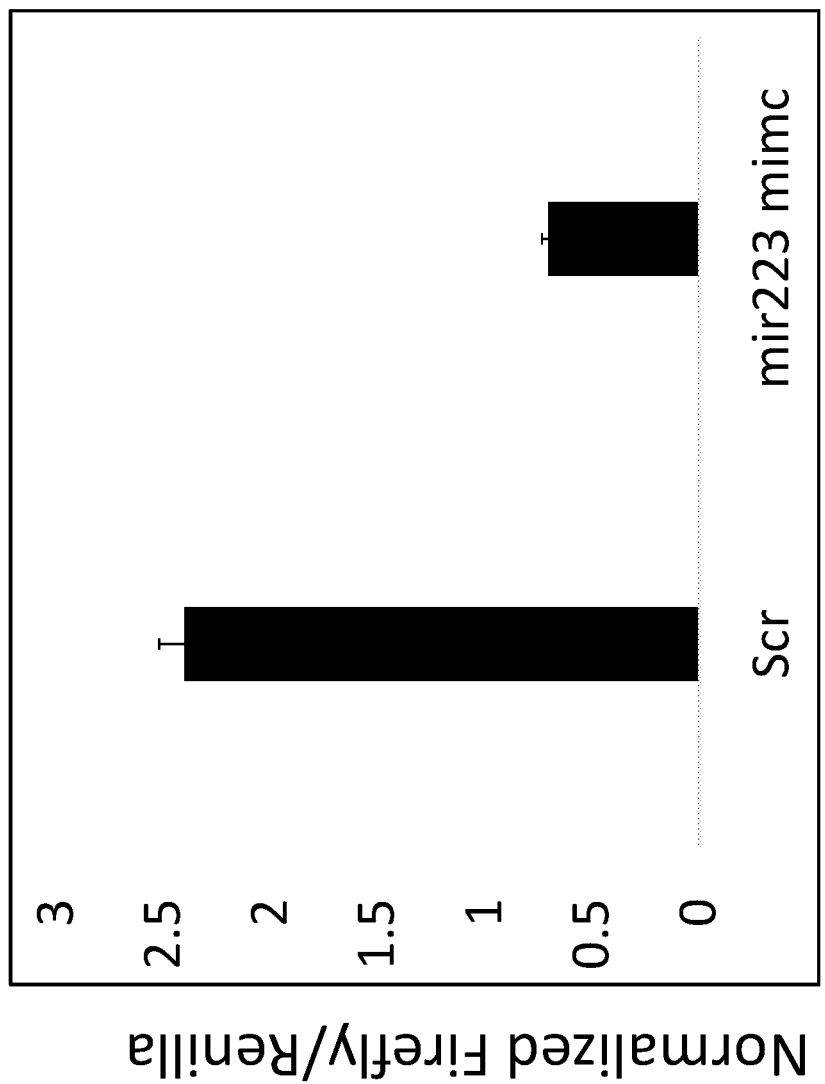
FIG. 5. Mir223a reduces PARP1 3' UTR mRNA levels—The 3' UTR of PARP1 mRNA (ENST0000036) was linked to Firefly Luciferase. When this RNA is present the cells will express Luciferase, but when miR-223-3p is present the Luciferase expression is decreased. This indicates that miR-223-3p binds to and mediates the destruction of PARP1 mRNA.
Figure 7:
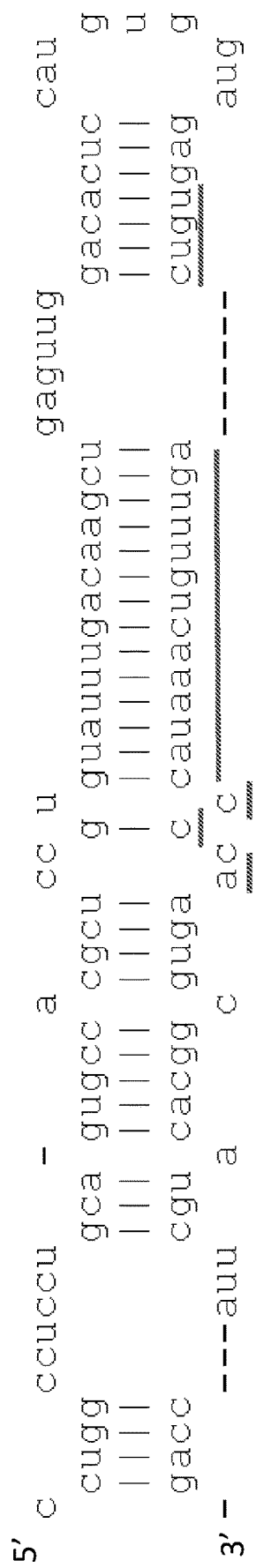
FIG. 7. Mature miR-223-3p underlined within the miR-223 pre-microRNA structure (SEQ ID NO:94).
Figure 9:
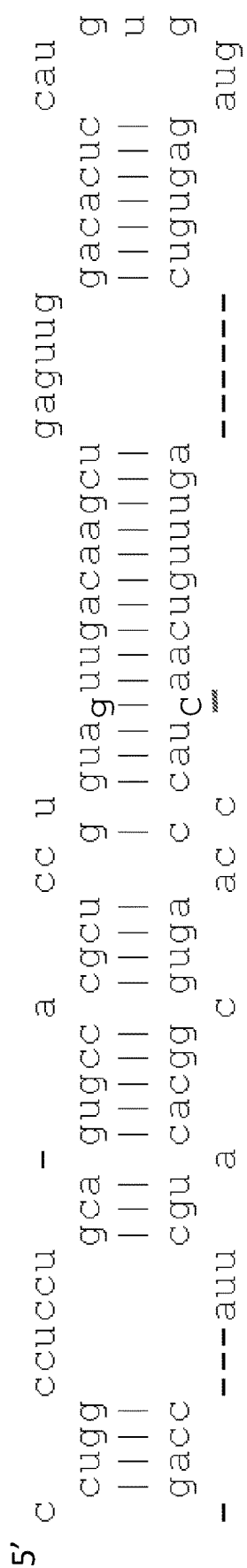
FIG. 9. Novel miR-223-3p derivative 1 (SEQ ID NO:95) having enhanced PARP1 repression. The substitutions and/or deletions are underlined.
Figure 10:
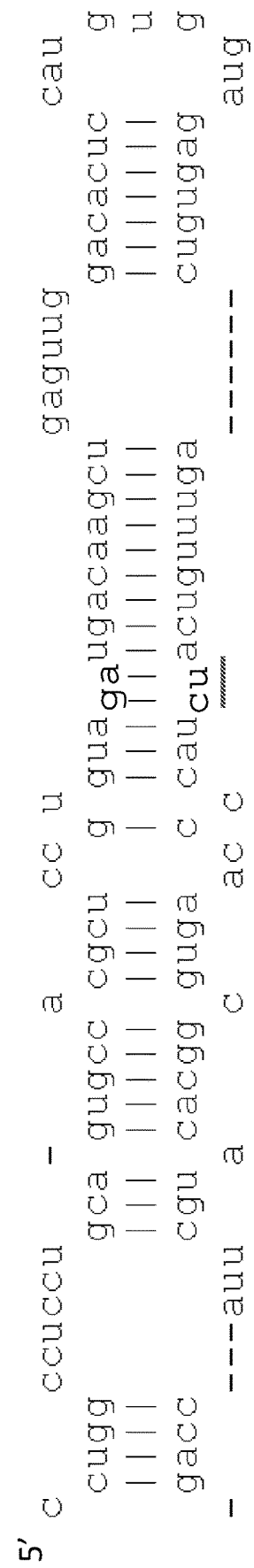
FIG. 10. Novel miR-223-3p derivative 2 (SEQ ID NO:96) having enhanced PARP1 repression. The substitutions and/or deletions are underlined.
Figure 11:
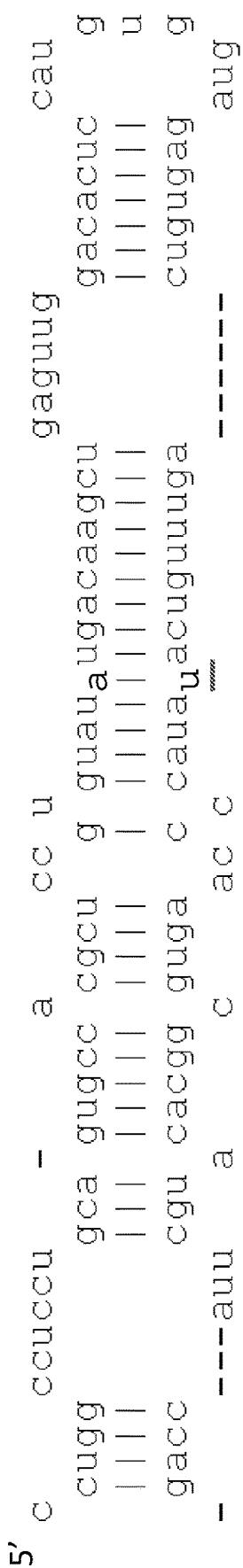
FIG. 11. Novel miR-223-3p derivative 3 (SEQ ID NO:97) having enhanced PARP1 repression. The substitutions and/or deletions are underlined.
Figure 12:
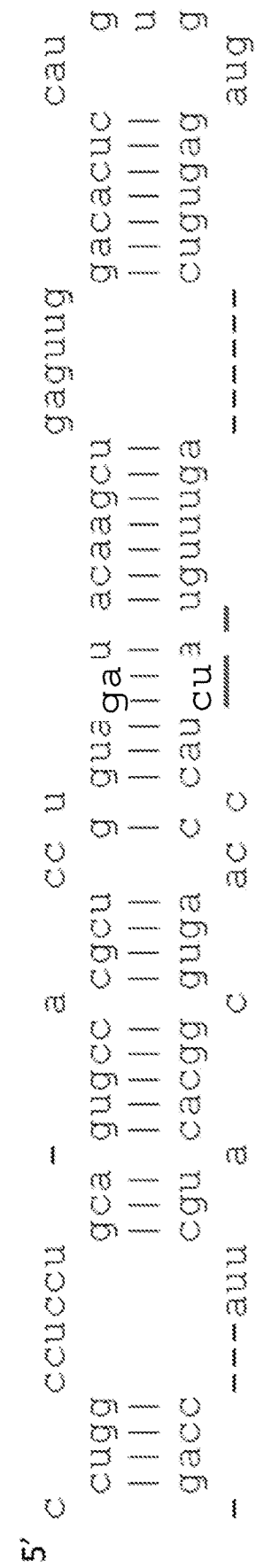
FIG. 12. Novel miR-223-3p derivative 4 (SEQ ID NO:98) having enhanced PARP1 repression. The substitutions and/or deletions are underlined.
Figure 13:
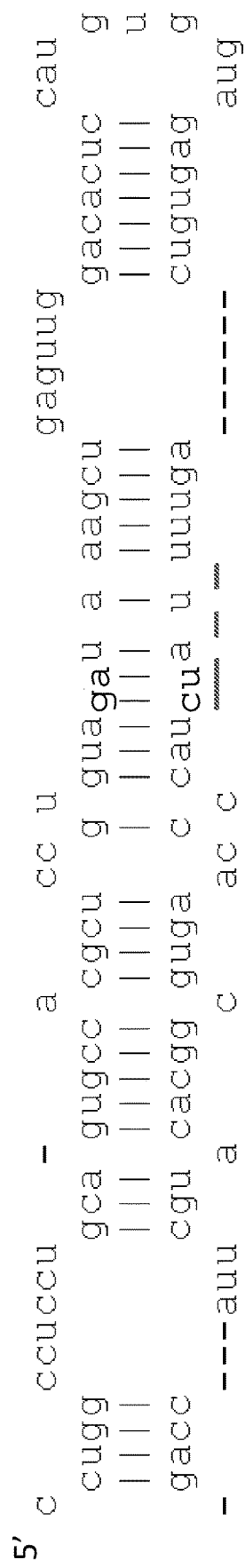
FIG. 13. Novel miR-223-3p derivative 5 (SEQ ID NO:99) having enhanced PARP1 repression. The substitutions and/or deletions are underlined.
Figure 14:
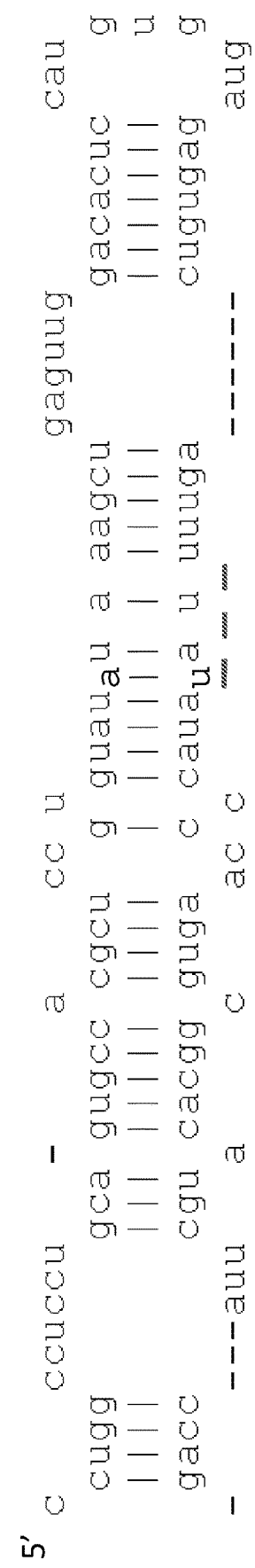
FIG. 14. Novel miR-223-3p derivative 6 (SEQ ID NO:100) having enhanced PARP1 repression. The substitutions and/or deletions are underlined.
Figure 15:
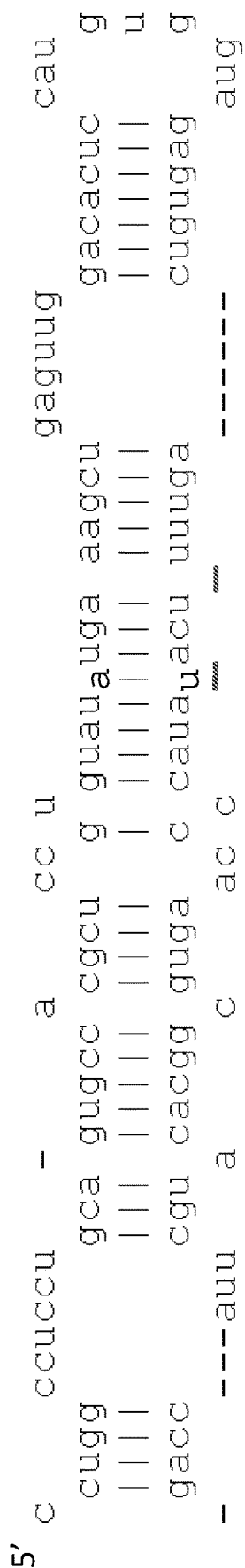
FIG. 15. Novel miR-223-3p derivative 7 (SEQ ID NO:101) having enhanced PARP1 repression. The substitutions and/or deletions are underlined.
Figure 16:
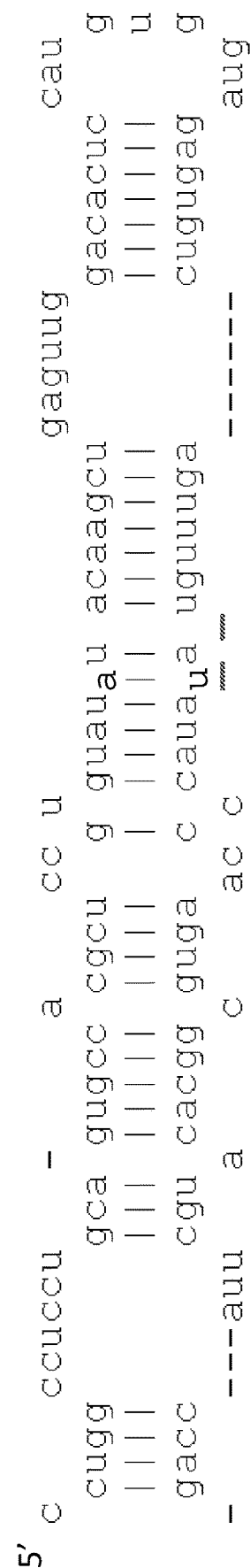
FIG. 16. Novel miR-223-3p derivative 8 (SEQ ID NO:102) having enhanced PARP1 repression. The substitutions and/or deletions are underlined.
Figures 17, 18:
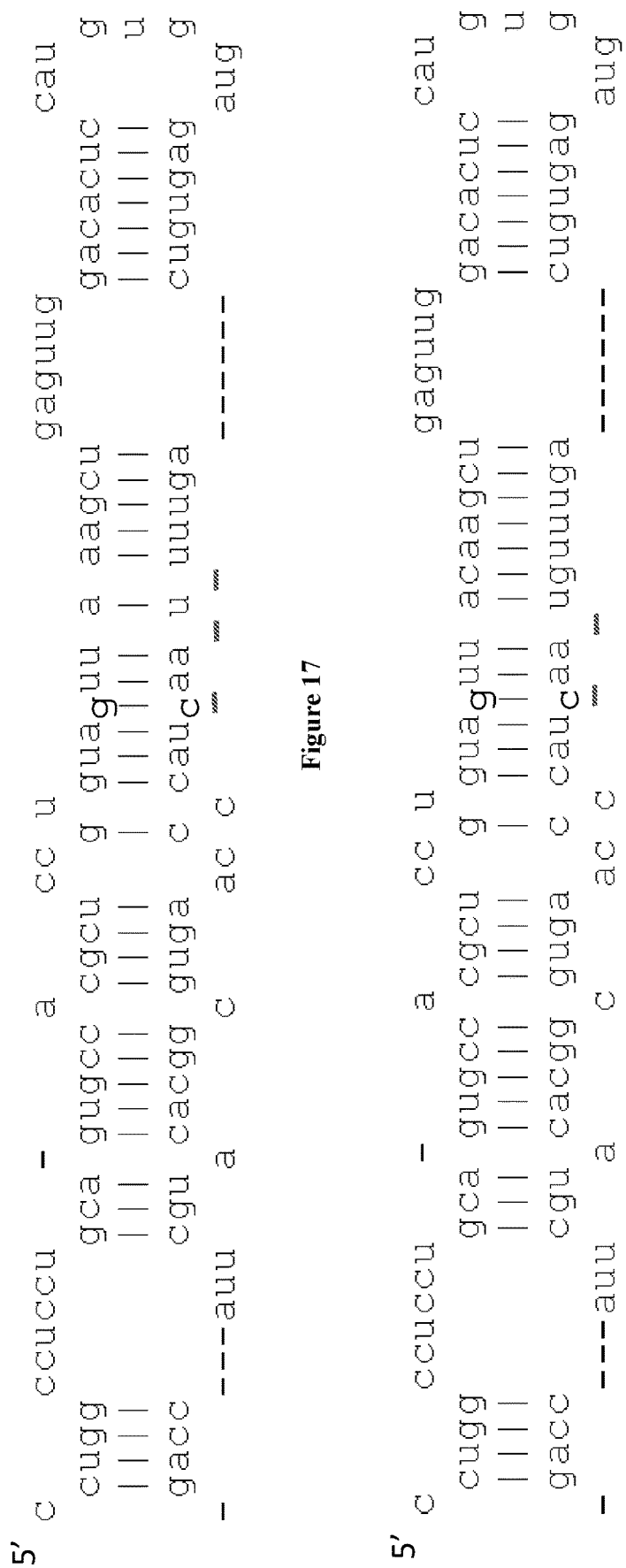
FIG. 17. Novel miR-223-3p derivative 9 (SEQ ID NO:103) having enhanced PARP1 repression. The substitutions and/or deletions are underlined.
FIG. 18. Novel miR-223-3p derivative 10 (SEQ ID NO:104) having enhanced PARP1 repression. The substitutions and/or deletions are underlined.
Figure 19:
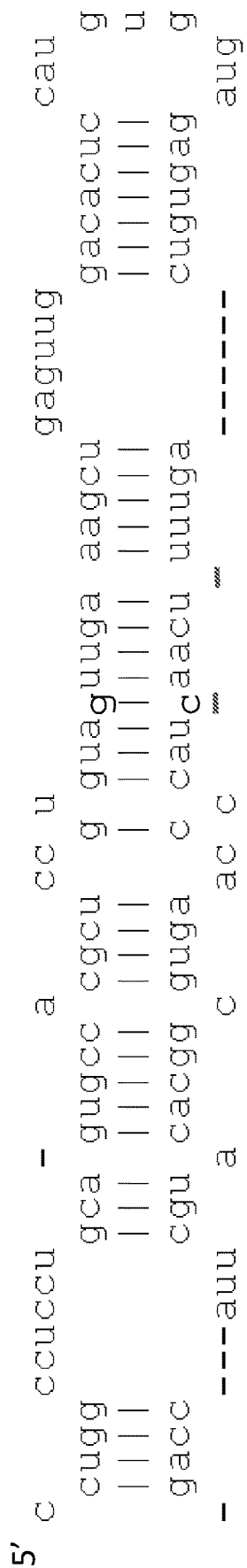
FIG. 19. Novel miR-223-3p derivative 11 (SEQ ID NO:105) having enhanced PARP1 repression. The substitutions and/or deletions are underlined.
Figure 20:
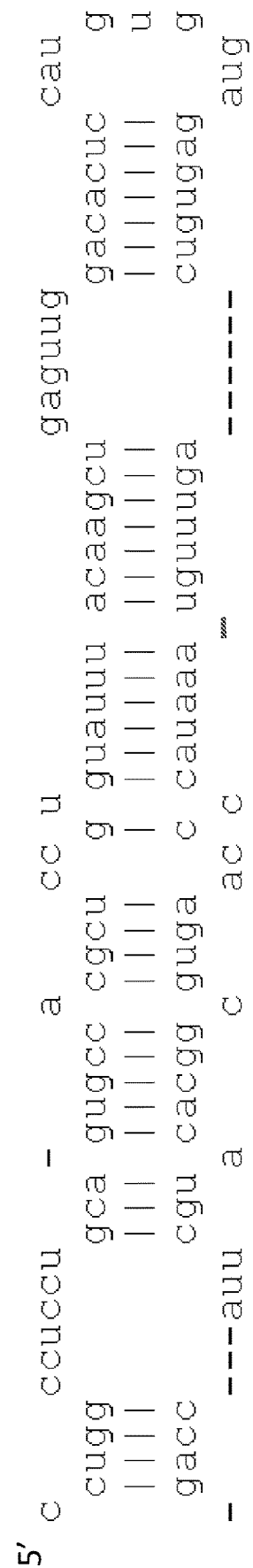
FIG. 20. Novel miR-223-3p derivative 12 (SEQ ID NO:106) having enhanced PARP1 repression. The substitutions and/or deletions are underlined.
Figure 21:
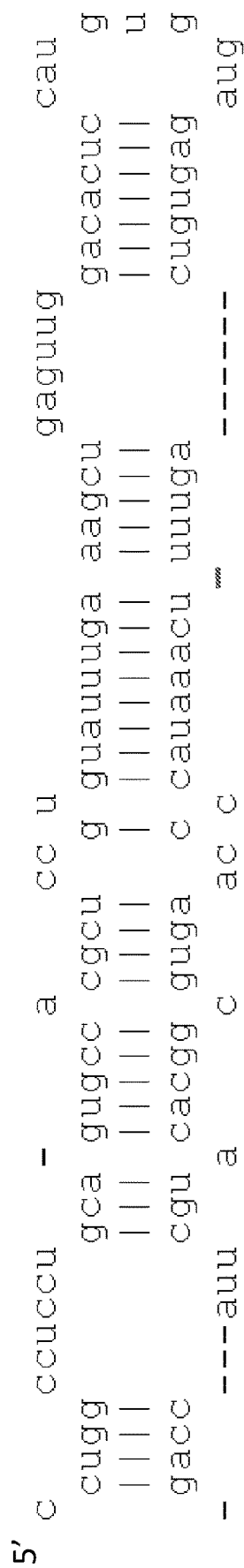
FIG. 21. Novel miR-223-3p derivative 13 (SEQ ID NO:107) having enhanced PARP1 repression. The substitutions and/or deletions are underlined.
Figure 22:
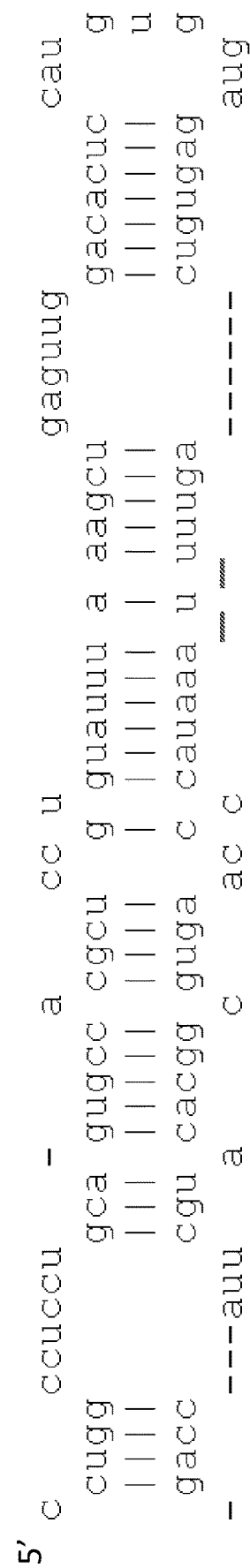
FIG. 22. Novel miR-223-3p derivative 14 (SEQ ID NO:108) having enhanced PARP1 repression. The substitutions and/or deletions are underlined.
Figure 23:
FIG. 23. Human mesothelioma cells treated with 3 µM olaparib for 10 days. The graph shows the average from 3 independent experiments each done in triplicates.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with cancer such that an improvement is observed in the patient, notwithstanding that the patient may still be afflicted with cancer.

As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of: (1) benign or malignant cells (e.g., tumor cells) that correlates with overexpression of a serine/threonine kinase; or (2) benign or malignant cells (e.g., tumor cells) that correlates with abnormally high levels of serine/threonine kinase activity or lipid kinase activity. Non-limiting serine/threonine kinases implicated in cancer include but are not limited to PI-3K mTOR, and AKT. Exemplary lipid kinases include but are not limited to PI3 kinases such as PBKα, PBKβ, PBKδ, and PBKγ.

The term "effective amount" or "therapeutically effective amount" refers to that amount of a pharmaceutical described herein that is sufficient to effect the intended application including but not limited to cancer treatment. The therapeutically effective amount may vary depending upon the intended application, the subject and cancer being treated, e.g., the weight and age of the subject, the type and severity of cancer, the manner of administration and the like. A therapeutically effective amount can be readily determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

A "sub-therapeutic amount" of an agent is an amount less than the effective amount for that agent, but which when combined with an effective or sub-therapeutic amount of another agent or therapy can produce a desired result, due to, for example, synergy in the resulting efficacious effects (e.g., therapeutic benefit) for the patient, or reduced side effects associated with the compounds administered to the patient. Typical therapeutic amounts for an agent, as disclosed herein, can be ascertained from various publicly available sources (e.g., drugs.com, The Physician's Desk Reference, or scientific literature). Sub-therapeutic amounts of an agent, as provided herein, are amounts less than those reported in the publicly available sources for treatment of a particular cancer. Sub-therapeutic amounts of an therapeutic agent are, therefore, between about 10%-75%, about 20-50%, about 35-65%, about 40-60%, about 45-55% or about 50% of the standard therapeutic amount of a given therapeutic agent.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the pharmaceutical compositions described herein, its use in the compositions of the invention is contemplated.

A "subject" refers to an animal, such as a mammal, for example a human. The methods described herein can be useful in both humans and non-human animals. In some embodiments, the subject is a mammal, such as an animal model of disease, for example, a rodent, cattle, pig, rabbit, dog or cat and in some embodiments, the subject is a human. The terms "subject" and "patient" can be used interchangeably.

The terms "co-administration," "administered in combination with," and their grammatical equivalents encompass administration of two or more therapeutics to a subject so that both agents and/or their metabolites are present in the subject at the same time. Co-administration includes simultaneous administration in separate compositions, administration at different times in separate compositions, or administration in a composition in which both pharmaceutics are present.

Accordingly, an embodiment of the invention provides a pharmaceutical composition comprising an iRNA that mediates sequence-specific degradation of an mRNA encoding PARP1. In one embodiment, the subject being treated is a human and the mRNA encoding PARP1 has the sequence of SEQ ID NO: 1; whereas, the sequence of PARP1 protein has the sequence of SEQ ID NO: 2. The sequences of the mRNAs encoding PARP1 protein in other mammals are publically available, for example, in NCBI and other sequence databases, and such embodiments are within the purview of the invention.

In one embodiment, the iRNA is an siRNA. The siRNA can have the combinations of antisense and sense strand sequences as shown in Table 1 below. In one embodiment, the siRNA has 3' overhang of one or more nucleotides, preferably, one or two deoxythymidines. In another embodiment, the siRNA is chemically modified in a manner that decreases the susceptibility of nucleic acids to nuclease degradation and/or reduces an innate immune response to the siRNA. Non-limiting examples of such chemical modifications include 2'-deoxy, 2'-O-methyl, 2'-fluoro, 2'-methoxyethyl, or 2'-aminoethyl modifications, such as those disclosed in U.S. Pat. No. 9,222,092 which is hereby incorporated by reference in its entirety.

TABLE 1 siRNAs that mediate degradation of an mRNA of SEQ ID NO: 1.

| siRNA ID | Sense strand sequence | SEQ ID NO: | Antisense strand sequence | SEQ ID NO: |
| --- | --- | --- | --- | --- |
| siRNA-1 | CCUCAUCAAGAUGAUCUUU | 3 | AAAGAUCAUCUUGAUGAGG | 4 |
| siRNA-2 | GAUGAUCUUUGAUGUGGAA | 5 | UUCCACAUCAAAGAUCAUC | 6 |
| siRNA-3 | GAUCCUGGAUCUCUCAAAU | 7 | AUUUGAGAGAUCCAGGAUC | 8 |
| siRNA-4 | GCAAGGAUCCCAUCGAUGU | 9 | ACAUCGAUGGGAUCCUUGC | 10 |
| siRNA-5 | UCCCAUCGAUGUCAACUAU | 11 | AUAGUUGACAUCGAUGGGA | 12 |
| siRNA-6 | GGUGGUUGACAGAGAUUCU | 13 | AGAAUCUCUGUCAACCACC | 14 |
| siRNA-7 | GCCGAGAUCAUCAGGAAGU | 15 | ACUUCCUGAUGAUCUCGGC | 16 |
| siRNA-8 | GCCCUUUAAGCAGCUUCAU | 17 | AUGAAGCUGCUUAAAGGGC | 18 |

TABLE 1-continued siRNAs that mediate degradation of an mRNA of SEQ ID NO: 1.

| siRNA ID | Sense strand sequence | SEQ ID NO: | Antisense strand sequence | SEQ ID NO: |
|---|---|---|---|---|
| siRNA-9 | CCACCAACUUUGCUGGGAU | 19 | AUCCCAGCAAAGUUGGUGG | 20 |
| siRNA-10 | CCAACUUUGCUGGGAUCCU | 21 | AGGAUCCCAGCAAAGUUGG | 22 |
| siRNA-11 | GGAGUAUGAGAUCGACCUU | 23 | AAGGUCGAUCUCAUACUCC | 24 |
| siRNA-12 | GGUCUGAUGAUAGCAGCAA | 25 | UUGCUGCUAUCAUCAGACC | 26 |
| siRNA-13 | GCGUAUGACUUGGAAGUCA | 27 | UGACUUCCAAGUCAUACGC | 28 |
| siRNA-14 | GGAAGUCAUCGAUAUCUUU | 29 | AAAGAUAUCGAUGACUUCC | 30 |
| siRNA-15 | GCGAAUGCCAGCGUUACAA | 31 | UUGUAACGCUGGCAUUCGC | 32 |
| siRNA-16 | CCAGCGUUACAAGCCCUUU | 33 | AAAGGGCUUGUAACGCUGG | 34 |
| siRNA-17 | CCUUUAAGCAGCUUCAUAA | 35 | UUAUGAAGCUGCUUAAAGG | 36 |
| siRNA-18 | GGAUCUAUUUCGCUGACAU | 37 | AUGUCAGCGAAAUAGAUCC | 38 |
| siRNA-19 | GGAGUCUUCGGAUAAGCUCUA | 39 | UAGAGCUUAUCCGAAGACUCC | 40 |
| siRNA-20 | GAACAUCAAGGACGAGCUAAA | 41 | UUUAGCUCGUCCUUGAUGUUC | 42 |
| siRNA-21 | GGUCAAGGAGGAAGGUAUCAA | 43 | UUGAUACCUUCCUCCUUGACC | 44 |
| siRNA-22 | GGUGAUCGGUAGCAACAAACU | 45 | AGUUUGUUGCUACCGAUCACC | 46 |
| siRNA-23 | GCAGUGAAGAAGCUGACAGUA | 47 | UACUGUCAGCUUCUUCACUGC | 48 |
| siRNA-24 | GGAAGUCAUCGAUAUCUUUAA | 49 | UUAAAGAUAUCGAUGACUUCC | 50 |
| siRNA-25 | GUGCCAACUACUGCCAUACGU | 51 | ACGUAUGGCAGUAGUUGGCAC | 52 |

In another embodiment, the iRNA is an shRNA. An shRNA can have the combinations of antisense and sense sequences as shown in Table 2 below. A person of ordinary skill in the art can design an shRNA based on the antisense and sense strand sequences as provided below, for example, by adding appropriate loop sequences between the sense and the anti-sense sequences. In one embodiment, an shRNA is encoded by a vector containing the shRNA encoding sequence. Methods of designing shRNA and vectors containing shRNA encoding sequences are well known to a person of ordinary skill in the art and such embodiments are within the purview of the invention.

TABLE 2 shRNAs that mediate degradation of an mRNA of SEQ ID NO: 1.

| shRNA ID | Sense strand sequence | SEQ ID NO: | Antisense strand sequence | SEQ ID NO: |
|---|---|---|---|---|
| shRNA-1 | GGAGUAUGAGAUCGACCUUCA | 53 | UGAAGGUCGAUCUCAUACUCC | 54 |
| shRNA-2 | GCUCCUGAACAAUGCAGACAG | 55 | CUGUCUGCAUUGUUCAGGAGC | 56 |
| shRNA-3 | GGUCUGAUGAUAGCAGCAAGG | 57 | CCUUGCUGCUAUCAUCAGACC | 58 |
| shRNA-4 | GCAAGGAUCCCAUCGAUGUCA | 59 | UGACAUCGAUGGGAUCCUUGC | 60 |
| shRNA-5 | GCAACCACACACAAUGCGUAU | 61 | AUACGCAUUGUGUGUGGUUGC | 62 |
| shRNA-6 | GCGUAUGACUUGGAAGUCAUC | 63 | GAUGACUUCCAAGUCAUACGC | 64 |
| shRNA-7 | GCCAGCGUUACAAGCCCUUUA | 65 | UAAAGGGCUUGUAACGCUGGC | 66 |
| shRNA-8 | GCCCUUUAAGCAGCUUCAUAA | 67 | UUAUGAAGCUGCUUAAAGGGC | 68 |
| shRNA-9 | GGAUCUAUUUCGCUGACAUGG | 69 | CCAUGUCAGCGAAAUAGAUCC | 70 |
| shRNA-10 | GCCAACUACUGCCAUACGUCU | 71 | AGACGUAUGGCAGUAGUUGGC | 72 |

In a further embodiment, the iRNA is an antisense oligonucleotide. An antisense oligonucleotide can have the sequences as shown in Tables 1 and 2 for the antisense strands. An antisense oligonucleotide can be chemically modified in a manner that decreases the susceptibility of nucleic acids to nuclease degradation. Non-limiting examples of chemical modifications to antisense oligonucleotide include adding phosphorothionate, methyl phosphonate or phosphoramidate moieties.

In one embodiment, the iRNA is an miRNA, preferably, miR-223, even more preferably, miR-233-3p. The sequence of pre-miR-223 is SEQ ID NO: 73; whereas, the sequence of miR-223-5p is SEQ ID NO: 74 and the sequence of miR-223-3p is SEQ ID NO: 75. In another embodiment, miR-223-3p is modified where one or more nucleotides of miR-223-3p are substituted or deleted. In certain examples, the modified miR-223-3p has the sequence selected from SEQ ID NOs: 76 to 89 and 93 and are illustrated in FIG. 8. In another example, the modified mir223-3p sequence is SEQ ID NO: 93, and illustrated in FIG. 44. In a further embodiment, the miRNA is chemically modified in a manner that decreases the susceptibility to nuclease degradation. Non-limiting examples of modifications to the miRNAs include uridylation, adenylation, 2'-deoxy modification, 2'-O-methylation, 2'-fluorination, 2'-methoxyethylation, 2'-aminoethylation or adding phosphorothionate, methyl phosphonate or phosphoramidate moieties.

In an embodiment, the iRNA molecules are conjugated to a carrier at the 5' or 3' end of the iRNA. The carrier can be a molecule that decreases clearance in a subject's body, for example, polymers, such as dextrans or PEG. The carrier can also be a molecule that enhance cellular uptake of the iRNA conjugated thereto, for example, transferrin or lipophilic molecules that enhance cellular uptake, such as cholesterol, short chain fatty acids, single or double chain fatty acids or folates. Further, the carrier can be a targeting molecule, such as antibodies, polypeptides, nucleic acids and other substances that direct the iRNA to selected target cells.

Furthermore, the carrier is a molecule that facilitates endocytosis of the iRNA. Non-limiting examples of carriers that facilitate endocytosis include single or double chain fatty acids, tocopherol, folates or folic acid, cholesterol, sugars such as galactose and mannose and their oligosaccharides, peptides such as RGD and bombesin, and proteins such as integrin. Non-limiting examples of molecules for improving endocytosis for use in pharmaceutical composition are described in the U.S. Patent Application Publication US2008/0194540.

Fatty acids may be saturated or unsaturated and be in $C_4$-$C_{28}$, preferably in $C_{14}$-$C_{22}$, still more preferably in $C_{18}$ such as oleic acid or stearic acid. Fatty acids can also be octadecyl or dioleoyl. Fatty acids can be found in double chain form linked with an linker such as a glycerol, a phosphatidylcholine or ethanolamine.

As used herein, the term "folate" refers to folate and folate derivatives, including pteroic acid derivatives and analogs. The analogs and derivatives of folic acid suitable for use in the invention include, antifolates, dihydrofolates, tetrahydrofolates, folinic acid, pteropolyglutamic acid, 1-deza, 3-deaza, 5-deaza, 8-deaza, 10-deaza, 1,5-deaza, 5,10-dideaza, 8,10-dideaza, and 5,8-dideaza folates, antifolates, and pteroic acid derivatives. Additional folate analogs are described in the U.S. Patent Application Publication US2004/242582.

Additional examples of chemical modifications that increase siRNA, shRNA, antisense and miRNA stability are well known to a person of ordinary skill in the art and such embodiments are within the purview of the invention. For example, the iRNA disclosed herein can contain an "end modification" which means a chemical entity is added to the most 5' and/or 3' nucleotide. Examples of such end modifications include, but are not limited to, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 B1. As used herein, alkyl or any term comprising "alkyl" means any carbon atom chain comprising 1 to 12, preferably 1 to 6 and more, preferably 1 to 2 C atoms. A further end modification is the addition of a biotin group to the iRNA, which may preferably be attached to either the most 5' or the most 3' nucleotide or to both ends. Such a modification permits the attachment of the iRNA molecule to a polypeptide, protein or other targeting agent/substrate via avidin or streptavidin binding to the polypeptide, protein or other targeting agent.

Yet other modifications to the iRNAs disclosed herein include modification of at least one nucleotide of the iRNA at the 2'-position of nucleotides's ribose moiety. Modification of the ribose moiety is, preferably, with a substituent selected from the group consisting of an amino, fluoro, methoxy, alkoxy and alkyl group. As used herein, alkyl or any term comprising "alkyl" means any carbon atom chain comprising 1 to 12, preferably 1 to 6 and more, preferably 1 to 2 C atoms.

The disclosed iRNA molecules can also contain patterns of modifications. For example, a contiguous stretch of nucleotides can contain modifications within a single nucleotide or group of nucleotides that are covalently linked to each other via standard phosphodiester bonds or, at least partially, through phosphorothioate bonds. In the event that such a modified nucleotide or group of modified nucleotides does not form the 5'-end or 3'-end of the stretch, a flanking nucleotide or group of nucleotides may be arrayed on one or both sides of the modified nucleotide or group, where the flanking nucleotide or group either is unmodified or is modified and does not have the same modification as the preceding nucleotide or group of nucleotides. This sequence of modified nucleotide or group of modified nucleotides, respectively, and unmodified or differently modified nucleotide or group of unmodified or differently modified nucleotides may be repeated one or more times or groups of modified nucleotides can be flanked by groups of differently modified or unmodified nucleotides. The groups of modified, unmodified or differently modified nucleotides can number between one (1) and ten (10) nucleotides. The term "unmodified nucleotide" as used herein means either not having any of the aforementioned modifications at the nucleotide forming the respective nucleotide or group of nucleotides. Modifications, such as those disclosed in U.S. Pat. No. 9,222,092, which is hereby incorporated by reference in its entirety, can also be made to the iRNA disclosed herein.

In one embodiment, the iRNAs of the claimed invention, for example, the siRNAs, shRNAs, antisense oligonucleotides or miRNAs described above, are in a pharmaceutical composition, wherein the pharmaceutical composition comprises liposomes containing the iRNAs, microspheres containing the iRNAs or serum albumin complexes containing the iRNAs.

Liposomes are made of phospholipid molecules capable of encapsulating the iRNAs of the invention within the liposome aqueous core. Liposomes can be designed to protect the iRNAs in vivo. Liposomes can also be modified to enhance the delivery of iRNAs into specific target cells. For example, liposomes can be modified to contain binding agents, for example, binding proteins, antibodies or fragments of antibodies, that specifically bind to biomolecules, for example, cell surface receptors, that are specifically present on the surface of the cancer cells or that are present on the surface of the cancer cells at a higher level compared to non-target cells. Certain examples of using specific cell surface biomolecules present on the surface of the cancer cells and corresponding binding agents that can be incorporated in liposomes are described in Deshpande et al., the contents of which are herein incorporated by reference in their entirety. Additional examples of cell surface biomolecules specifically present or overexpressed on the surface of the cancer cells are known to a person of ordinary skill in the art and such embodiments are within the purview of the claimed invention. Liposomes can be administered topically, orally, or via pulmonary or parenteral routes.

Various liposome compositions are known to a person of ordinary skill in the art. For example, Maherani et al. (2011) describes manufacturing techniques for liposomes, composition of liposomes, methods of encapsulating biomolecules into liposomes, and methods of producing pharmaceutical compositions comprising liposomes. The Maherani et al. reference is herein incorporated by reference in its entirety.

In one embodiment, the liposomes contain agents that destabilize the liposome membrane and cause the release of contents in the aqueous compartment into the target cells. The destabilizing agents can destabilize the liposomes in response to a lower pH, for example, lower pH present in endosomes/lysosome compartments of the target cells. In certain embodiments, temperature sensitive or radiation sensitive destabilizers are used where the cancer cells, for example, in a tumor, can be subjected to conditions that cause release of the contents of the liposomes into the target cells.

In one embodiment, the invention provides pharmaceutical compositions comprising microspheres containing the iRNA described herein. In a specific embodiment, the microspheres are ephrin-A1 loaded microspheres, particularly, ephrinA1-loaded albumin microspheres. Lee et al. (2011) describe ephrinA1-loaded albumin microspheres. The Lee et al. reference is herein incorporated in its entirety.

In another embodiment, the pharmaceutical composition of the invention comprises the iRNA of the invention, particularly, miR-223, and more particularly, miR-223-3p or a modified miR-223-3p, complexed with serum albumin.

Certain examples of serum albumin complexed with an iRNA in a pharmaceutical composition are provided in Nicoli et al. and U.S. Pat. No. 8,513,402. Nicoli et al. and the U.S. Pat. No. 8,513,402 are herein incorporated by reference in their entirety. Additional techniques of using serum albumin complexed with an iRNA in a pharmaceutical composition are well known to a person of ordinary skill in the art and such embodiments are within the purview of the invention.

A further embodiment of the invention provides a method of treating cancer, the method comprising administering the pharmaceutical composition described herein to a subject in need thereof. In a particular embodiment, the cancer cells of the subject comprise a mutation in one or more genes that mediate the homologous recombination DNA repair, for example, BRCA1 and/or BRCA2 genes. In additional embodiments, the cancer cells of the subject comprise a loss of function via a mutation or epigenetic silencing in one or more genes that mediate the homologous recombination DNA repair, for example, the genes provided in Table 3:

TABLE 3

Genes that mediate the homologous recombination DNA repair and cancers associated with the mutation, repression or deficiency of these genes that can be treated according to the invention.

| Acronym | Full-name | Associated cancers |
| --- | --- | --- |
| BAP1 | BRCA1 associated protein-1 | melanoma, renal cell carcinoma, non-small cell lung cancer, cholangiocarcinoma, mesothelioma, malignant mesothelioma, uveal melanoma and cutaneous melanoma |
| RAD51 and its paralogues A, B and C | RAD51 recombinase | breast, ovarian, and uterine cancer and acute myeloid leukemia, acute lymphoid leukemia, non-Hodgkin's lymphoma, and chronic lymphocytic leukemia |
| MMSET (NSD2) | multiple myeloma SET domain or Nuclear SET Domain-Containing Protein 2 | Myeloma, acute myeloid and lymphoid leukemia |
| ATM | Ataxia Telangiectasia Mutated | Myeloma, acute myeloid and lymphoid leukemia |
| ATR | Ataxia Telangiectasia And Rad3-Related Protein | endometrial, gastric cancers |
| CHEK2 | Checkpoint Kinase 2 | Breast cancer, sarcoma, brain tumor, prostate cancer, colorectal cancer |
| ERCC (1, 2, 3, 4 or 5) | Excision Repair Cross-Complementation Group (1, 2, 3, 4 or 5) | skin basal cell cancer; skin squamous cell cancer; melanoma, skin cancer |
| NBN (NBS1) | Nijmegen Breakage Syndrome 1 | NHL, glioma, medulloblastoma, rhabdomyosarcoma, breast-ovarian cancer |
| PALB2 | Partner And Localizer Of BRCA2 | Wilms tumour, medulloblastoma, AML, breast cancer, pancreatic cancer |
| BACH | Basic Region Leucine Zipper Transcriptional Regulator BACH | Breast cancer |

TABLE 3-continued

Genes that mediate the homologous recombination DNA repair and cancers associated with the mutation, repression or deficiency of these genes that can be treated according to the invention.

| Acronym | Full-name | Associated cancers |
| --- | --- | --- |
| SMARCA4 | SWI/SNF Related, Matrix Associated, Actin Dependent Regulator Of Chromatin, Subfamily A, Member 4 | non-small cell and small cell lung cancer, breast cancer, meningioma, glioma, prostate cancer |
| SMARCB1 | SWI/SNF Related, Matrix Associated, Actin Dependent Regulator Of Chromatin, Subfamily B, Member 1 | non-small cell and small cell lung cancer, breast cancer, meningioma, glioma, carcinoma, medulloblastoma, choroid plexus carcinoma, central primitive neuroectodermal tumors, renal or extra-renal malignant Rhabdoid tumors, non-vestibular schwannomas |
| SMARCD1 | SWI/SNF Related, Matrix Associated, Actin Dependent Regulator Of Chromatin, Subfamily D, Member 1 | non-small cell and small cell lung cancer, breast cancer, meningioma, glioma, prostate cancer |
| SMARCE1 | SWI/SNF Related, Matrix Associated, Actin Dependent Regulator Of Chromatin, Subfamily E, Member 1 | non-small cell and small cell lung cancer, breast cancer, meningioma, glioma, multiple meningioma, clear cell meningioma |
| WRN | Werner Syndrome, RecQ Helicase-Like | Osteosarcoma, meningioma, pancreatic cancer, colorectal cancer, adenoma, invasive adenocarcinoma |
| BLM | Bloom Syndrome, RecQ Helicase-Like | Breast cancer, ovarian cancer, uterine cancer, acute myeloid leukemia, acute lymphoid leukemia, chronic lymphocytic leukemia, gliomas, medulloblastomas, basal cell carcinomas, pancreatic cancer, skin cancer, colorectal cancer |
| EEPD1 | Endonuclease/Exonuclease/Phosphatase Family Domain Containing 1 | colon, lung, breast cancers, and non-Hodgkin's lymphoma |

Also contemplated by this disclosure is the treatment of cancers containing functional BRCA1 and/or BRCA2 DNA repair systems. In the case of such cancers, the methods contemplate the inactivation of the BRCA1 and/or BRCA2 DNA repair systems by interfering with BRCA1 and/or BRCA2 expression (e.g. via the use of iRNA (e.g., siRNA, antisense or shRNA) to downregulate or suppress expression of BRCA1 and/or BRCA2). The BRCA1 and BRCA2 iRNA can be co-administered with the PARP1 iRNA disclosed herein in order to mediate a therapeutic effect. Additional examples of the proteins involved in the homologous recombination DNA repair are well known to a person of ordinary skill in the art and such embodiments are within the purview of the claimed invention.

For the purpose of this invention, the phrase "a cancer cell comprises a mutation in one or more genes that mediate the homologous recombination DNA repair" indicates that the cancer cell contains one or mutations in one or more genes that encode for proteins that mediate the homologous recombination DNA repair and where the mutations in the genes affect the function of the encoding proteins such that the homologous recombination DNA repair does not function or functions at a lower efficiency when compared to a wild-type cell.

In some embodiments, the cancer is selected from breast cancer, ovarian cancer, prostate cancer, pancreatic cancer, lung cancer, small cell lung cancer, non-small cell lung cancer, cholangiocarcinoma, renal cell carcinoma or mesothelioma in which the BRCA1, BRCA2 and/or BAP1 genes are inactive due to mutations within the genes. In specific embodiments, miR223-3p can be used for intraperitoneal or intravenous chemotherapy of homologous recombination (HR)-deficient ovarian cancer, intravenous chemotherapy of HR-deficient breast cancer, intravenous chemotherapy of IDH1-mutant acute leukemia and glioblastoma (the IDH1 mutation represses HR DNA repair, making cancer sensitive to PARP1 inhibition), intravenous or intra-pleural chemotherapy of BAP1-mutant mesothelioma, or intravenous chemotherapy of BAP1-mutant melanoma, BAP1-mutant cholangiocarcinoma, and BAP1-mutant renal cell carcinoma (the BAP-1 mutation represses HR DNA repair, making cancer sensitive to PARP1 inhibition). In an embodiment, the method of treating cancer in a subject comprises administering to the subject the iRNA of the invention, for example, miR-223, miR-223-3p or a modified miR-223-3p described herein, wherein the method further comprises administering a second cancer therapy to the subject. The second cancer therapy can be selected from radiotherapy, chemotherapy, surgery, immunotherapy, monoclonal antibody therapy (e.g., bevacizumab or cetuximab) or a combination thereof.

In one embodiment, the second therapy is designed to induce DNA damage in the cell which increases the need of a cancer cell for DNA damage repair and consequently, increases the dependence of the cell on PARP1 in a cell that has a defective homologous recombination DNA repair. As such, in one embodiment, the iRNA of the invention, for example, miR-223, miR-223-3p or a modified miR-223-3p described herein, is administered in combination with the second therapy that induce DNA damage in the cell. In a particular embodiment, either or both of the iRNA of the invention and the second therapy designed to induce DNA damage in the cell are administered in a sub-therapeutic amount.

Non-limiting examples of the second therapy that induce DNA damage in a cell includes one or more of the following drugs: adriamycin, cytarabine, daunorubicin, idarubicin, cisplatin, oxaliplatin, carboplatin, irinotecan, camptothecin and derivatives thereof, capecitabine, methotrexate, chlorambucil, busulfan, clofarabine, fludarabine, pentostatin, cyclophosphamide, etoposide, fluorouracil, gemcitabine, ifosfamide, nelarabine, mechlorethamine, procarbazine, taxol, taxotere, topotecan, vincristine and vinblastine. Additional cancer therapies that induce DNA damage in a cell are well known to a person of ordinary skill in the art and such embodiments are within the purview of the invention.

Therapeutic and sub-therapeutic amounts of certain examples of the second therapy that induce DNA damage in a cell are provided in Table 4 below:

Table 4. Therapeutic and sub-therapeutic amounts exemplary second therapies that induce DNA damage in a cell. These dosages can be adjusted for individual subjects based on medical professional's judgment. Not all indications are listed in this table and dosage regimens for indications not listed herein are well known in the art. The dosages and route of administration can also be updated based on updates in medical practices.

| Drug | Therapeutic dose |
|---|---|
| Adriamycin | 60-75 mg/m$^2$ as a single intravenous injection administered at 21 day intervals; or 30 mg/m$^2$ on each of three successive days repeated every 4 weeks. The adult dosage regimens may be suitable for paediatric cases. An intra-arterial infusion for 1-3 days at doses of 45-100 mg/m$^2$. The recommended lifetime cumulative dose limit is 550 mg/m$^2$ body surface area. The total cumulative dose for adults aged 70 or older be restricted to 450 mg/m$^2$ body surface area. |
| Cytarabine | Acute Myelocytic Leukemia - induction remission: adults: 200 mg/m$^2$ daily by continuous infusion for 5 days (120 hours) - total dose 1000 mg/m$^2$. This course is repeated approximately every 2 weeks. Acute myelocytic leukemia - maintenance: adults: Maintenance programs are modifications of induction programs and, in general, use similar schedules of drug therapy as were used during induction. Most programs have a greater time spacing between courses of therapy during remission maintenance. Acute myelocytic leukemia - induction and maintenance in children: childhood AML responds better than adult AML given similar regimens. Where the adult dosage is stated in terms of body weight or surface area, the children's dosage may be calculated on the same basis. When specified amounts of a drug are indicated for the adult dosage, these should be adjusted for children on the basis of such factors as age, body weight or body surface area. |
| Daunorubicin | 60 to 75 mg/m$^2$ as a single intravenous injection administered at 21-day intervals. |
| Idarubicin | 12 mg/m$^2$ daily for 3 days by slow (10 to 15 min) intravenous injection in combination with cytarabine. The cytarabine may be given as 100 mg/m$^2$ daily by continuous infusion for 7 days or as cytarabine 25 mg/m$^2$ intravenous bolus followed by cytarabine 200 mg/m$^2$ daily for 5 days continuous infusion. |
| Cisplatin | Metastatic Testicular Tumors: 20 mg/m$^2$ IV daily for 5 days per cycle in combination with other approved chemotherapeutic agents. Metastatic Ovarian Tumors: 75 to 100 mg/m$^2$ IV per cycle once every 4 weeks (DAY 1) in combination with cyclophosphamide. The dose of cyclophosphamide when used in combination with PLATINOL is 600 mg/m$^2$ IV once every 4 weeks (DAY 1). As a single agent, 100 mg/m$^2$ IV per cycle once every 4 weeks. Advanced bladder cancer: 50 to 70 mg/m$^2$ IV per cycle once every 3 to 4 weeks |
| Oxaliplatin | Administered in combination with 5-fluorouracil/leucovorin every 2 weeks: Day 1: 85 mg/m$^2$ intravenous infusion in appropriate solution and leucovorin 200 mg/m$^2$ intravenous infusion in appropriate solution over 120 minutes, followed by 5-fluorouracil 400 mg/m$^2$ intravenous bolus over 2-4 minutes, followed by 5-fluorouracil 600 mg/m$^2$ in appropriate solution as 22-hour continuous infusion. Day 2: leucovorin 200 mg/m$^2$ intravenous infusion over 120 minutes, followed by 5-fluorouracil 400 mg/m$^2$ intravenous bolus given over 2-4 minutes, followed by 5-fluorouracil 600 mg/m$^2$ intravenous infusion in appropriate solution as a 22-hour continuous infusion. |
| Carboplatin | Single agent: 360 mg/m$^2$ IV on day 1 every 4 weeks. Combination with cyclophosphamide: Carboplatin 300 mg/m$^2$ IV on day 1 every four weeks for six cycles with cyclophosphamide 600 mg/m$^2$ IV on day 1 every four weeks for six cycles. |

-continued

| Drug | Therapeutic dose |
|---|---|
| Irinotecan | 125 mg/m$^2$ intravenous infusion on days 1, 8, 15, 22 with leucovorin 20 mg/m$^2$ intravenous bolus infusion on days 1, 8, 15, 22 followed by 5-fluorouracil intravenous bolus infusion on days 1, 8, 15, 22 every 6 weeks; or<br>180 mg/m$^2$ intravenous infusion on days 1, 15, 29 with leucovorin 200 mg/m$^2$ intravenous infusion on days 1, 2, 15, 16, 29, 30 followed by 5-fluorouracil 400 mg/m$^2$ intravenous bolus infusion on days 1, 2, 15, 16, 29, 30 and 5-fluorouracil 600 mg/m$^2$ intravenous infusion over 22 hours on days 1, 2, 15, 16, 29, 30; or<br>125 mg/m$^2$ intravenous infusion on days 1, 8, 15, 22 then 2-week rest; or<br>350 mg/m$^2$ intravenous infusion over 90 minutes on day 1 every 3 weeks. |
| Capecitabine | 2500 mg/m$^2$ administered orally daily with food for 2 weeks followed by a 1-week rest period given as 3 week cycles. |
| Methotrexate | Breast cancer: Cyclophosphamide 100 mg/m$^2$ p.o. days 1 through 14, Methotrexate 40 mg/m$^2$ i.v. day 1, 8, and 5-Fluorouracil 600 mg/m$^2$ i.v. day 1, 8. Cycle length will be 28 days ("2 weeks-on, 2 weeks-off"). In patients over 60 years of age, the dosage of Methotrexate is 30 mg/m$^2$ i.v. day 1, 8.<br>Gastric cancer: Methotrexate (1.5 g/m$^2$ IV day 1, +5-Fluorouracil (1.5 g/m$^2$ IV) + Leucovorin (15 mg/m$^2$ orally or IV every 6 hours for 72 hours) + Adriamycin (30 mg/m$^2$ IV, day 15). The schedule is repeated on day 29 for 6 cycles. |
| Chlorambucil | 0.1 to 0.2 mg/kg body weight daily for 3 to 6 weeks as required. |
| Busulfan | 0.8 mg per kg of ideal body weight or actual body weight, whichever is lower, administered intravenously as a two-hour infusion every six hours for four consecutive days for a total of 16 doses. |
| Clofarabine | Ages 1-21: 52 mg/m$^2$ of body surface area by intravenous infusion over 2 hours daily for 5 consecutive days followed by the recovery period of 2 to 6 weeks (median 4 weeks) from the starting day of the previous cycle. The cycles are repeated following recovery or return to baseline organ function. |
| Fludarabine | 25 mg/m$^2$ administered intravenously over a period of approximately 30 minutes daily for five consecutive days. Each 5 day course of treatment should commence every 28 days. |
| Pentostatin | Hairy cell leukemia: Adults: IV: 4 mg/m$^2$ every 2 weeks.<br>Chronic lymphocytic leukemia (off-label use): Adults: IV:<br>Previously treated: 4 mg/m$^2$ once every 3 weeks in combination with cyclophosphamide and rituximab for 6 cycles; or<br>Previously untreated: 2 mg/m$^2$ once every 3 weeks in combination with cyclophosphamide and rituximab for 6 cycles.<br>Cutaneous T-cell lymphomas, mycosis fungoides/Sezary syndrome (off-label use): Adults: IV: 4 mg/m$^2$ once weekly for 3 weeks, then every 2 weeks for 6 weeks, then once monthly for a maximum of 6 months.<br>T-cell prolymphocytic leukemia, refractory (off-label use): Adults: IV: 4 mg/m$^2$ once weekly for 4 weeks then every 2 weeks until optimum response is achieved. |
| Cyclophosphamide | Intravenous: Initial course for patients with no hematologic deficiency: 40 mg per kg to 50 mg per kg in divided doses over 2 to 5 days; or<br>Oral: 1 mg per kg per day to 5 mg per kg per day for both initial and maintenance dosing. |
| Etoposide | Testicular cancer: 50 to 100 mg/m$^2$ per day on days 1 through 5 to 100 mg/m$^2$ per day on days 1, 3, and 5 in combination with other approved chemotherapeutic agents.<br>Small cell lung cancer: 35 mg/m$^2$ per day for 4 days to 50 mg/m$^2$ per day for 5 days for in combination with other approved chemotherapeutic drugs. |
| Fluorouracil | 12 mg/kg are given intravenously once daily for 4 successive days. The daily dose should not exceed 800 mg. |
| Gemcitabine | Ovarian Cancer: 1000 mg/m$^2$ I.V. on Days 1 and 8 of each 21-day cycle.<br>Breast Cancer: 1250 mg/m$^2$ I.V. on Days 1 and 8 of each 21-day cycle.<br>Non-Small Cell Lung Cancer: 1000 mg/m$^2$ I.V. on Days 1, 8, and 15 of each 28-day cycle or 1250 mg/m$^2$ I.V. on Days 1 and 8 of each 21-day cycle.<br>Pancreatic Cancer: 1000 mg/m$^2$ I.V. once weekly for the first 7 weeks, then one week rest, then once weekly for 3 weeks of each 28-day cycle. |

| Drug | Therapeutic dose |
| --- | --- |
| Ifosfamide | 2000-2400 mg/m$^2$ per day over a period of a minimum of 30 minutes, on 5 consecutive days. |
| Nelarabine | Adult Dosage: 1,500 mg/m$^2$ administered intravenously on days 1, 3, and 5 repeated every 21 days.<br>Pediatric Dosage: 650 mg/m$^2$ administered intravenously over 1 hour daily for 5 consecutive days repeated every 21 days. |
| Mechlorethamine | A total dose of 0.4 mg/kg of body weight for each course usually is given either as a single dose or in divided doses of 0.1 to 0.2 mg/kg per day. |
| Procarbazine | Adults: Single or divided doses of 2 to 4 mg/kg/day for the first week and maintained at 4 to 6 mg/kg/day until maximum response is obtained.<br>Pediatric: 50 mg/m$^2$ per day for the first week and maintained at 100 mg/m$^2$ per day until maximum response is obtained. |
| Taxol | Premedicated to prevent severe hypersensitivity reactions.<br>Previously untreated patients with carcinoma of the ovary: one of the following recommended regimens of taxol may be given every 3 weeks:<br>a. 175 mg/m$^2$ I.V. followed by 75 mg/m$^2$ cisplatin; or<br>b. 135 mg/m$^2$ I.V. followed by 75 mg/m$^2$ cisplatin.<br>Previously treated with chemotherapy for carcinoma of the ovary: 135 mg/m$^2$ or 175 mg/m$^2$ I.V. every 3 weeks. |
| Taxotere | Breast cancer: 60 mg/m$^2$ to 100 mg/m$^2$ single agent;<br>BC adjuvant: 75 mg/m$^2$ administered 1 hour after doxorubicin 50 mg/m$^2$ and cyclophosphamide 500 mg/m$^2$ every 3 weeks for 6 cycles.<br>NSCLC: after platinum therapy failure: 75 mg/m$^2$ single agent.<br>NSCLC: chemotherapy-naive: 75 mg/m$^2$ followed by cisplatin 75 mg/m$^2$.<br>Hormone Refractory Prostate Cancer: 75 mg/m$^2$ with 5 mg prednisone twice a day continuously.<br>Gastric adenocarcinoma: 75 mg/m$^2$ followed by cisplatin 75 mg/m$^2$ (both on day 1 only) followed by fluorouracil 750 mg/m$^2$ per day as a 24-hr I.V. (days 1-5), starting at end of cisplatin infusion.<br>Squamous Cell Carcinoma of the Head and Neck Cancer: 75 mg/m$^2$ followed by cisplatin 75 mg/m$^2$ I.V. (day 1), followed by fluorouracil 750 mg/m$^2$ per day I.V. (days 1-5), starting at end of cisplatin infusion; for 4 cycles; or 75 mg/m$^2$ followed by cisplatin 100 mg/m$^2$ I.V. (day 1), followed by fluorouracil 1000 mg/m$^2$ per day as a 24-hr I.V. (days 1-4); for 3 cycles. |
| Topotecan | Ovarian cancer and small cell lung cancer: 1.5 mg/m$^2$ by I.V. daily for 5 consecutive days, starting on Day 1 of a 21-day course.<br>Cervical cancer: 0.75 mg/m$^2$ by I.V. on Days 1, 2, and 3 repeated every 21 days in combination with cisplatin 50 mg/m$^2$ on Day 1. |
| vincristine | Pediatric patients: 1.5-2 mg/m$^2$, administered once a week.<br>Adults: 1.4 mg/m$^2$. |
| Vinblastine | Weekly intervals at the following doses: first dose 3.7 mg/m$^2$; second dose 5.5 mg/m$^2$; third dose 7.4 mg/m$^2$; fourth dose 9.25 mg/m$^2$; and fifth dose 11.1 mg/m$^2$. |

Materials and Methods

Colony Formation Assay:

Colony formation assays measures the ability of a single cell to not only survive, but also to proliferate. Thus, it is an indirect measurement of cancer stem cell activity, the ability of a single cell to give rise to a host of progeny. The BRCA1-deficient MDA-MB-436 breast cancer cells were cultured in DMEM supplemented with 10% FBS and 1% penicillin and streptomycin. BRRCA1-deficient UWB1.289 ovarian cancer cells were cultured and maintained in 50% MEBM medium with growth factors and 50% RPMI medium supplemented with 3% FBS and 1% penicillin and streptomycin. 25 nm of mirVana miR-223 3p mimic from Ambion life technologies (Cat #4464067) was used to deplete PARP1 protein in these cell lines. Mir223-3p was encapsulated into the lipid transfection complex, RNAiMAX. 25 nm of miR-223-3p was incubated in 500 μL Opti-MEM plus 6 μl of RNAiMAX for 20 mins at room temperature and then added to the cells for a final volume of 1 ml. After 48 hours, the cells were trypsinized, counted and plated in 6 well plates at a density of 4000 cells per well, in triplicates. After 14 days of incubation, colonies were stained with 0.1% crystal violet in methanol and counted using Image J software. PARP1 repression by miR-223-3p was shown by western blot. PARP1 antibody was purchased from Cell Signaling (46D11).

Quantitative real time PCR (qRT-PCR) measuring endogenous miR-223 If miR-223-3p is a physiologic regulator of PARP1 expression, then its expression should be repressed after DNA damage, when higher levels of PARP1 are required to repair this damage. Mir223-3p is most highly expressed in hematopoietic cells, such as the HL60 cell line. HL60 cells were treated with 50 μM cytarabine (Ara-C) for 1hr, 4 hr, 8 hr, 12 hr and 24 hr. Western blot analysis was performed to examine PARP1 protein levels in these samples. For measuring levels of miR-223-3p, cells were collected at the above time points, RNA isolated using the Qiagen RNeasy kit. cDNA conversion was then performed using first-strand cDNA synthesis kit for miRNA from Origene (HP100042). qRT-PCR for miR-223 3p was performed on a 7900HT Fast Real-Time PCR system (ABI)

according to Origene protocol and ΔCT values were calculated. Primers used were, Forward (TGTCAGTTTGT-CAAATACC, SEQ ID NO: 90) and Reverse (GAA-CATGTCTGCGTATCTC, SEQ ID NO: 91). U6 RNA was used as an endogenous control.

Alternative Non-Homologous End Joining (aNHEJ) Assay:

PARP1 is involved in the initial step in aNHEJ DNA double strand break repair. If PARP1 is repressed, then aNHEJ is decreased. The EJ2-GFP U2OS system was used to assess aNHEJ. This reporter system contains single, integrated copy of reporter with I-SceI target sites. These sites were cleaved upon transfection of an I-SceI expression vector. Cells were transfected with miR-223 3p mimic using RNAiMAX. 24 hours after transfection, the cells were transfected with I-SceI vector using polyethylenimine (PEI). After 72 hours, EJ2 cells were trypsinized, washed with PBS and GFP-positive cells were measured using FACSort (Becton-Dickinson, San Jose, Calif.). The GFP positive cells are proportional to the aNHEJ frequency.

Luciferase Assay for Assessing Stability of PARP1 3' UTR mRNA

A549 cells were transfected with miR-223-3p mimic using RNAiMAX as above. After 6 hours, these cells were transfected with PARP 3'UTR plasmid fused with dual luciferase reporter from GeneCopoeia using Lipofectamine 2000. 48 hours post-transfection, cells were collected and assessed for luciferase activity using Luc-Pair Dual Luciferase assay kit from GeneCopoeia. The firefly luciferase activity is normalized against *Renilla* luciferase, which serves as a transfection control.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting.

Example 1 — Effect of PARP1 Inhibition on BAP1 Mutant Human Mesothelioma Cells

BAP1 (BRCA1-Associated Protein 1) is a 90 kDa protein that binds to the RING finger domain of BRCA1. BAP1 gene is located on chromosome 3p21 and it possesses tumor suppressor activity. Deletion of this region is seen in several cancers including breast cancer, lung cancer, uveal melanoma and mesothelioma. BAP1 has been shown to interact with BRCA1/BARD1 complex and regulate DNA damage response.

Figure 24B:
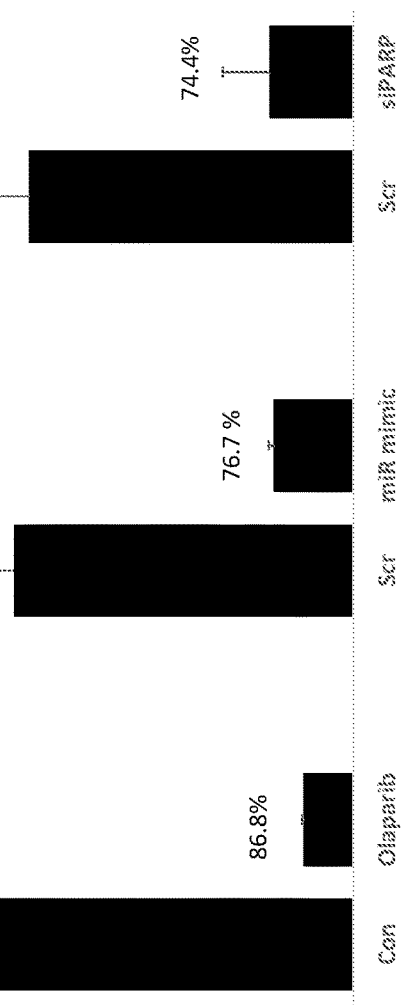
FIGS. 24A-24B.
Figure 24A:
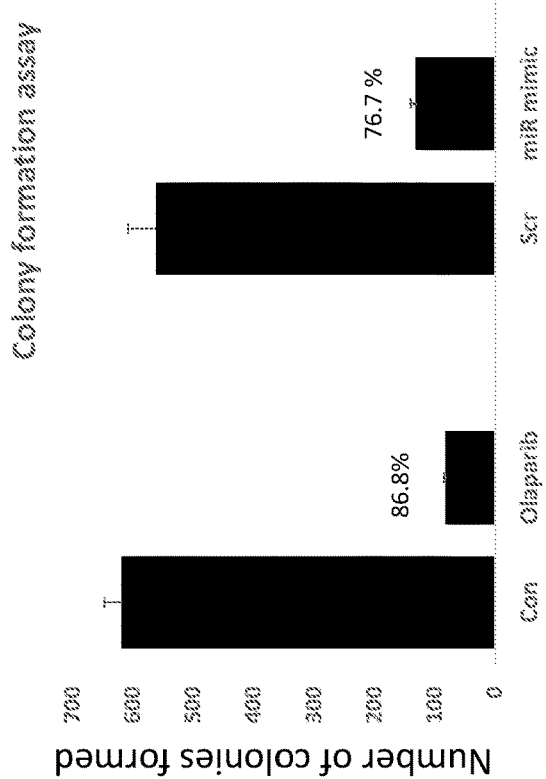
Figures 25A, 25B:
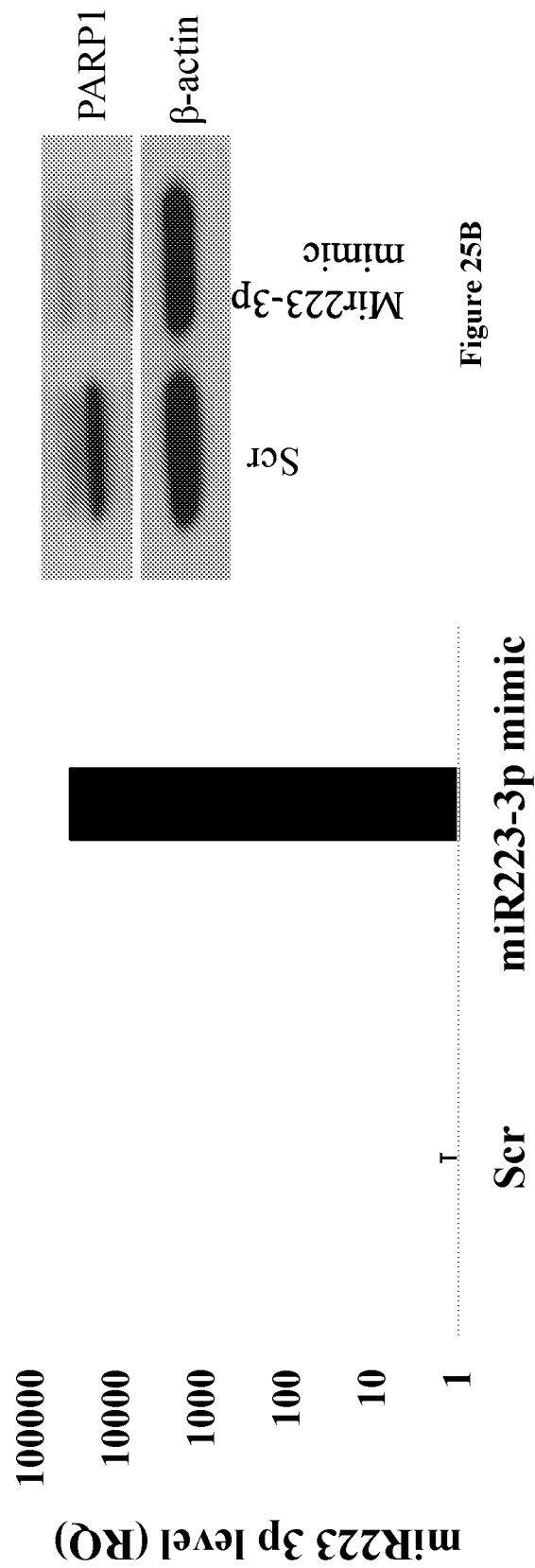
FIGS. 25A-25B. Expression of miR223-3p mimic in cells (FIG. 25A) and repression of PARP1 using a miR223 mimic (Mir223-3p.

BAP1 mutant cells have also been shown to be deficient in HR similar to BRCA1/2 mutant cells. These cells were treated with the PARP inhibitor, olaparib. Human Mesothelioma cells (H-Meso 01A) were cultured in RPMI media supplemented with 10% FBS and 1% Penicillin/Streptomycin. These cells were seeded in a 6-well plate at a density of 4000 cells/well and allowed to grow for 18 hours. Of the six wells, three wells were treated with 3 olaparib (LC laboratories, Cat #0-9201) each and the other three wells were considered as controls. The cells were allowed to grow for 10 days. Olaparib stayed on the cells throughout the experiment. After 10 days of incubation, colonies were stained with 0.1% crystal violet in methanol and counted using Image J software. Olaparib killed at least 80-90% of the cells. The experiment was done three times, each in triplicates and the average from all three times was calculated (FIG. 24).

Example 2

Materials and Methods

Figure 44:
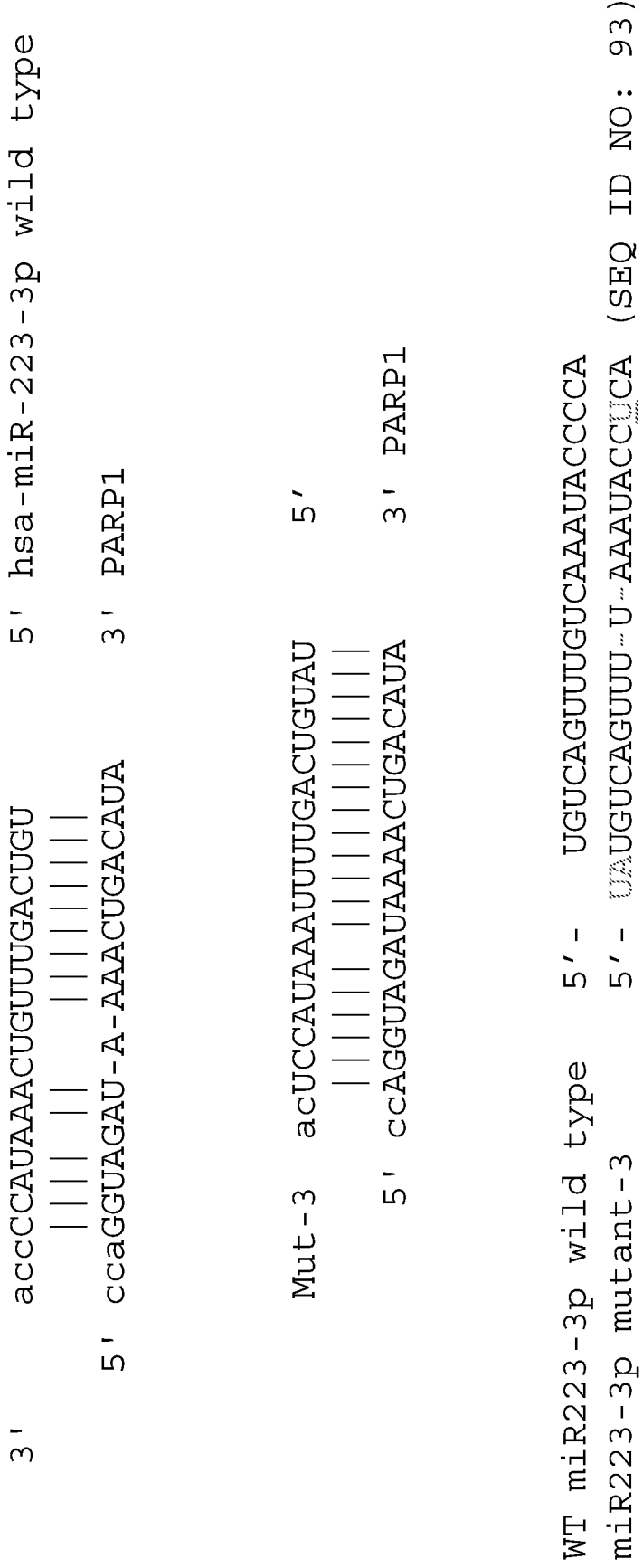
FIG. 44. Gain of function mutant for mir-223-3p (SEQ ID NO: 93). The "-" represents a deleted nucleotide within the wild type miR223-3p.

Cell Culture, miRNA transfection and Survival Assay. The BRCA1-deficient MDA-MB-436 breast cancer cells were cultured in DMEM supplemented with 10% FBS and 1% penicillin and streptomycin. BRRCA1-deficient UWB1.289 ovarian cancer cells were cultured and maintained in 50% MEBM medium with growth factors and 50% RPMI medium supplemented with 3% FBS and 1% penicillin and streptomycin. BAP1-mutant H2452 mesothelioma cells were cultured in RPMI 1640 medium supplemented with 10% fetal bovine serum and 1% penicillin and streptomycin. 25 nm of mirVana miR223-3p mimic from Ambion life technologies (Cat #4464067) was used to deplete PARP1 protein in these cell lines. Mir223-3p was encapsulated into the lipid transfection complex, RNAiMAX. 25 nm of mir223-3p was incubated in 500 UL Opti-MEM plus 6 ul of RNAiMAX for 20 mins at room temperature, and then added to the cells for a final volume of 1 ml. After 48 hours, the cells were trypsinized, counted and plated in 6 well plates at a density of 4000 cells per well, in triplicates. After 14 days of incubation, colonies were stained with 0.1% crystal violet in methanol and counted using Image J software. PARP1 repression by mir223-3p was shown by western blot. PARP1 antibody was purchased from Cell Signaling (46D11). Results are shown in FIGS. 25 and 27-32. FIG. 44 illustrates the depletion of other DNA repair components in addition to PARP1.

Nuclear Structure Assays and DNA Damage Foci. Nuclear structural abnormalities (micronuclei and bridging) arising from aberrant chromosomal segregation after replication fork fusion were assessed as we described. Briefly, miR223 mimic transfected cells were grown on coverslips, and then 72 h after treatment, cells were fixed in 100% methanol at −20° C. for 20 min. The fixed cells were mounted using DAPI-Fluoromount G clear mounting media from SouthernBiotech and analyzed within 24 hours with laser confocal scanning microscope (TCS-SP5, Leica Microsystems, Exton, Pa.) as we described. At least 6 distinct determinations (100-150 nuclei per determination) were performed for each group.

Figure 33A:
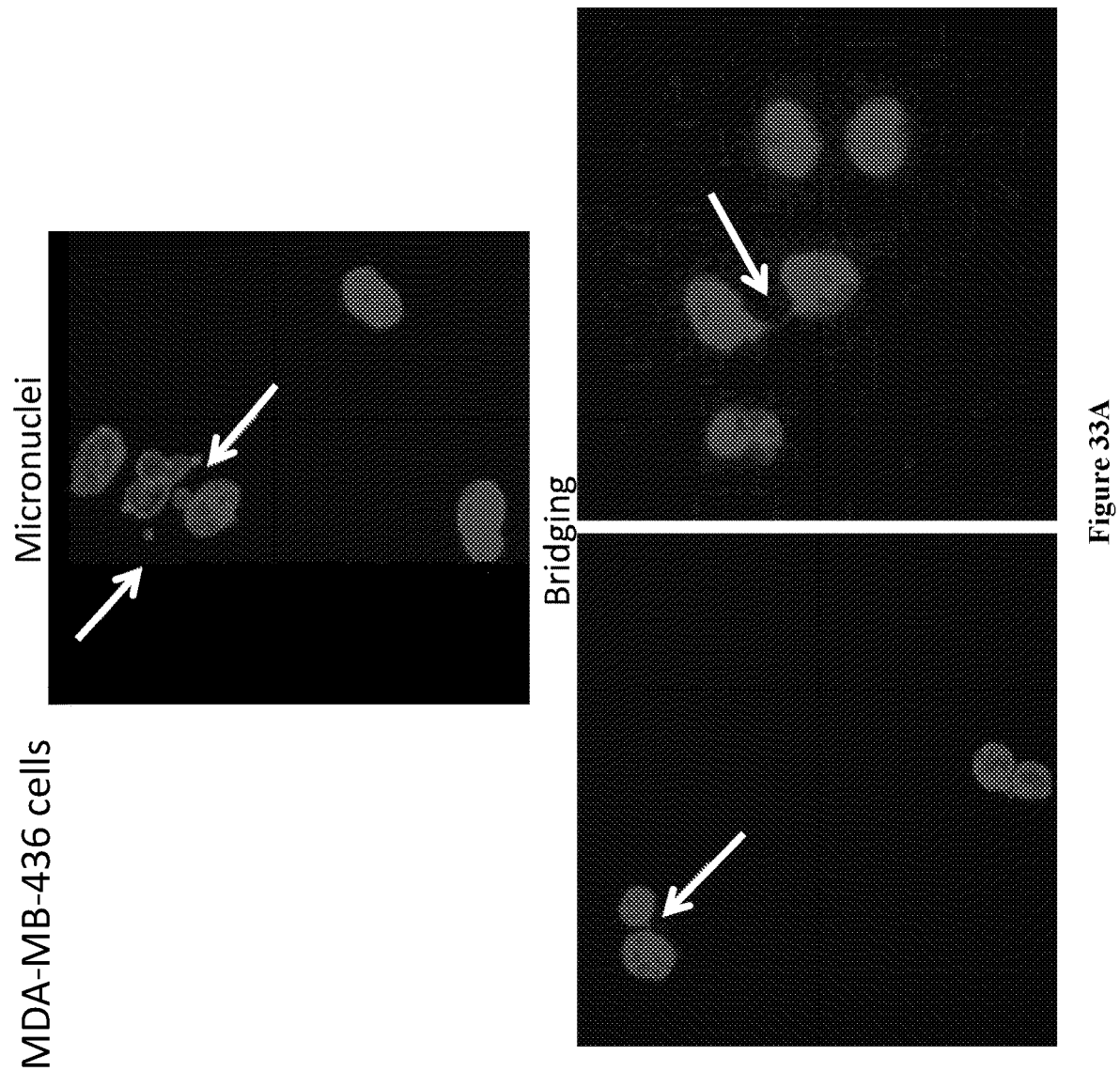
FIGS. 33A-33C. Effect of miR223-3p on DNA damage (FIGS. 33A and 33B). 25 nM of either the scr or miR223-3p mimic were transfected into cells 72 hours after transfection, the cells are fixed and stained with DAPI. Knockdown of PARP1 by miR223-3p (FIG. 33C).
Figure 33C:
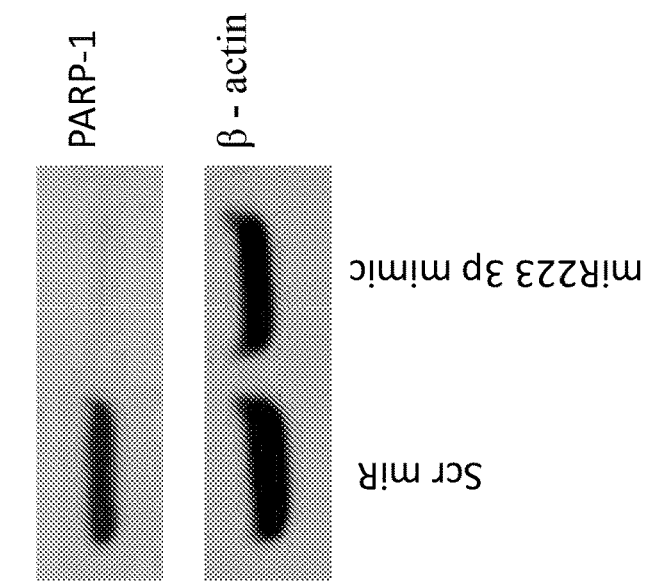
Figure 33B:
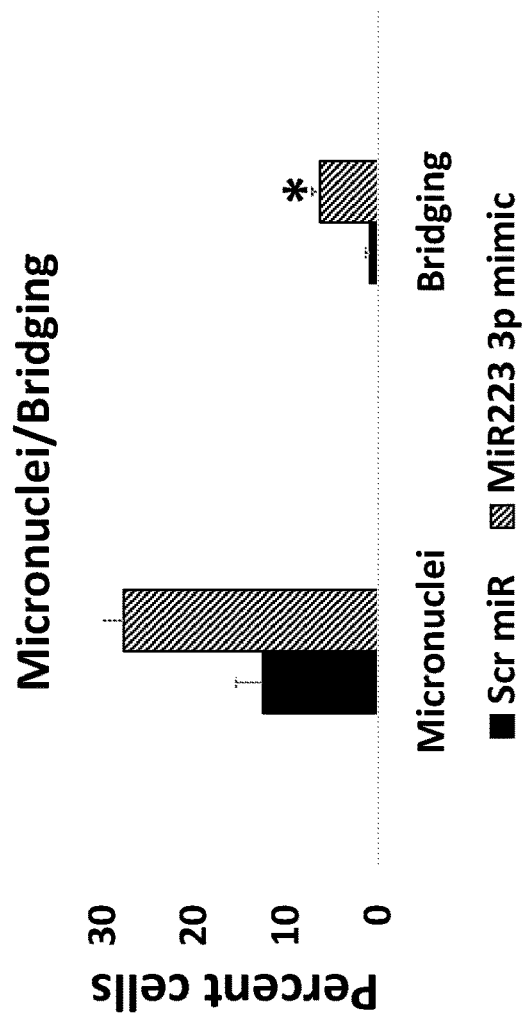
Figure 34:
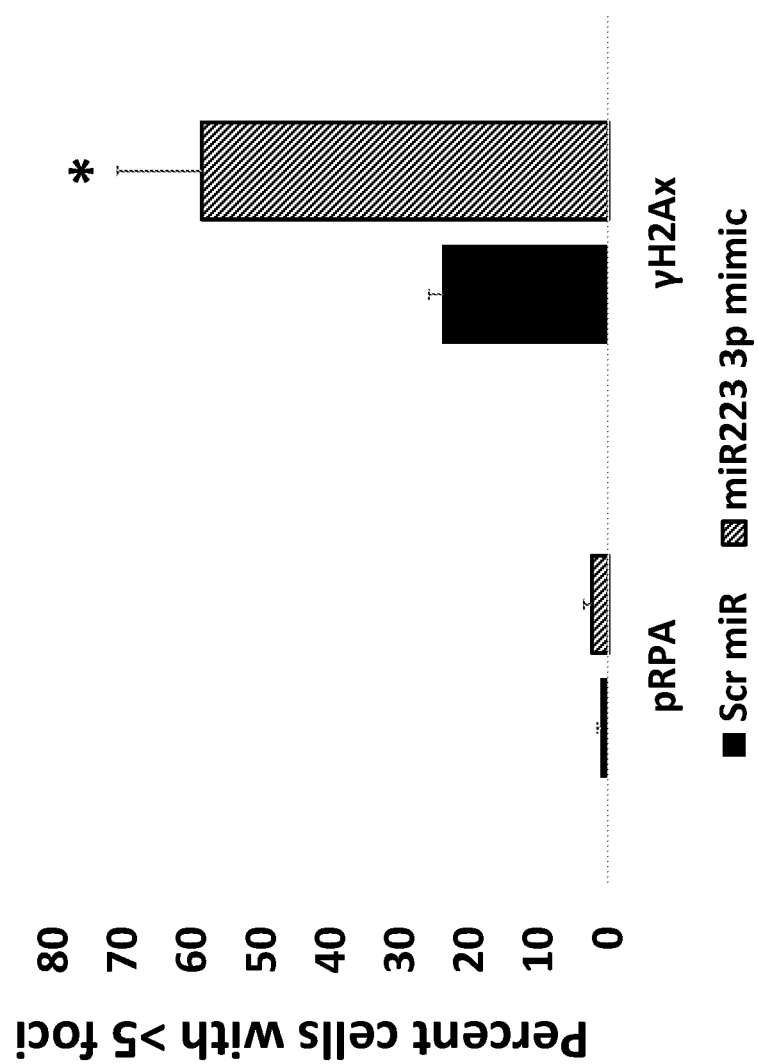
FIG. 34. Effect of miR223-3p on DNA damage.

Confocal Immunofluorescence foci assays were performed for γ-H2Ax DNA damage foci analysis. After the cells were fixed like mentioned above, the coverslips were incubated with γ-H2AX (S139) primary antibody at 1:250 dilution in 1% BSA in TBS at 4° C. overnight in a humidifying chamber. Following overnight incubation, the coverslips were washed with TBS 3 times for 5 minutes each and incubated with 1:400 Alexa Fluor 488 for 1 hr at room temperature. The coverslips were washed 3 times with TBS for 5 mins each. γ-H2AX (S139) primary antibody was from Millipore (Billerica, Mass.), and the secondary antibody conjugated with Alexa Fluor dye was from Invitrogen (Waltham, Mass.). After staining, coverslips were mounted with DAPI-Fluoromount G clear mounting media from Southern Biotech (Birmingham, Ala.) and analyzed within 24 hours with a laser confocal scanning microscope (TCS-SP5). At least 6 distinct determinations (100-150 nuclei per determination) were performed for each condition for statistical analysis). Cells with more than five foci were counted as positive. Photomicrographs of each distinct cell population were taken at equal magnifications and equal fluorescence intensities. Results of these assays are shown in FIGS. 33-34.

Figure 35:
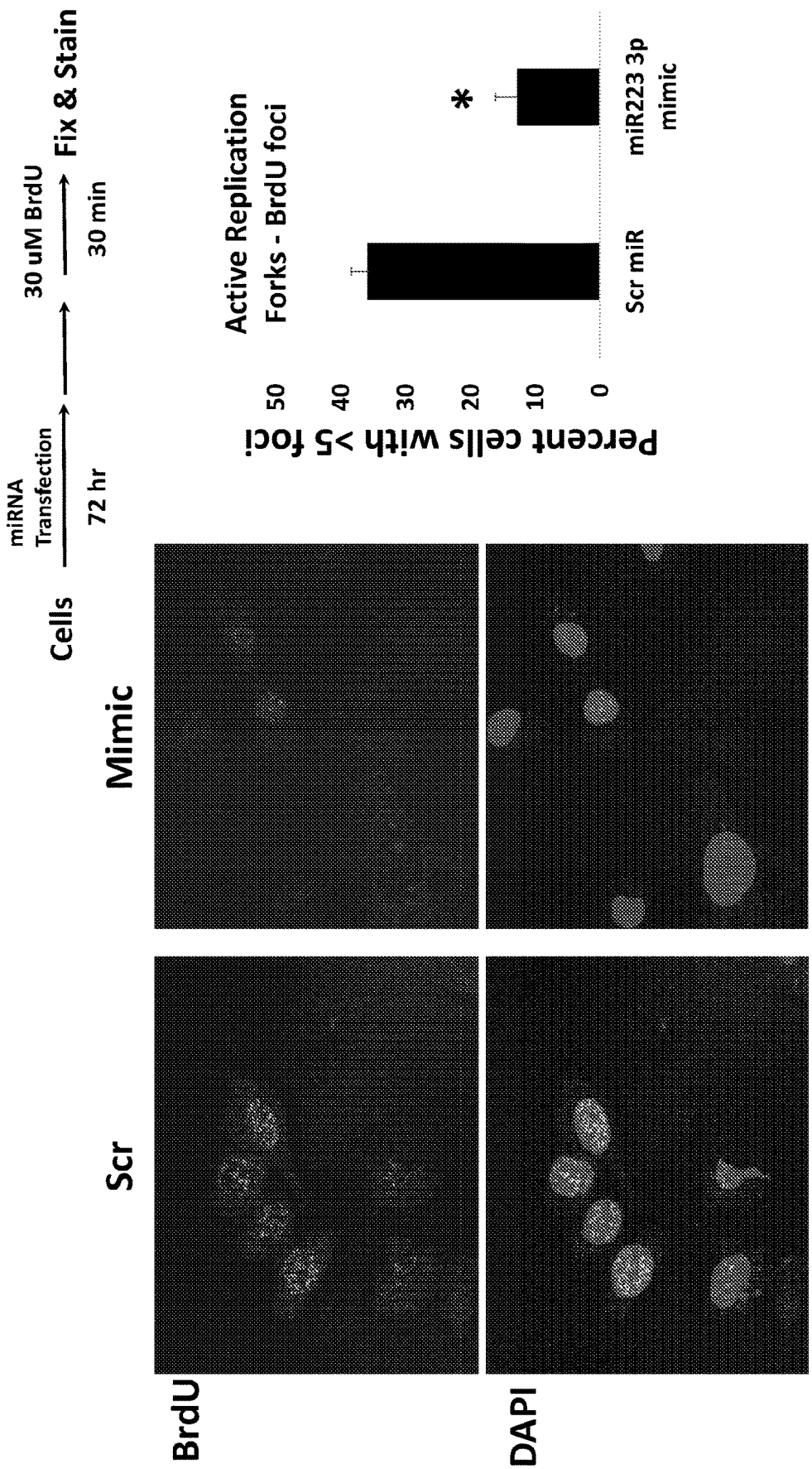
FIG. 35. miR223-3p decreases active replication forks in MDA-MB-436 BRCA mutant cells. Cells were transfected with miRNA, seventy-two hours later, the cells were treated with 30 micromolar BrdU for 30 minutes and then fixed and stained.

Active Replication Forks Analysis. Active Replication forks after miR223-3p mimic transfection were measured using immunofluorescent detection of BrdU foci after DNA denaturation. Briefly, 72 hours after transfection, cells were released into fresh media containing 10 uM BrdU (BD Biosciences, Franklin Lakes, N.J.) for 30 min. After washing, cells on coverslip were fixed and the DNA denatured using hydrochloric acid for BrdU immunostaining. The coverslips were processed for immunostaining using BrdU-specific antibody (Cell Signaling, Danvers, Mass.) and then incubated with a secondary antibody conjugated with Alexa Fluor dye from Invitrogen for 1 h. Cells were analyzed as above using the laser scanning confocal microscope. At least five hundred cells were counted for each condition from at least six distinct slides per condition for statistical analysis. Results of these assays are shown in FIGS. 35-36.

Figure 37:
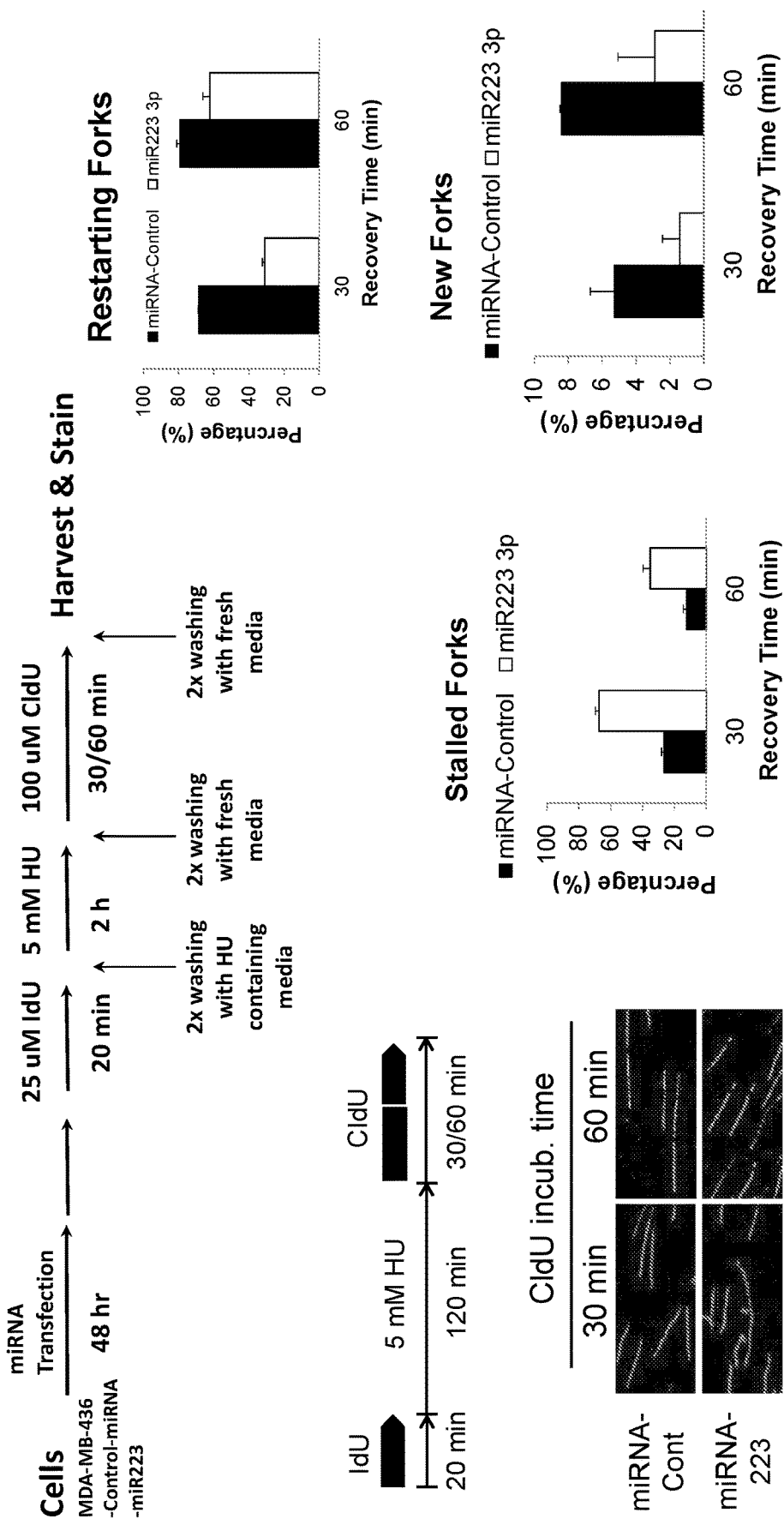
FIG. 37. DNA fiber analysis showing defective replication fork restart

Replication Fork Restart. DNA fiber analysis was performed to measure replication fork restart in cells transfected with either scramble control or 25 nM miR223-3p mimic. Briefly, cells were grown in 6-well tissue culture dishes. 48 hours after transfection, 20 µM IdU was added to growth medium, mixed and incubated for 10 min at 37° C. Media was removed and cells were washed with media containing 5 nM hydroxyurea (HU). Then, cells were either treated with 5 mM HU or mock treated for 2 hours. Medium was then replaced with fresh medium containing 20 µM CldU and cells were incubated for 20 min at 37° C. Cells were harvested, resuspended in PBS, 2500 cells were transferred to a positively charged microscope slide (Superfrost/Plus, Daigger, Vernon Hills, Ill.), lysed with 6 µl of 0.5% SDS, 200 mM Tris-HCl, pH 7.4, 50 mM EDTA and incubated at room temperature for 5 min. Slides were tilted to allow DNA to spread via gravity, covered with aluminum foil. They are then air-dried for 8 min, fixed for 5 min with 3:1 methanol:acetic acid (prepared fresh), air dried for 8 min, and stored in 70% ethanol at 4° C. overnight. Slides were deproteinized in 2.5 N HCl at 37° C. for 1 h, blocked with 5% BSA and labeled sequentially for 1 h each with mouse anti-BrdU antibody (BD Biosciences, San Jose, Calif.), secondary goat anti-mouse Alexa 568 (Invitrogen), rat anti-BrdU (Accurate Chemical, Westbury, N.Y.) and secondary donkey anti-rat Alexa 488 (Invitrogen). Slides were mounted in PermaFluor aqueous, self-sealing mounting medium (Thermoscientific, Waltham, Mass.). DNA fibers were visualized using an LSM 510 confocal microscope (Zeiss, Thornwood, N.Y.) optimized for each Alexa dye. Images were analyzed using Zeiss LSM Image Browser software. Experimental results are depicted in FIG. 37.

Figure 40B:
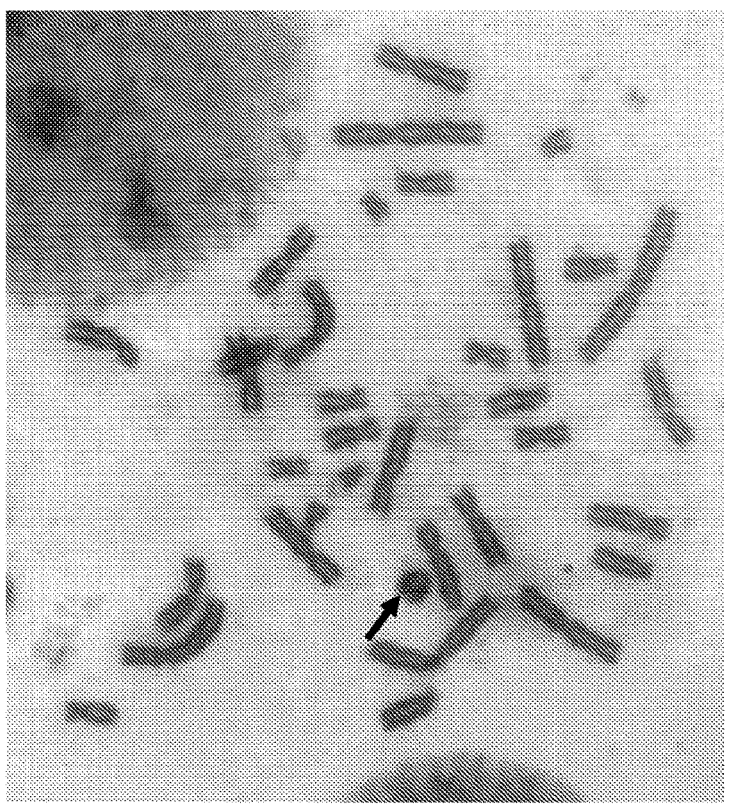
FIGS. 40A-40B and 41. Metaphase spreads in Jurkat cells. Different chromosomal translocation events such as ring chromosome, dicentric chromosome, double minutes and cruciform structures were counted and quantitated individually (FIGS. 40A, 40B and 41).
Figure 40A:
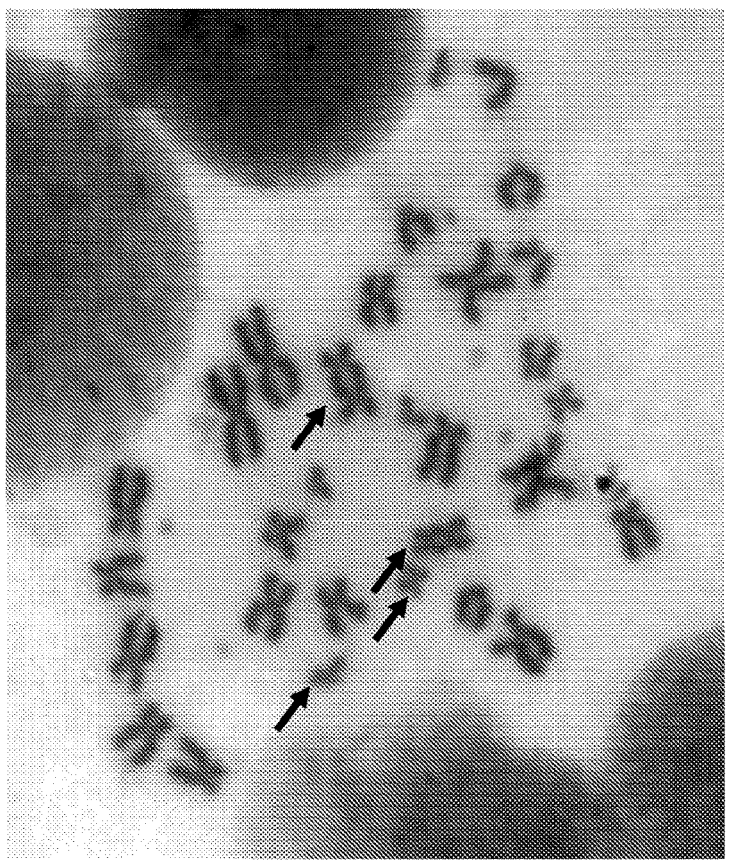
Figure 41:
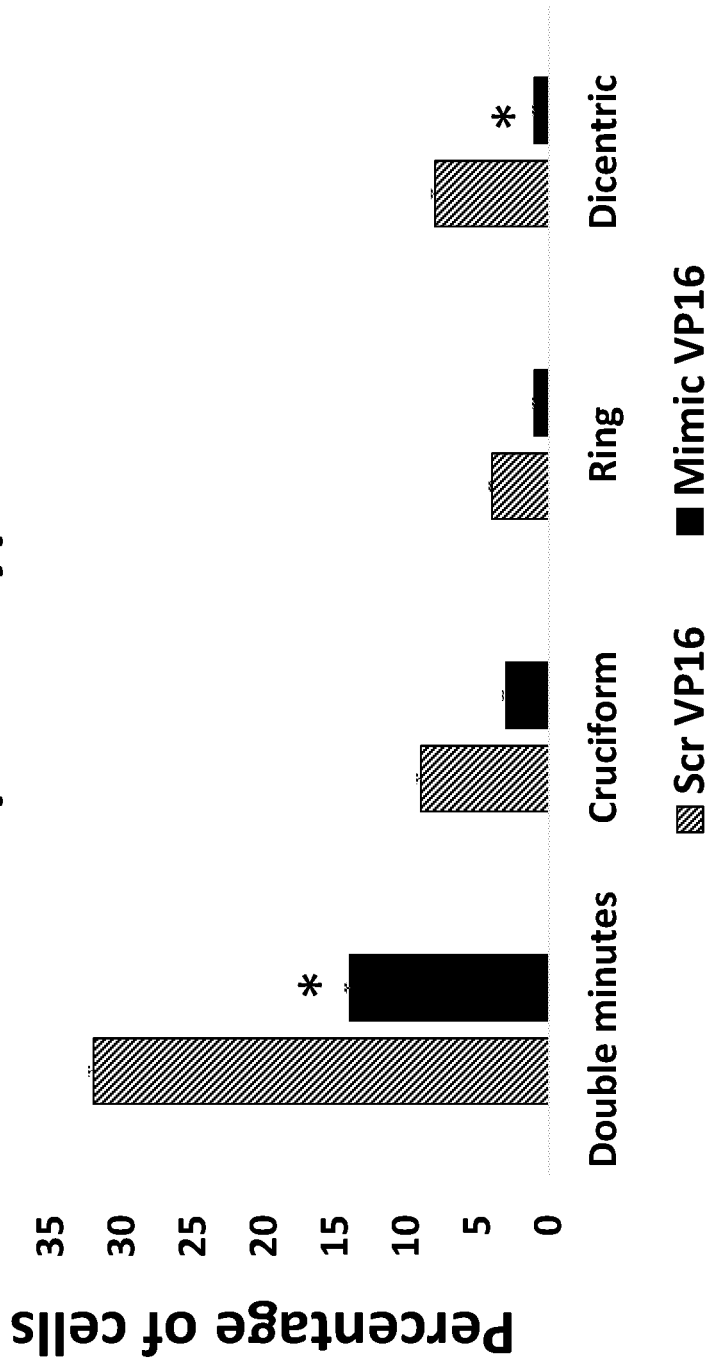
Figure 42B:
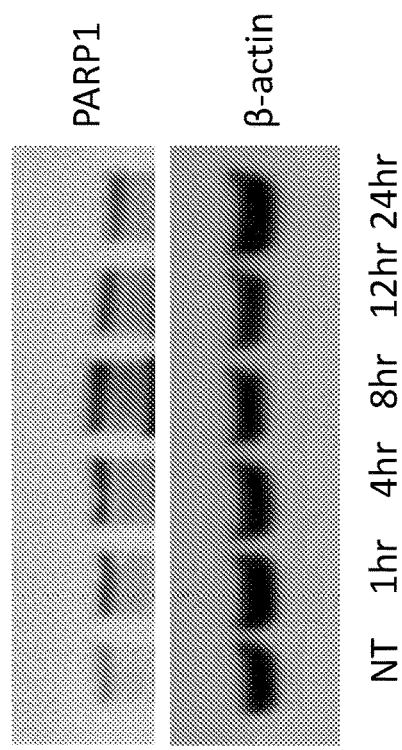
FIGS. 42A and 42B. miR223-3p is a global regulator of genomic stability. qRT-PCR showing gradual decrease in the levels of endogenous miR223 at different time points after treating the cells with 50 uM Ara-C(NT-non-treated.
Figure 42A:
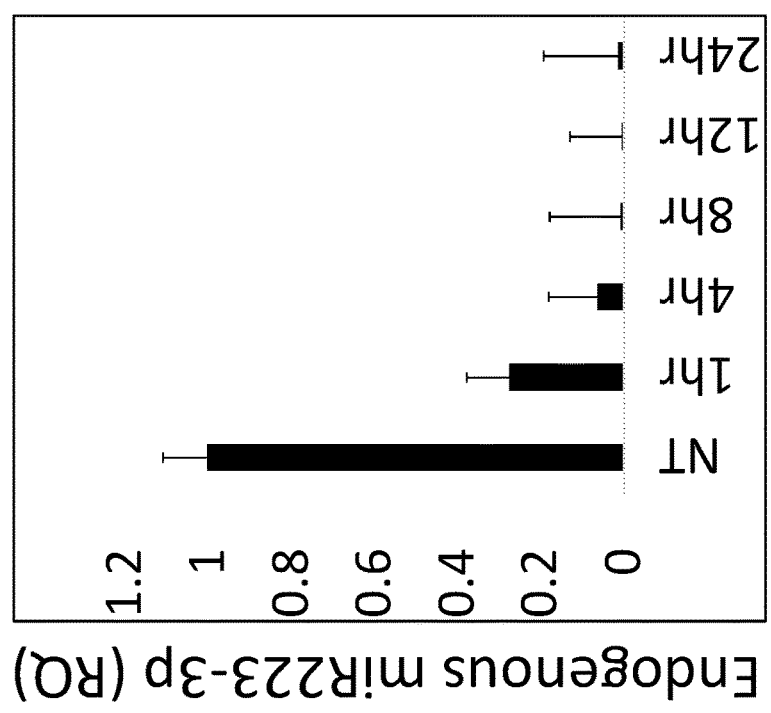
Figure 43:
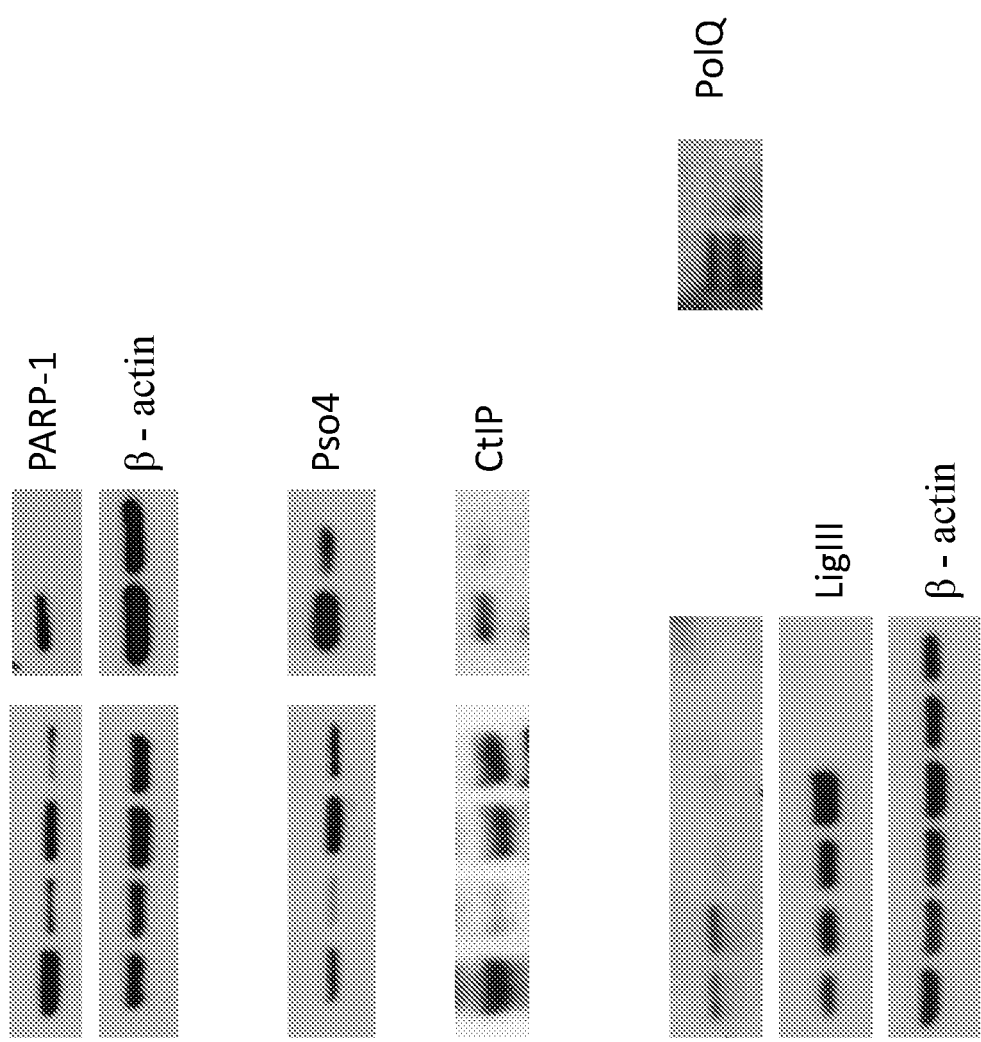
FIG. 43. Mirr223-3p depletes other DNA repair components as well as PARP1. MDA MB 436, HCC1937 and H2452 cells were transfected with scr control and miR223-3p mimic. Cells were collected after 48 hours. From left to right, Lane 1: MDA scr; Lane 2: MDA mimic; Lane 3: 1937 scr; Lane 4: 1937 mimic; Lane 5: H2452 scr; Lane 6: H2452 mimic.

Cytogenetic Analysis. Structural aberrations in metaphase chromosomes were scored after solid Giemsa staining as we described. Jurkat cells cultured in RPMI media with 10% FBS and 1% Penicillin-Streptomycin, were transfected with either scramble control or 25 nM miR223-3p mimic. 48 h after transfection, the cells were replaced with fresh media containing 10 ug/mL of KaryoMAX colcemid stock (ThermoFisher Scientific, Waltham, Mass.) to give a final concentration of 0.1 ug/mL and incubated for 1 h in the cell culture incubator. The cells were then washed with fresh media and 2 mL of pre-warmed 75 mM KCl was added to the cells and incubated at 37° C. for 10 min in a 15 mL conical tube. To the KCl, 5-10 drops of 3:1 methanol/acetic acid fixative was added by gently mixing the tube. The tubes were then centrifuged at 3000 rpm for 5 mins and to this, fresh identical fixative was added and incubated at room temperature for 5 min. The fixation step was repeated twice. The fixed cells were then added to a slide dropwise to spread them and allowed to air dry. After drying, the slides were covered with 4% Giemsa stain (Gibco) for 4 min at room temperature. The stain was then washed off in water and a coverslip was mounted on each slide using Fluoromount G (SouthernBiotech) mounting media. At least 20 metaphases were counted per condition. Different chromosomal translocation events such as ring chromosome, dicentric chromosome, double minutes and cruciform structures were counted and quantitated individually. Results are shown in FIGS. 40-41.

Quantitative Real Time PCR (qRT-PCR) Measuring Endogenous miR223-3p. If mir223-3p is a physiologic regulator of PARP1 expression, then its expression should be repressed after DNA damage, when higher levels of PARP1 are required to repair this damage. Mir223-3p is most highly expressed in hematopoietic cells, such as the HL60 cell line. HL60 cells were treated with 50 uM cytarabine (Ara-C) for 1 hr, 4 hr, 8 hr, 12 hr and 24 hr. Western blot was performed to look at PARP1 protein levels in these samples. For measuring levels of miR223-3p, cells were collected at the above time points, RNA isolated using the Qiagen RNeasy kit. cDNA conversion was then performed using first-strand cDNA synthesis kit for miRNA from Origene (HP100042). qRT-PCR for miR223 3p was performed on a 7900HT Fast Real-Time PCR system (ABI) according to Origene protocol and ΔCT values were calculated. Primer used was, Forward (TGTCAGTTTGT-CAAATACC) (SEQ ID NO:90) Reverse (GAA-CATGTCTGCGTATCTC) (SEQ ID NO:91). U6 RNA was used as an endogenous control. Results are shown in FIG. 38.

Figures 39A, 39B:
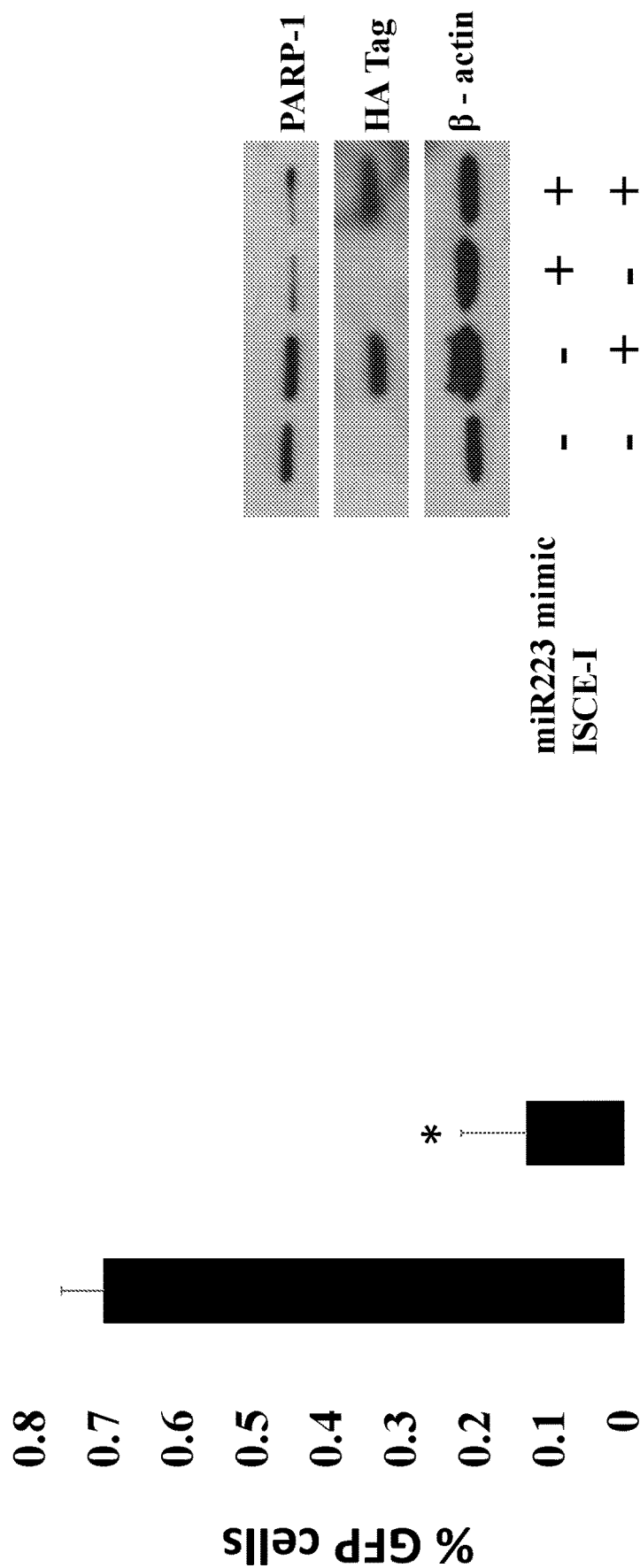
FIGS. 39A-39B. Effect of miR223-3p on aNHEJ in EJ2-GFP cell reporter system (percent GFP positive cells (FIG. 39A) and Western blot showing knockdown of PARP1 (FIG. 39B).

Alternative Non-Homologous End Joining (aNHEJ) assay. PARP1 is the initial step in aNHEJ DNA double strand break repair. If PARP1 is repressed, then aNHEJ will be decreased. The EJ2-GFP U2OS system was used to assess aNHEJ. This reporter system contains single, integrated copy of reporter with I-SceI target sites. These sites were cleaved upon transfection of an I-SceI expression vector. Cells were transfected with miR223 3p mimic using RNAiMAX. 24 hours after transfection, the cells were transfected with I-SceI vector using polyethylenimine (PEI). After 72 hours, EJ2 cells were trypsinized, washed with PBS and GFP-positive cells were measured using FACSort (Becton-Dickinson, San Jose, Calif.). The GFP positive cells are proportional to the aNHEJ frequency. Results are shown in FIG. 39.

Figure 26B:
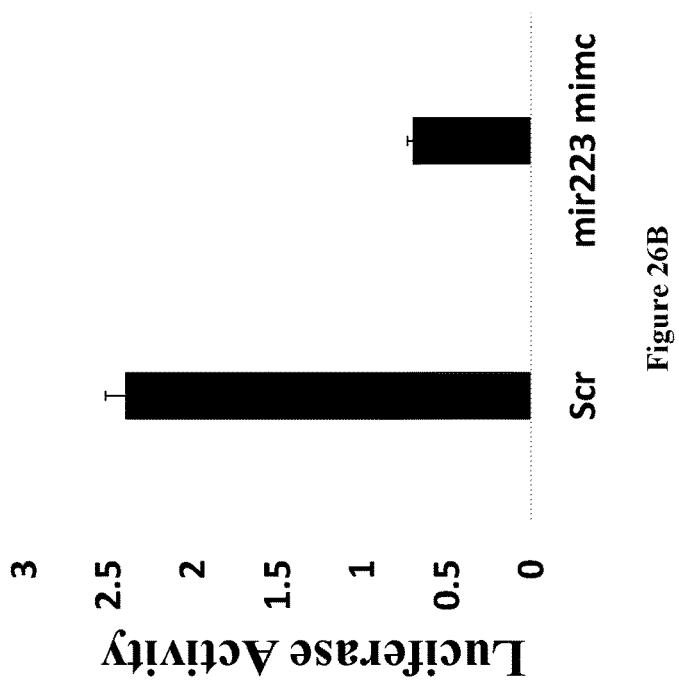
FIGS. 26A-26B. Construct (FIG. 26A) and assay results (FIG. 26B) for miR223-3p mimic induced inhibition of PARP1 using a luciferase reporter system.
Figure 26A:
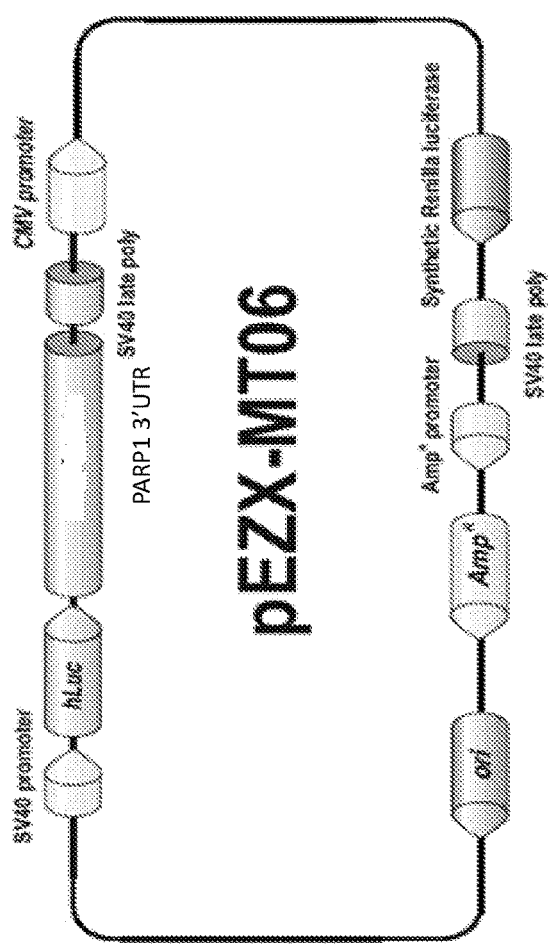
Figure 28:
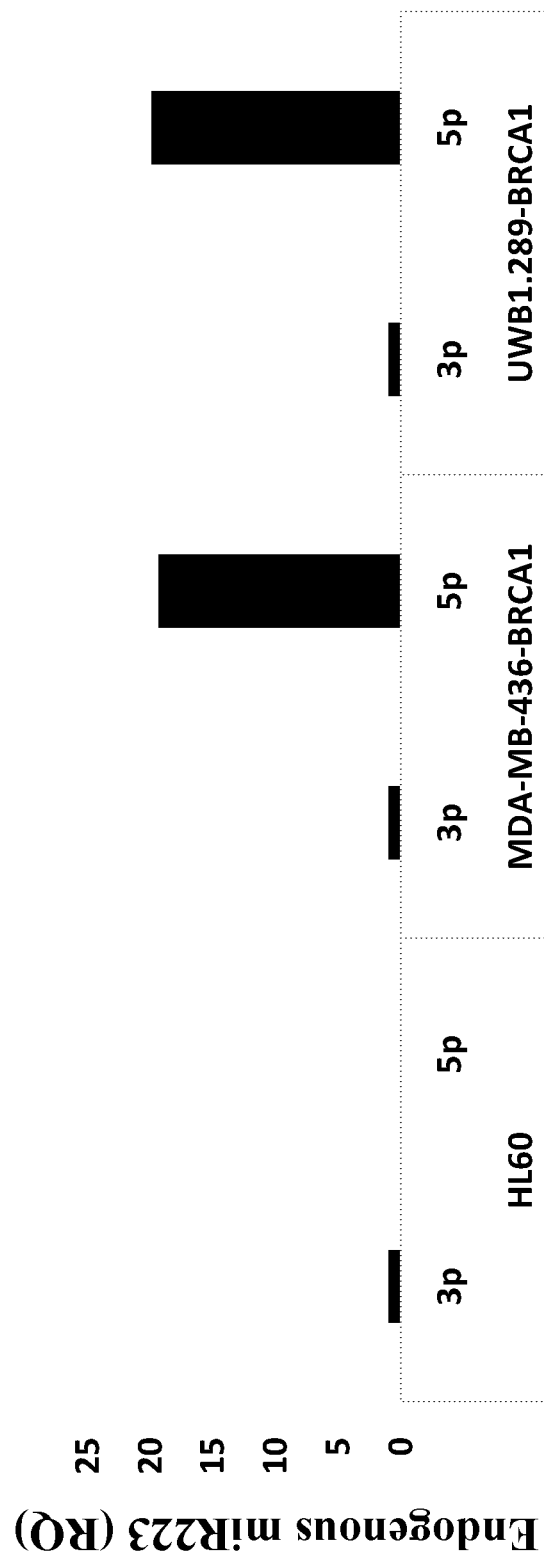
FIG. 28 compares the levels of miR223-5p and miR223-3p in cells.
Figures 29A, 29B:
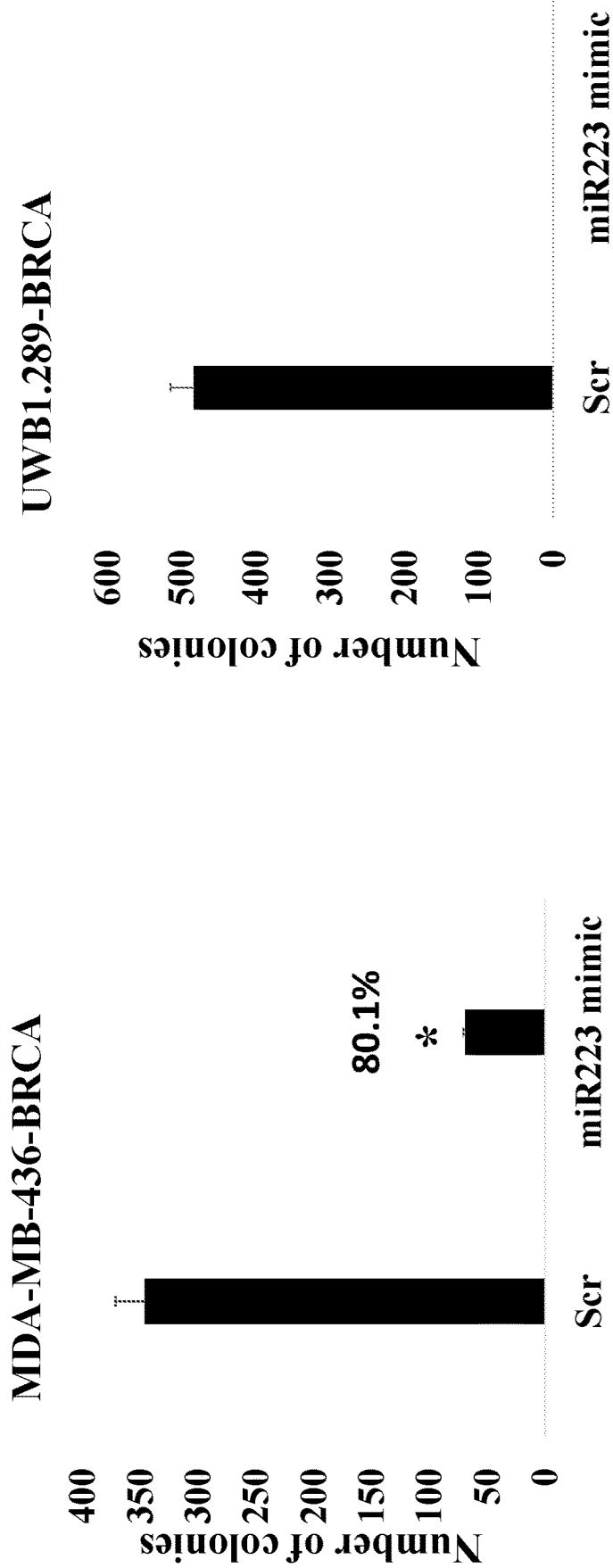
FIGS. 29A-29D. Reconstitution of miR223-3p is toxic to BRCA1-deficient cancer cells. In a colony formation assay, cell lines MDA-MB-436 (FIG. 29A) and UWB1.289 (FIG. 29B), deficient in BRCA1, show decreased number of colonies when cells are treated with mir223 mimic (miR223-3p). Colony formation is shown in FIG. 29C
Figure 29D:
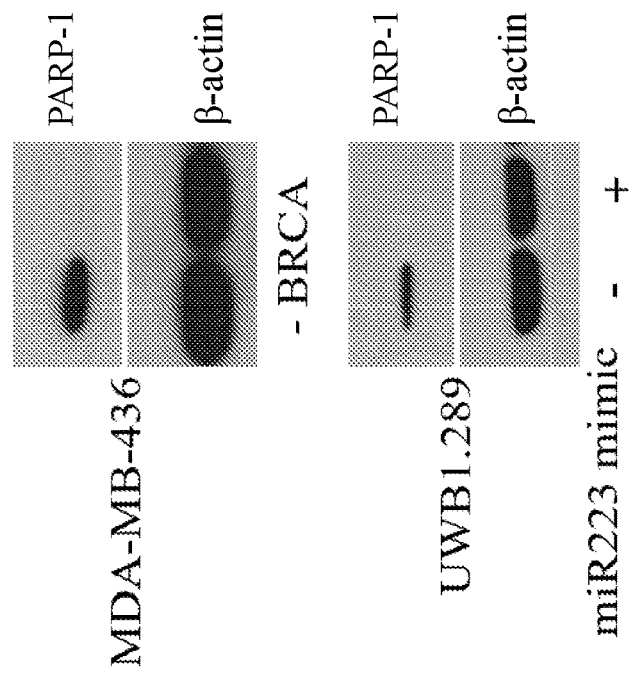
Figure 29C:
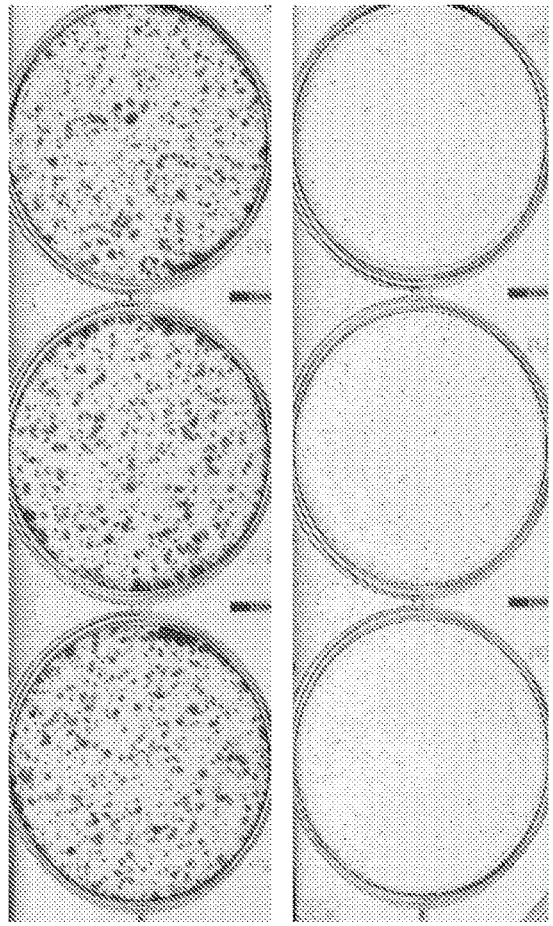
Figure 30B:
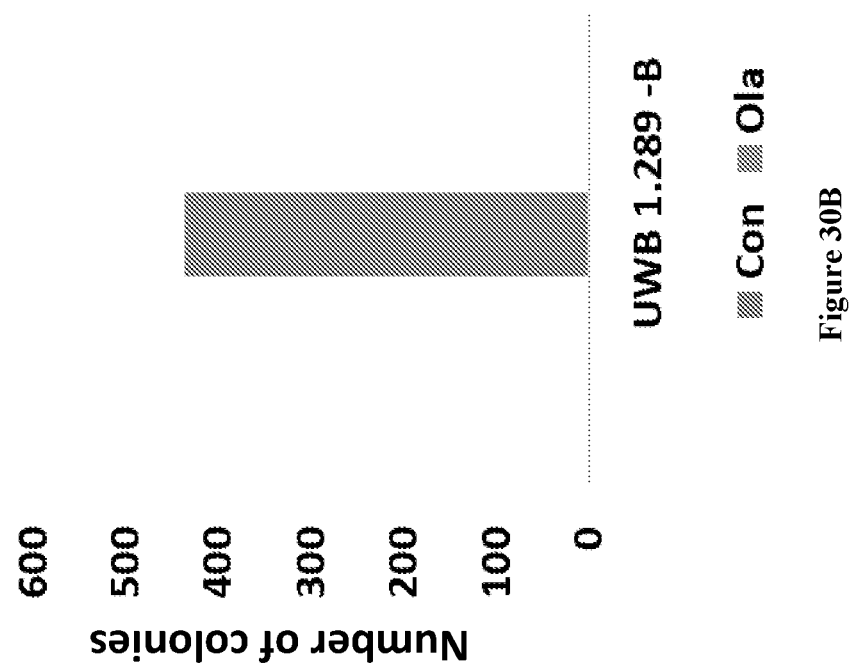
FIGS. 30A-30B. Toxicity of cells due to loss/inhibition of PARP1. Cells were treated with 50 nM siPARP or 25 nM miR223-3p (FIG. 30A). Cells treated with 3 uM Olaparib continuously for 15 days (FIG. 30B).
Figure 30A:
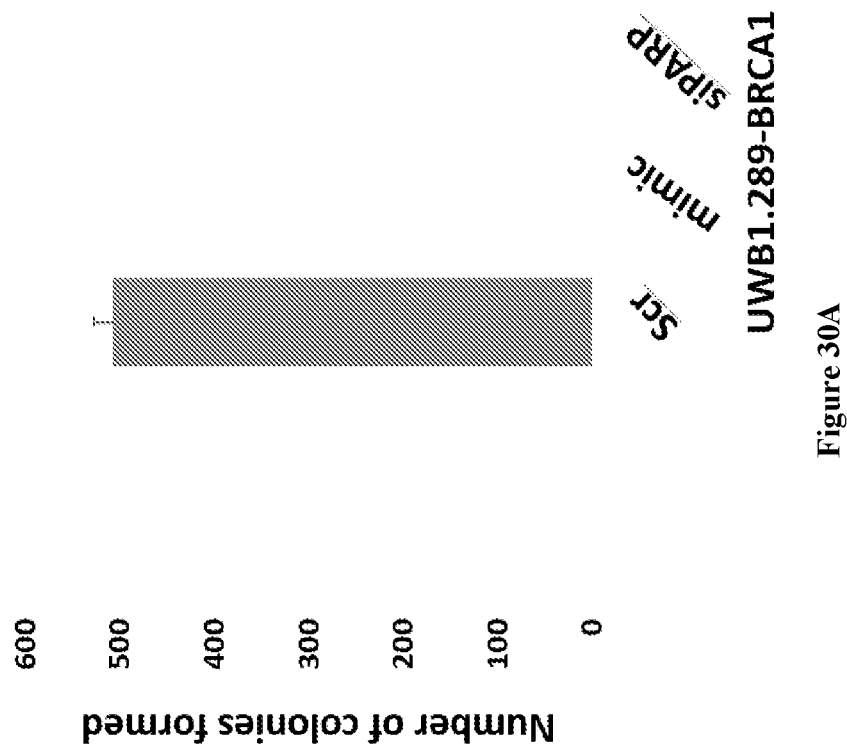
Figures 31A, 31B:
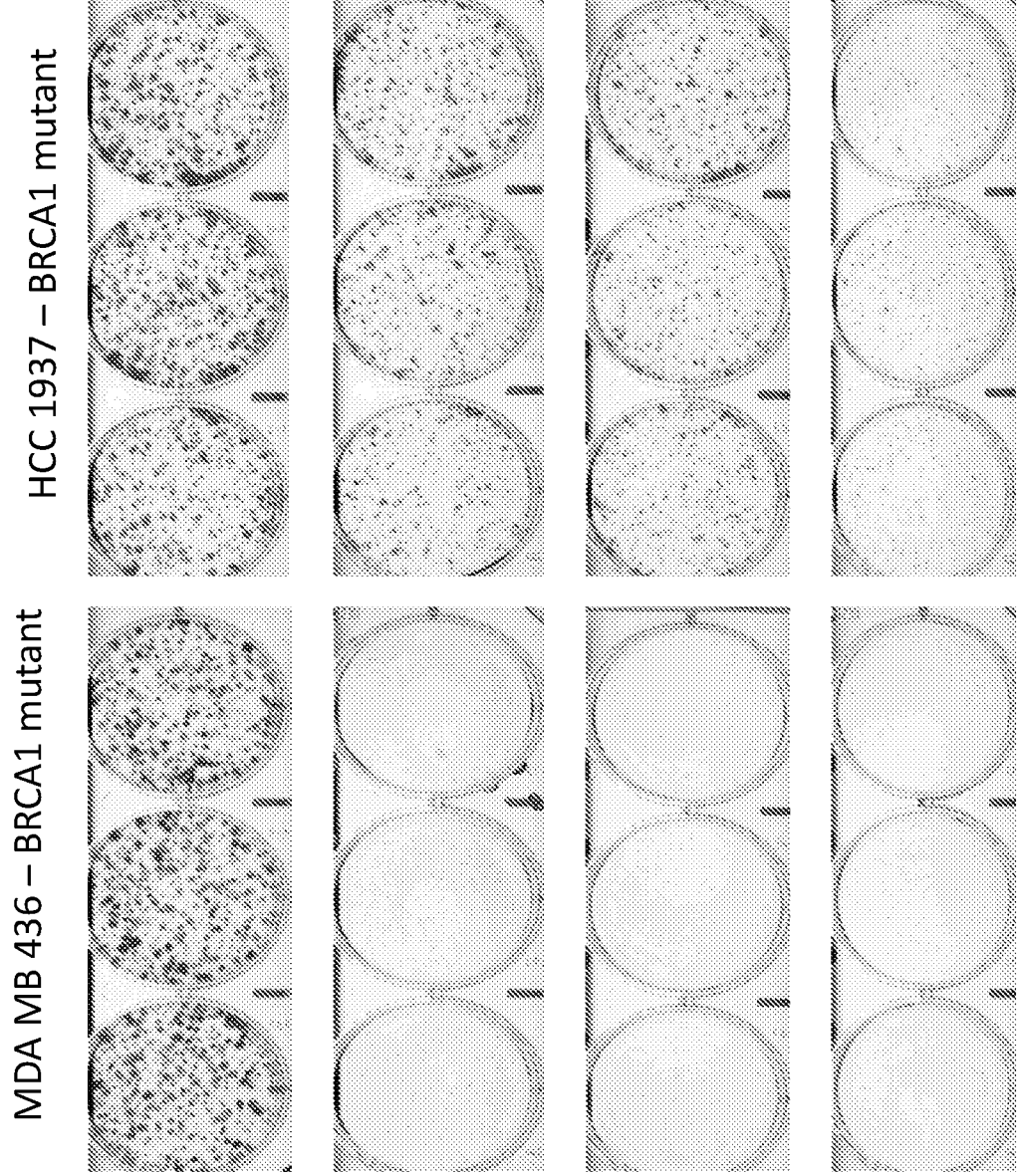
FIGS. 31A-31D. Colony formation of cells treated with olaparib (FIGS. 31A and 31B) and miR223-3p (FIG. 31D).
Figure 31D:
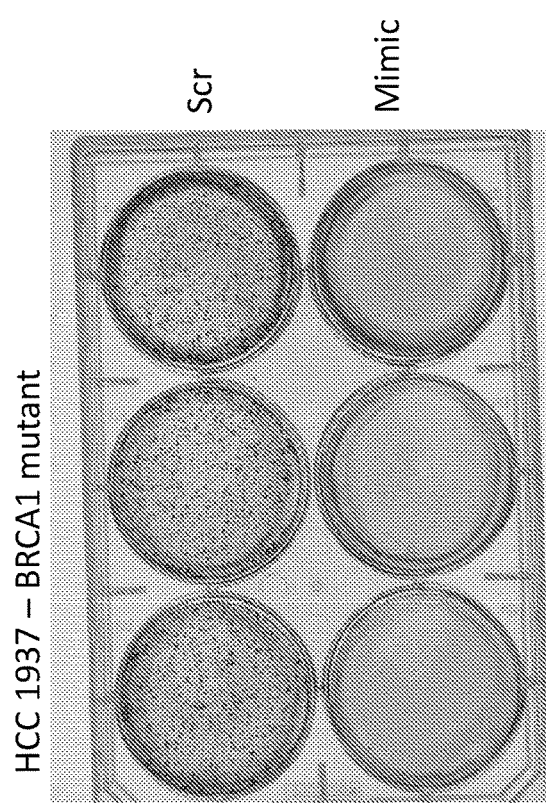
Figure 31C:
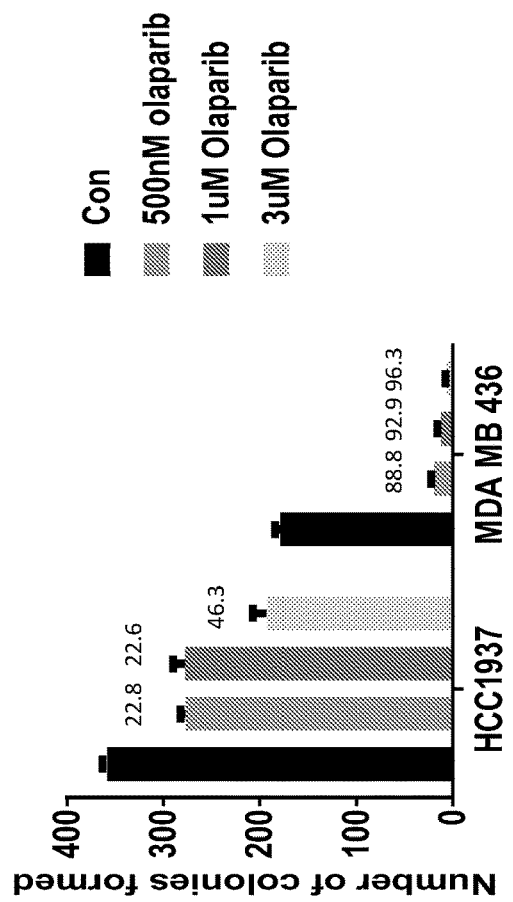

Luciferase assay for assessing stability of PARP1 3' UTR mRNA. A549 cells were transfected with miR223-3p mimic using RNAiMAX as above. After 6 hours, these cells were transfected with PARP 3'UTR plasmid fused with dual luciferase reporter from GeneCopoeia using Lipofectamine 2000. 48 hours post-transfection, cells were collected and assessed for luciferase activity using Luc-Pair Dual Luciferase assay kit from GeneCopoeia. The firefly luciferase activity is normalized against *Renilla* luciferase, which serves as a transfection control. Results are shown in FIGS. 26A-B.

Statistical Analysis. Microsoft Excel or GraphPad Prism software were used for all statistical analysis. Unpaired student t-test generated the p values and a value of <0.05 was considered statistically significant.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Deshpande et al. (2013), Current trends in the use of liposomes for tumor targeting, *Nanomedicine (Loud)*; 8(9):doi:10.2217/nnm.13.118.

2. Nicoli et al. (2015), Enhanced gene silencing through human serum albumin-mediated delivery of polyethylenimine-siRNA polyplexes, PLOS ONE; DOI:10.1371/journal.pone.0122581.

3. Maherani et al., Liposomes: a review of manufacturing techniques and targeting strategies, *Current Nanoscience*; 7:436-452.

4. Lee et al., Targeted lung cancer therapy using ephrinA1-loaded albumin microspheres. J Pharm Pharmacol. 2011 November; 63(11):1401-10.

The invention claimed is:

1. A pharmaceutical composition comprising a microRNA (miRNA), wherein the miRNA is a modified miR-223-3p having the sequence selected from SEQ ID NOs: 76-89, 93, and 95-108.

2. The pharmaceutical composition of claim 1, wherein the miRNA is chemically modified in a manner that decreases the susceptibility of the miRNA to degradation.

3. The pharmaceutical composition of claim 2, wherein the chemical modification comprises uridylation, adenylation, 2'-deoxy-modification, 2'-O-methylation, 2'-fluorination, 2'-methoxyethylation or 2'-aminoethylation or adding phosphorothionate, methyl phosphonate or phosphoramidate moieties.

4. The pharmaceutical composition of claim 1, wherein the pharmaceutical composition comprises miRNA encapsulated in liposomes.

5. The pharmaceutical composition of claim 1, wherein the miRNA is complexed with serum albumin.

6. A method of treating cancer, the method comprising administering an effective amount of a pharmaceutical composition of claim 1 to a subject in need thereof, wherein the cancer is a leukemia, or wherein the cancer cells of the subject have one or more mutations in BRCA1 or BAP1 genes.

7. The method of claim 6, the method further comprising administering a second therapeutic agent for the treatment of cancer to the subject.

8. The method of claim 7, wherein said second therapeutic agent is selected from adriamycin, cytarabine, daunorubicin, idarubicin, cisplatin, oxaliplatin, carboplatin, irinotecan, camptothecin and derivatives thereof, capecitabine, methotrexate, chlorambucil, busulfan, clofarabine, fludarabine, pentostatin, cyclophosphamide, etoposide, fluorouracil, gemcitabine, ifosfamide, nelarabine, mechlorethamine, procarbazine, taxol, taxotere, topotecan, vincristine and vinblastine.

9. The method of claim 8, wherein said second therapeutic agent is administered in subtherapeutic amounts.

10. The method according to claim 6, wherein the cancer is homologous recombination (HR)-deficient ovarian cancer, IDH1-mutant acute leukemia and glioblastoma, BAP1-mutant mesothelioma, BAP1-mutant melanoma, BAP1-mutant cholangiocarcinoma, or BAP1-mutant renal cell carcinoma.

11. The method according to claim 6, wherein the cancer is homologous recombination (HR)-deficient ovarian cancer, IDH1-mutant acute leukemia and glioblastoma, BAP1-mutant mesothelioma, BAP1-mutant melanoma, BAP1-mutant cholangiocarcinoma, or BAP1-mutant renal cell carcinoma.

* * * * *